United States Patent [19]
Heartlein et al.

[11] Patent Number: 5,817,789
[45] Date of Patent: Oct. 6, 1998

[54] CHIMERIC PROTEINS FOR USE IN TRANSPORT OF A SELECTED SUBSTANCE INTO CELLS

[75] Inventors: Michael W. Heartlein, Boxborough; Jeffrey F. Lemontt, West Newton; Michael F. Concino, Newton, all of Mass.

[73] Assignee: Transkaryotic Therapies, Inc., Cambridge, Mass.

[21] Appl. No.: 470,058

[22] Filed: Jun. 6, 1995

[51] Int. Cl.⁶ .................. C07K 14/705; C07K 14/79; C12N 5/10; C12N 15/12
[52] U.S. Cl. .................. 536/23.4; 435/325; 435/366; 435/320.1; 435/69.1; 530/350; 514/12
[58] Field of Search .................. 530/350, 387.3, 530/388.2, 402; 536/23.5, 23.4; 435/69.1, 320.1, 240.1, 325, 366; 514/12

[56] References Cited

U.S. PATENT DOCUMENTS

| | | | |
|---|---|---|---|
| 5,154,924 | 10/1992 | Friden | 424/85.91 |
| 5,182,107 | 1/1993 | Friden | 424/85.91 |
| 5,292,869 | 3/1994 | Schryvers | 530/413 |
| 5,416,016 | 5/1995 | Low et al. | 435/240.1 |
| 5,527,527 | 6/1996 | Friden | 424/178.1 |
| 5,554,386 | 9/1996 | Groman et al. | 424/488 |
| 5,672,683 | 9/1997 | Friden et al. | 530/350 |

FOREIGN PATENT DOCUMENTS

| | | |
|---|---|---|
| WO 91/14438 | 10/1991 | WIPO . |
| WO 92/11383 | 7/1992 | WIPO . |
| WO 95/02421 | 1/1995 | WIPO . |

OTHER PUBLICATIONS

Seligman, P., et al., "Molecular Mechanisms of Iron Metabolism", *The Molecular Basis of Blood Diseases*, at pp. 219–229 (1987) W.B. Saunders Co.

Wagner, E., et al., "Transferrin–polycation conjugates as carriers for DNA uptake into cells", *Proc. Natl. Acad. Sci.*, 87:3410–3414 (1990).

Yan, H., et al., "Chimeric NGF–EGF Receptors Define Domains Responsible for Neuronal Differentiation", *Science*, 252:561–564 (1991).

Hobbs, H.H., et al., "The LDL Recpetor Locus in Familial Hypercholesterolemia: Mutational Analysis of a Membrane Protein", *Annu.Rev.Genet*, 24:133–170 (1990).

Capon, D.J., et al., "Designing CD4 immunoadhesions for AIDS therapy", *Nature*, 337:525–531 (1989).

Traunecker, A., et al., "Highly efficient neutralization of HIV with recombinant CD4–immunoglobulin molecules", *Nature*, 339:68–70 (1989).

Styles et al., Rat monoclonal antibodies to the external domain of the product of the c–erbB–2 proto–oncogene, Int. J. Cancer, 45: 320–324, 1990.

Shin et al., Transferrin–antibody fusion proteins are effective in brain targeting, Proc. Natl. Acad. Sci. USA, 92:2820–2824, Mar. 1995.

Wagner, E., et al., "Delivery of drugs, proteins and genes into cells using transferrin as a ligand for receptor–mediated endocytosis", *Advanced Drug Delivery Reviews*, 14:113–135 (1994).

*Primary Examiner*—Stephen Walsh
*Assistant Examiner*—Claire M. Kaufmann
*Attorney, Agent, or Firm*—Fish & Richardson P.C.

[57] ABSTRACT

Chimeric proteins, which bind a cell surface receptors, useful in transporting a selected substance present in extracellular fluids, such as blood or lymph, into cells; quantitative assays for the selected substance using chimeric proteins; DNA encoding the chimeric proteins; plasmids which contain DNA encoding the chimeric proteins; mammalian cells, modified to contain DNA encoding the chimeric proteins, which express and, optionally, secrete the chimeric proteins; a method of producing the chimeric proteins; a method of isolating the chimeric proteins; a method of using the chimeric proteins to assay the selected substance; and a method of reducing extracellular levels of the selected substance through administration of the chimeric protein, which results in transport of the selected substance into cells.

10 Claims, 17 Drawing Sheets

```
  1 AGAGGCTGCGAGC ATG GGG CCC TGG GGC TGG AAA TTG CGC TGG ACC
               1►Met Gly Pro Trp Gly Trp Lys Leu Arg Trp Thr

47 GTC GCC TTG CTC CTC GCC GCG GCG GGG ACT GCA GTG GGC GAC AGA
 12►Val Ala Leu Leu Leu Ala Ala Ala Gly Thr Ala Val Gly Asp Arg

92 TGT GAA AGA AAC GAG TTC CAG TGC CAA GAC GGG AAA TGC ATC TCC
 27►Cys Glu Arg Asn Glu Phe Gln Cys Gln Asp Gly Lys Cys Ile Ser

137 TAC AAG TGG GTC TGC GAT GGC AGC GCT GAG TGC AGG GAT GGC TCT
 42►Tyr Lys Trp Val Cys Asp Gly Ser Ala Glu Cys Gln Asp Gly Ser

182 GAT GAG TCC CAG GAG ACG TGC TTG TCT GTC ACC TGC AAA TCC GGG
 57►Asp Glu Ser Gln Glu Thr Cys Leu Ser Val Thr Cys Lys Ser Gly

227 GAC TTC AGC TGT GGG GGC CGT GTC AAC CGC TGC ATT CCT CAG TTC
 72►Asp Phe Ser Cys Gly Gly Arg Val Asn Arg Cys Ile Pro Gln Phe

272 TGG AGG TGC GAT GGC CAA GTG GAC TGC GAC AAC GGC TCA GAC GAG
 87►Trp Arg Cys Asp Gly Gln Val Asp Cys Asp Asn Gly Ser Asp Glu

317 CAA GGC TGT CCC CCC AAG ACG TGC TCC CAG GAC GAG TTT CGC TGC
102►Gln Gly Cys Pro Pro Lys Thr Cys Ser Gln Asp Glu Phe Arg Cys

362 CAC GAT GGG AAG TGC ATC TCT CGG CAG TTC GTC TGT GAC TCA GAC
117►His Asp Gly Lys Cys Ile Ser Arg Gln Phe Val Cys Asp Ser Asp

407 CGG GAC TGC TTG GAC GGC TCA GAC GAG GCC TCC TGC CCG GTG CTC
132►Arg Asp Cys Leu Asp Gly Ser Asp Glu Ala Ser Cys Pro Val Leu

452 ACC TGT GGT CCC GCC AGC TTC CAG TGC AAC AGC TCC ACC TGC ATC
147►Thr Cys Gly Pro Ala Ser Phe Gln Cys Asn Ser Ser Thr Cys Ile

497 CCC CAG CTG TGG GCC TGC GAC AAC GAC CCC GAC TGC GAA GAT GGC
162►Pro Gln Leu Trp Ala Cys Asp Asn Asp Pro Asp Cys Glu Asp Gly

542 TCG GAT GAG TGG CCG CAG CGC TGT AGG GGT CTT TAC GTG TTC CAA
177►Ser Asp Glu Trp Pro Gln Arg Cys Arg Gly Leu Tyr Val Phe Gln

587 GGG GAC AGT AGC CCC TGC TCG GCC TTC GAG TTC CAC TGC CTA AGT
192►Gly Asp Ser Ser Pro Cys Ser Ala Phe Glu Phe His Cys Leu Ser

632 GGC GAG TGC ATC CAC TCC AGC TGG CGC TGT GAT GGT GGC CCC GAC
207►Gly Glu Cys Ile His Ser Ser Trp Arg Cys Asp Gly Gly Pro Asp

677 TGC AAG GAC AAA TCT GAC GAG GAA AAC TGC GCT GTG GCC ACC TGT
222►Cys Lys Asp Lys Ser Asp Glu Glu Asn Cys Ala Val Ala Thr Cys
```

FIG. 3A

```
722  CGC CCT GAC GAA TTC CAG TGC TCT GAT GGA AAC TGC ATC CAT GGC
237▶ Arg Pro Asp Glu Phe Gln Cys Ser Asp Gly Asn Cys Ile His Gly

767  AGC CGG CAG TGT GAC CGG GAA TAT GAC TGC AAG GAC ATG AGC GAT
252▶ Ser Arg Gln Cys Asp Arg Glu Tyr Asp Cys Lys Asp Met Ser Asp

812  GAA GTT GGC TGC GTT AAT GTG ACA CTC TGC GAG GGA CCC AAC AAG
267▶ Glu Val Gly Cys Val Asn Val Thr Leu Cys Glu Gly Pro Asn Lys

857  TTC AAG TGT CAC AGC GGC GAA TGC ATC ACC CTG GAC AAA GTC TGC
282▶ Phe Lys Cys His Ser Gly Glu Cys Ile Thr Leu Asp Lys Val Cys

902  AAC ATG GCT AGA GAC TGC CGG GAC TGG TCA GAT GAA CCC ATC AAA
297▶ Asn Met Ala Arg Asp Cys Arg Asp Trp Ser Asp Glu Pro Ile Lys

947  GAG TGC GGG ACC AAC GAA TGC TTG GAC AAC AAC GGC GGC TGT TCC
312▶ Glu Cys Gly Thr Asn Glu Cys Leu Asp Asn Asn Gly Gly Cys Ser

992  CAC GTC TGC AAT GAC CTT AAG ATC GGC TAC GAG TGC CTG TGC CCC
327▶ His Val Cys Asn Asp Leu Lys Ile Gly Tyr Glu Cys Leu Cys Pro

1037 GAC GGC TTC CAG CTG GTG GCC CAG CGA AGA TGC GAA GAT ATC GAT
342▶ Asp Gly Phe Gln Leu Val Ala Gln Arg Arg Cys Glu Asp Ile Asp

1082 GAG TGT CAG GAT CCC GAC ACC TGC AGC CAG CTC TGC GTG AAC CTG
357▶ Glu Cys Gln Asp Pro Asp Thr Cys Ser Gln Leu Cys Val Asn Leu

1127 GAG GGT GGC TAC AAG TGC CAG TGT GAG GAA GGC TTC CAG CTG GAC
372▶ Glu Gly Gly Tyr Lys Cys Gln Cys Glu Glu Gly Phe Gln Leu Asp

1172 CCC CAC ACG AAG GCC TGC AAG GCT GTG GTC CCT GAT AAA ACT GTG
387▶ Pro His Thr Lys Ala Cys Lys Ala Val Val Pro Asp Lys Thr Val

1217 AGA TGG TGT GCA GTG TCG GAG CAT GAG GCC ACT AAG TGC CAG AGT
402▶ Arg Trp Cys Ala Val Ser Glu His Glu Ala Thr Lys Cys Gln Ser

1262 TTC CGC GAC CAT ATG AAA AGC GTC ATT CCA TCC GAT GGT CCC AGT
417▶ Phe Arg Asp His Met Lys Ser Val Ile Pro Ser Asp Gly Pro Ser

1307 GTT GCT TGT GTG AAG AAA GCC TCC TAC CTT GAT TGC ATC AGG GCC
432▶ Val Ala Cys Val Lys Lys Ala Ser Tyr Leu Asp Cys Ile Arg Ala

1352 ATT GCG GCA AAC GAA GCG GAT GCT GTG ACA CTG GAT GCA GGT TTG
447▶ Ile Ala Ala Asn Glu Ala Asp Ala Val Thr Leu Asp Ala Gly Leu

1397 GTG TAT GAT GCT TAC TTG GCT CCC AAT AAC CTG AAG CCT GTG GTG
462▶ Val Tyr Asp Ala Tyr Leu Ala Pro Asn Asn Leu Lys Pro Val Val

1442 GCA GAG TTC TAT GGG TCA AAA GAG GAT CCA CAG ACT TTC TAT TAT
477▶ Ala Glu Phe Tyr Gly Ser Lys Glu Asp Pro Gln Thr Phe Tyr Tyr
```

FIG. 3B

```
1487 GCT GTT GCT GTG GTG AAG AAG GAT AGT GGC TTC CAG ATG AAC CAG
492▶Ala Val Ala Val Val Lys Lys Asp Ser Gly Phe Gln Met Asn Gln

1532 CTT CGA GGC AAG AAG TCC TGC CAC ACG GGT CTA GGC AGG TCC GCT
507▶Leu Arg Gly Lys Lys Ser Cys His Thr Gly Leu Gly Arg Ser Ala

1577 GGG TGG AAC ATC CCC ATA GGC TTA CTT TAC TGT GAC TTA CCT GAG
522▶Gly Trp Asn Ile Pro Ile Gly Leu Leu Tyr Cys Asp Leu Pro Glu

1622 CCA CGT AAA CCT CTT GAG AAA GCA GTG GCC AAT TTC TTC TCG GGC
537▶Pro Arg Lys Pro Leu Glu Lys Ala Val Ala Asn Phe Phe Ser Gly

1667 AGC TGT GCC CCT TGT GCG GAT GGG ACG GAC TTC CCC CAG CTG TGT
552▶Ser Cys Ala Pro Cys Ala Asp Gly Thr Asp Phe Pro Gln Leu Cys

1712 CAA CTG TGT CCA GGG TGT GGC TGC TCC ACC CTT AAC CAA TAC TTC
567▶Gln Leu Cys Pro Gly Cys Gly Cys Ser Thr Leu Asn Gln Tyr Phe

1757 GGC TAC TCG GGA GCC TTC AAG TGT CTG AAG GAT GGT GCT GGG GAT
582▶Gly Tyr Ser Gly Ala Phe Lys Cys Leu Lys Asp Gly Ala Gly Asp

1802 GTG GCC TTT GTC AAG CAC TCG ACT ATA TTT GAG AAC TTG GCA AAC
597▶Val Ala Phe Val Lys His Ser Thr Ile Phe Glu Asn Leu Ala Asn

1847 AAG GCT GAC AGG GAC CAG TAT GAG CTG CTT TGC CTA GAC AAC ACC
612▶Lys Ala Asp Arg Asp Gln Tyr Glu Leu Leu Cys Leu Asp Asn Thr

1892 CGG AAG CCG GTA GAT GAA TAC AAG GAC TGC CAC TTG GCC CAG GTC
627▶Arg Lys Pro Val Asp Glu Tyr Lys Asp Cys His Leu Ala Gln Val

1937 CCT TCT CAT ACC GTC GTG GCC CGA AGT ATG GGC GGC AAG GAG GAC
642▶Pro Ser His Thr Val Val Ala Arg Ser Met Gly Gly Lys Glu Asp

1982 TTG ATC TGG GAG CTT CTC AAC CAG GCC CAG GAA CAT TTT GGC AAA
657▶Leu Ile Trp Glu Leu Leu Asn Gln Ala Gln Glu His Phe Gly Lys

2027 GAC AAA TCA AAA GAA TTC CAA CTA TTC AGC TCT CCT CAT GGG AAG
672▶Asp Lys Ser Lys Glu Phe Gln Leu Phe Ser Ser Pro His Gly Lys

2072 GAC CTG CTG TTT AAG GAC TCT GCC CAC GGG TTT TTA AAA GTC CCC
687▶Asp Leu Leu Phe Lys Asp Ser Ala His Gly Phe Leu Lys Val Pro

2117 CCA AGG ATG GAT GCC AAG ATG TAC CTG GGC TAT GAG TAT GTC ACT
702▶Pro Arg Met Asp Ala Lys Met Tyr Leu Gly Tyr Glu Tyr Val Thr

2162 GCC ATC CGG AAT CTA CGG GAA GGC ACA TGC CCA GAA GCC CCA ACA
717▶Ala Ile Arg Asn Leu Arg Glu Gly Thr Cys Pro Glu Ala Pro Thr

2207 GAT GAA TGC AAG CCT GTG AAG TGG TGT GCG CTG AGC CAC CAC GAG
732▶Asp Glu Cys Lys Pro Val Lys Trp Cys Ala Leu Ser His His Glu
```

FIG. 3C

```
2252 AGG CTC AAG TGT GAT GAG TGG AGT GTT AAC AGT GTA GGG AAA ATA
747▶Arg Leu Lys Cys Asp Glu Trp Ser Val Asn Ser Val Gly Lys Ile

2297 GAG TGT GTA TCA GCA GAG ACC ACC GAA GAC TGC ATC GCC AAG ATC
762▶Glu Cys Val Ser Ala Glu Thr Thr Glu Asp Cys Ile Ala Lys Ile

2342 ATG AAT GGA GAA GCT GAT GCC ATG AGC TTG GAT GGA GGG TTT GTC
777▶Met Asn Gly Glu Ala Asp Ala Met Ser Leu Asp Gly Gly Phe Val

2387 TAC ATA GCG GGC AAG TGT GGT CTG GTG CCT GTC TTG GCA GAA AAC
792▶Tyr Ile Ala Gly Lys Cys Gly Leu Val Pro Val Leu Ala Glu Asn

2432 TAC AAT AAG AGC GAT AAT TGT GAG GAT ACA CCA GAG GCA GGG TAT
807▶Tyr Asn Lys Ser Asp Asn Cys Glu Asp Thr Pro Glu Ala Gly Tyr

2477 TTT GCT GTA GCA GTG GTG AAG AAA TCA GCT TCT GAC CTC ACC TGG
822▶Phe Ala Val Ala Val Val Lys Lys Ser Ala Ser Asp Leu Thr Trp

2522 GAC AAT CTG AAA GGC AAG AAG TCC TGC CAT ACG GCA GTT GGC AGA
837▶Asp Asn Leu Lys Gly Lys Lys Ser Cys His Thr Ala Val Gly Arg

2567 ACC GCT GGC TGG AAC ATC CCC ATG GGC CTG CTC TAC AAT AAG ATC
852▶Thr Ala Gly Trp Asn Ile Pro Met Gly Leu Leu Tyr Asn Lys Ile

2612 AAC CAC TGC AGA TTT GAT GAA TTT TTC AGT GAA GGT TGT GCC CCT
867▶Asn His Cys Arg Phe Asp Glu Phe Phe Ser Glu Gly Cys Ala Pro

2657 GGG TCT AAG AAA GAC TCC AGT CTC TGT AAG CTG TGT ATG GGC TCA
882▶Gly Ser Lys Lys Asp Ser Ser Leu Cys Lys Leu Cys Met Gly Ser

2702 GGC CTA AAC CTG TGT GAA CCC AAC AAC AAA GAG GGA TAC TAC GGC
897▶Gly Leu Asn Leu Cys Glu Pro Asn Asn Lys Glu Gly Tyr Tyr Gly

2747 TAC ACA GGC GCT TTC AGG TGT CTG GTT GAG AAG GGA GAT GTG GCC
912▶Tyr Thr Gly Ala Phe Arg Cys Leu Val Glu Lys Gly Asp Val Ala

2792 TTT GTG AAA CAC CAG ACT GTC CCA CAG AAC ACT GGG GGA AAA AAC
927▶Phe Val Lys His Gln Thr Val Pro Gln Asn Thr Gly Gly Lys Asn

2837 CCT GAT CCA TGG GCT AAG AAT CTG AAT GAA AAA GAC TAT GAG TTG
942▶Pro Asp Pro Trp Ala Lys Asn Leu Asn Glu Lys Asp Tyr Glu Leu

2882 CTG TGC CTT GAT GGT ACC AGG AAA CCT GTG GAG GAG TAT GCG AAC
957▶Leu Cys Leu Asp Gly Thr Arg Lys Pro Val Glu Glu Tyr Ala Asn

2927 TGC CAC CTG GCC AGA GCC CCG AAT CAC GCT GTG GTC ACA CGG AAA
972▶Cys His Leu Ala Arg Ala Pro Asn His Ala Val Val Thr Arg Lys

2972 GAT AAG GAA GCT TGC GTC CAC AAG ATA TTA CGT CAA CAG CAG CAC
987▶Asp Lys Glu Ala Cys Val His Lys Ile Leu Arg Gln Gln Gln His
```

FIG. 3D

```
3017 CTA TTT GGA AGC AAC GTA ACT GAC TGC TCG GGC AAC TTT TGT TTG
1002▶Leu Phe Gly Ser Asn Val Thr Asp Cys Ser Gly Asn Phe Cys Leu

3062 TTC CGG TCG GAA ACC AAG GAC CTT CTG TTC AGA GAT GAC ACA GTA
1017▶Phe Arg Ser Glu Thr Lys Asp Leu Leu Phe Arg Asp Asp Thr Val

3107 TGT TTG GCC AAA CTT CAT GAC AGA AAC ACA TAT GAA AAA TAC TTA
1032▶Cys Leu Ala Lys Leu His Asp Arg Asn Thr Tyr Glu Lys Tyr Leu

3152 GGA GAA GAA TAT GTC AAG GCT GTT GGT AAC CTG AGA AAA TGC TCC
1047▶Gly Glu Glu Tyr Val Lys Ala Val Gly Asn Leu Arg Lys Cys Ser

3197 ACC TCA TCA CTC CTG GAA GCC TGC ACT TTC CGT AGA CCT TAAAATCT
1062▶Thr Ser Ser Leu Leu Glu Ala Cys Thr Phe Arg Arg Pro •••

3244 CAGAGGTAGGGCTGCCACCAAGGTGAAGATGGGAACGCAGATGATCCATGAGTTTGCCCT

3304 GGTTTCACTGGCCCAAGTGGTTTGTGCTAACCACGTCTGTCTTCACAGCTCTGTGTTGCC

3364 ATGTGTGCTGAACAAAAAATAAAAATTATTATTGATTTTATATTTCGGGGGGGGGCTGC

3424 AGCCC
```

(SEQ ID NO:1)
(SEQ ID NO:2)

FIG. 3E

```
  1 AGAGGCTGCGAGC ATG GGG CCC TGG GGC TGG AAA TTG CGC TGG ACC
               1▶Met Gly Pro Trp Gly Trp Lys Leu Arg Trp Thr

47 GTC GCC TTG CTC CTC GCC GCG GCG GGG ACT GCA GTG GGC GAC AGA
 12▶Val Ala Leu Leu Leu Ala Ala Ala Gly Thr Ala Val Gly Asp Arg

92 TGT GAA AGA AAC GAG TTC CAG TGC CAA GAC GGG AAA TGC ATC TCC
 27▶Cys Glu Arg Asn Glu Phe Gln Cys Gln Asp Gly Lys Cys Ile Ser

137 TAC AAG TGG GTC TGC GAT GGC AGC GCT GAG TGC AGG GAT GGC TCT
 42▶Tyr Lys Trp Val Cys Asp Gly Ser Ala Glu Cys Gln Asp Gly Ser

182 GAT GAG TCC CAG GAG ACG TGC TTG TCT GTC ACC TGC AAA TCC GGG
 57▶Asp Glu Ser Gln Glu Thr Cys Leu Ser Val Thr Cys Lys Ser Gly

227 GAC TTC AGC TGT GGG GGC CGT GTC AAC CGC TGC ATT CCT CAG TTC
 72▶Asp Phe Ser Cys Gly Gly Arg Val Asn Arg Cys Ile Pro Gln Phe

272 TGG AGG TGC GAT GGC CAA GTG GAC TGC GAC AAC GGC TCA GAC GAG
 87▶Trp Arg Cys Asp Gly Gln Val Asp Cys Asp Asn Gly Ser Asp Glu

317 CAA GGC TGT CCC CCC AAG ACG TGC TCC CAG GAC GAG TTT CGC TGC
102▶Gln Gly Cys Pro Pro Lys Thr Cys Ser Gln Asp Glu Phe Arg Cys

362 CAC GAT GGG AAG TGC ATC TCT CGG CAG TTC GTC TGT GAC TCA GAC
117▶His Asp Gly Lys Cys Ile Ser Arg Gln Phe Val Cys Asp Ser Asp

407 CGG GAC TGC TTG GAC GGC TCA GAC GAG GCC TCC TGC CCG GTG CTC
132▶Arg Asp Cys Leu Asp Gly Ser Asp Glu Ala Ser Cys Pro Val Leu

452 ACC TGT GGT CCC GCC AGC TTC CAG TGC AAC AGC TCC ACC TGC ATC
147▶Thr Cys Gly Pro Ala Ser Phe Gln Cys Asn Ser Ser Thr Cys Ile

497 CCC CAG CTG TGG GCC TGC GAC AAC GAC CCC GAC TGC GAA GAT GGC
162▶Pro Gln Leu Trp Ala Cys Asp Asn Asp Pro Asp Cys Glu Asp Gly

542 TCG GAT GAG TGG CCG CAG CGC TGT AGG GGT CTT TAC GTG TTC CAA
177▶Ser Asp Glu Trp Pro Gln Arg Cys Arg Gly Leu Tyr Val Phe Gln

587 GGG GAC AGT AGC CCC TGC TCG GCC TTC GAG TTC CAC TGC CTA AGT
192▶Gly Asp Ser Ser Pro Cys Ser Ala Phe Glu Phe His Cys Leu Ser

632 GGC GAG TGC ATC CAC TCC AGC TGG CGC TGT GAT GGT GGC CCC GAC
207▶Gly Glu Cys Ile His Ser Ser Trp Arg Cys Asp Gly Gly Pro Asp

677 TGC AAG GAC AAA TCT GAC GAG GAA AAC TGC GCT GTG GCC ACC TGT
222▶Cys Lys Asp Lys Ser Asp Glu Glu Asn Cys Ala Val Ala Thr Cys
```

FIG. 5A

```
722  CGC CCT GAC GAA TTC CAG TGC TCT GAT GGA AAC TGC ATC CAT GGC
237▶ Arg Pro Asp Glu Phe Gln Cys Ser Asp Gly Asn Cys Ile His Gly

767  AGC CGG CAG TGT GAC CGG GAA TAT GAC TGC AAG GAC ATG AGC GAT
252▶ Ser Arg Gln Cys Asp Arg Glu Tyr Asp Cys Lys Asp Met Ser Asp

812  GAA GTT GGC TGC GTT AAT GTG ACA CTC TGC GAG GGA CCC AAC AAG
267▶ Glu Val Gly Cys Val Asn Val Thr Leu Cys Glu Gly Pro Asn Lys

857  TTC AAG TGT CAC AGC GGC GAA TGC ATC ACC CTG GAC AAA GTC TGC
282▶ Phe Lys Cys His Ser Gly Glu Cys Ile Thr Leu Asp Lys Val Cys

902  AAC ATG GCT AGA GAC TGC CGG GAC TGG TCA GAT GAA CCC ATC AAA
297▶ Asn Met Ala Arg Asp Cys Arg Asp Trp Ser Asp Glu Pro Ile Lys

947  GAG TGC GGG ACC AAC GAA TGC TTG GAC AAC AAC GGC GGC TGT TCC
312▶ Glu Cys Gly Thr Asn Glu Cys Leu Asp Asn Asn Gly Gly Cys Ser

992  CAC GTC TGC AAT GAC CTT AAG ATC GGC TAC GAG TGC CTG TGC CCC
327▶ His Val Cys Asn Asp Leu Lys Ile Gly Tyr Glu Cys Leu Cys Pro

1037 GAC GGC TTC CAG CTG GTG GCC CAG CGA AGA TGC GAA GAT ATC GAT
342▶ Asp Gly Phe Gln Leu Val Ala Gln Arg Arg Cys Glu Asp Ile Asp

1082 GAG TGT CAG GAT CCC GAC ACC TGC AGC CAG CTC TGC GTG AAC CTG
357▶ Glu Cys Gln Asp Pro Asp Thr Cys Ser Gln Leu Cys Val Asn Leu

1127 GAG GGT GGC TAC AAG TGC CAG TGT GAG GAA GGC TTC CAG CTG GAC
372▶ Glu Gly Gly Tyr Lys Cys Gln Cys Glu Glu Gly Phe Gln Leu Asp

1172 CCC CAC ACG AAG GCC TGC AAG GCT GTG GGC TCC ATC GCC TAC CTC
387▶ Pro His Thr Lys Ala Cys Lys Ala Val Gly Ser Ile Ala Tyr Leu

1217 TTC TTC ACC AAC CGG CAC GAG GTC AGG AAG ATG ACG CTG GAC CGG
402▶ Phe Phe Thr Asn Arg His Glu Val Arg Lys Met Thr Leu Asp Arg

1262 AGC GAG TAC ACC AGC CTC ATC CCC AAC CTG AGG AAC GTG GTC GCT
417▶ Ser Glu Tyr Thr Ser Leu Ile Pro Asn Leu Arg Asn Val Val Ala

1307 CTG GAC ACG GAG GTG GCC AGC AAT AGA ATC TAC TGG TCT GAC CTG
432▶ Leu Asp Thr Glu Val Ala Ser Asn Arg Ile Tyr Trp Ser Asp Leu

1352 TCC CAG AGA ATG ATC TGC AGC ACC CAG CTT GAC AGA GCC CAC GGC
447▶ Ser Gln Arg Met Ile Cys Ser Thr Gln Leu Asp Arg Ala His Gly

1397 GTC TCT TCC TAT GAC ACC GTC ATC AGC AGG GAC ATC CAG GCC CCC
462▶ Val Ser Ser Tyr Asp Thr Val Ile Ser Arg Asp Ile Gln Ala Pro

1442 GAC GGG CTG GCT GTG GAC TGG ATC CAC AGC AAC ATC TAC TGG ACC
477▶ Asp Gly Leu Ala Val Asp Trp Ile His Ser Asn Ile Tyr Trp Thr
```

FIG. 5B

```
1487  GAC  TCT  GTC  CTG  GGC  ACT  GTC  TCT  GTT  GCG  GAT  ACC  AAG  GGC  GTG
 492▶ Asp  Ser  Val  Leu  Gly  Thr  Val  Ser  Val  Ala  Asp  Thr  Lys  Gly  Val

1532  AAG  AGG  AAA  ACG  TTA  TTC  AGG  GAG  AAC  GGC  TCC  AAG  CCA  AGG  GCC
 507▶ Lys  Arg  Lys  Thr  Leu  Phe  Arg  Glu  Asn  Gly  Ser  Lys  Pro  Arg  Ala

1577  ATC  GTG  GTG  GAT  CCT  GTT  CAT  GGC  TTC  ATG  TAC  TGG  ACT  GAC  TGG
 522▶ Ile  Val  Val  Asp  Pro  Val  His  Gly  Phe  Met  Tyr  Trp  Thr  Asp  Trp

1622  GGA  ACT  CCC  GCC  AAG  ATC  AAG  AAA  GGG  GGC  CTG  AAT  GGT  GTG  GAC
 537▶ Gly  Thr  Pro  Ala  Lys  Ile  Lys  Lys  Gly  Gly  Leu  Asn  Gly  Val  Asp

1667  ATC  TAC  TCG  CTG  GTG  ACT  GAA  AAC  ATT  CAG  TGG  CCC  AAT  GGC  ATC
 552▶ Ile  Tyr  Ser  Leu  Val  Thr  Glu  Asn  Ile  Gln  Trp  Pro  Asn  Gly  Ile

1712  ACC  CTA  GAT  CTC  CTC  AGT  GGC  CGC  CTC  TAC  TGG  GTT  GAC  TCC  AAA
 567▶ Thr  Leu  Asp  Leu  Leu  Ser  Gly  Arg  Leu  Tyr  Trp  Val  Asp  Ser  Lys

1757  CTT  CAC  TCC  ATC  TCA  AGC  ATC  GAT  GTC  AAT  GGG  GGC  AAC  CGG  AAG
 582▶ Leu  His  Ser  Ile  Ser  Ser  Ile  Asp  Val  Asn  Gly  Gly  Asn  Arg  Lys

1802  ACC  ATC  TTG  GAG  GAT  GAA  AAG  AGG  CTG  GCC  CAC  CCC  TTC  TCC  TTG
 597▶ Thr  Ile  Leu  Glu  Asp  Glu  Lys  Arg  Leu  Ala  His  Pro  Phe  Ser  Leu

1847  GCC  GTC  TTT  GAG  GAC  AAA  GTA  TTT  TGG  ACA  GAT  ATC  ATC  AAC  GAA
 612▶ Ala  Val  Phe  Glu  Asp  Lys  Val  Phe  Trp  Thr  Asp  Ile  Ile  Asn  Glu

1892  GCC  ATT  TTC  AGT  GCC  AAC  CGC  CTC  ACA  GGT  TCC  GAT  GTC  AAC  TTG
 627▶ Ala  Ile  Phe  Ser  Ala  Asn  Arg  Leu  Thr  Gly  Ser  Asp  Val  Asn  Leu

1937  TTG  GCT  GAA  AAC  CTA  CTG  TCC  CCA  GAG  GAT  ATG  GTC  CTC  TTC  CAC
 642▶ Leu  Ala  Glu  Asn  Leu  Leu  Ser  Pro  Glu  Asp  Met  Val  Leu  Phe  His

1982  AAC  CTC  ACC  CAG  CCA  AGA  GGA  GTG  AAC  TGG  TGT  GAG  AGG  ACC  ACC
 657▶ Asn  Leu  Thr  Gln  Pro  Arg  Gly  Val  Asn  Trp  Cys  Glu  Arg  Thr  Thr

2027  CTG  AGC  AAT  GGC  GGC  TGC  CAG  TAT  CTG  TGC  CTC  CCT  GCC  CCG  CAG
 672▶ Leu  Ser  Asn  Gly  Gly  Cys  Gln  Tyr  Leu  Cys  Leu  Pro  Ala  Pro  Gln

2072  ATC  AAC  CCC  CAC  TCG  CCC  AAG  TTT  ACC  TGC  GCC  TGC  CCG  GAC  GGC
 687▶ Ile  Asn  Pro  His  Ser  Pro  Lys  Phe  Thr  Cys  Ala  Cys  Pro  Asp  Gly

2117  ATG  CTG  CTG  GCC  AGG  GAC  ATG  AGG  AGC  TGC  CTC  ACA  GAG  GCT  GAG
 702▶ Met  Leu  Leu  Ala  Arg  Asp  Met  Arg  Ser  Cys  Leu  Thr  Glu  Ala  Glu

2162  GCT  GCA  GTG  GCC  ACC  CAG  GAG  ACA  TCC  ACC  GTC  AGG  CTA  AAG  GTC
 717▶ Ala  Ala  Val  Ala  Thr  Gln  Glu  Thr  Ser  Thr  Val  Arg  Leu  Lys  Val

2207  GTC  CCT  GAT  AAA  ACT  GTG  AGA  TGG  TGT  GCA  GTG  TCG  GAG  CAT  GAG
 732▶ Val  Pro  Asp  Lys  Thr  Val  Arg  Trp  Cys  Ala  Val  Ser  Glu  His  Glu
```

FIG. 5C

```
2252 GCC ACT AAG TCG CAG AGT TTC CGC GAC CAT ATG AAA AGC GTC ATT
747▶Ala Thr Lys Cys Gln Ser Phe Arg Asp His Met Lys Ser Val Ile

2297 CCA TCC GAT GGT CCC AGT GTT GCT TGT GTG AAG AAA GCC TCC TAC
762▶Pro Ser Asp Gly Pro Ser Val Ala Cys Val Lys Lys Ala Ser Tyr

2342 CTT GAT TGC ATC AGG GCC ATT GCG GCA AAC GAA GCG GAT GCT GTG
777▶Leu Asp Cys Ile Arg Ala Ile Ala Ala Asn Glu Ala Asp Ala Val

2387 ACA CTG GAT GCA GGT TTG GTG TAT GAT GCT TAC TTG GCT CCC AAT
792▶Thr Leu Asp Ala Gly Leu Val Tyr Asp Ala Tyr Leu Ala Pro Asn

2432 AAC CTG AAG CCT GTG GTG GCA GAG TTC TAT GGG TCA AAA GAG GAT
807▶Asn Leu Lys Pro Val Val Ala Glu Phe Tyr Gly Ser Lys Glu Asp

2477 CCA CAG ACT TTC TAT TAT GCT GTT GCT GTG GTG AAG AAG GAT AGT
822▶Pro Gln Thr Phe Tyr Tyr Ala Val Ala Val Val Lys Lys Asp Ser

2522 GGC TTC CAG ATG AAC CAG CTT CGA GGC AAG AAG TCC TGC CAC ACG
837▶Gly Phe Gln Met Asn Gln Leu Arg Gly Lys Lys Ser Cys His Thr

2567 GGT CTA GGC AGG TCC GCT GGG TGG AAC ATC CCC ATA GGC TTA CTT
852▶Gly Leu Gly Arg Ser Ala Gly Trp Asn Ile Pro Ile Gly Leu Leu

2612 TAC TGT GAC TTA CCT GAG CCA CGT AAA CCT CTT GAG AAA GCA GTG
867▶Tyr Cys Asp Leu Pro Glu Pro Arg Lys Pro Leu Glu Lys Ala Val

2657 GCC AAT TTC TTC TCG GGC AGC TGT GCC CCT TGT GCG GAT GGG ACG
882▶Ala Asn Phe Phe Ser Gly Ser Cys Ala Pro Cys Ala Asp Gly Thr

2702 GAC TTC CCC CAG CTG TGT CAA CTG TGT CCA GGG TGT GGC TGC TCC
897▶Asp Phe Pro Gln Leu Cys Gln Leu Cys Pro Gly Cys Gly Cys Ser

2747 ACC CTT AAC CAA TAC TTC GGC TAC TCG GGA GCC TTC AAG TGT CTG
912▶Thr Leu Asn Gln Tyr Phe Gly Tyr Ser Gly Ala Phe Lys Cys Leu

2792 AAG GAT GGT GCT GGG GAT GTG GCC TTT GTC AAG CAC TCG ACT ATA
927▶Lys Asp Gly Ala Gly Asp Val Ala Phe Val Lys His Ser Thr Ile

2837 TTT GAG AAC TTG GCA AAC AAG GCT GAC AGG GAC CAG TAT GAG CTG
942▶Phe Glu Asn Leu Ala Asn Lys Ala Asp Arg Asp Gln Tyr Glu Leu

2882 CTT TGC CTA GAC AAC ACC CGG AAG CCG GTA GAT GAA TAC AAG GAC
957▶Leu Cys Leu Asp Asn Thr Arg Lys Pro Val Asp Glu Tyr Lys Asp

2927 TGC CAC TTG GCC CAG GTC CCT TCT CAT ACC GTC GTG GCC CGA AGT
972▶Cys His Leu Ala Gln Val Pro Ser His Thr Val Val Ala Arg Ser

2972 ATG GGC GGC AAG GAG GAC TTG ATC TGG GAG CTT CTC AAC CAG GCC
987▶Met Gly Gly Lys Glu Asp Leu Ile Trp Glu Leu Leu Asn Gln Ala
```

FIG. 5D

```
3017 CAG GAA CAT TT_ GGC AAA GAC AAA TCA AAA GAA TTC CAA CTA TTC
1002▶Gln Glu His Phe Gly Lys Asp Lys Ser Lys Glu Phe Gln Leu Phe

3062 AGC TCT CCT CAT GGG AAG GAC CTG CTG TTT AAG GAC TCT GCC CAC
1017▶Ser Ser Pro His Gly Lys Asp Leu Leu Phe Lys Asp Ser Ala His

3107 GGG TTT TTA AAA GTC CCC CCA AGG ATG GAT GCC AAG ATG TAC CTG
1032▶Gly Phe Leu Lys Val Pro Pro Arg Met Asp Ala Lys Met Tyr Leu

3152 GGC TAT GAG TAT GTC ACT GCC ATC CGG AAT CTA CGG GAA GGC ACA
1047▶Gly Tyr Glu Tyr Val Thr Ala Ile Arg Asn Leu Arg Glu Gly Thr

3197 TGC CCA GAA GCC CCA ACA GAT GAA TGC AAG CCT GTG AAG TGG TGT
1062▶Cys Pro Glu Ala Pro Thr Asp Glu Cys Lys Pro Val Lys Trp Cys

3242 GCG CTG AGC CAC CAC GAG AGG CTC AAG TGT GAT GAG TGG AGT GTT
1077▶Ala Leu Ser His His Glu Arg Leu Lys Cys Asp Glu Trp Ser Val

3287 AAC AGT GTA GGG AAA ATA GAG TGT GTA TCA GCA GAG ACC ACC GAA
1092▶Asn Ser Val Gly Lys Ile Glu Cys Val Ser Ala Glu Thr Thr Glu

3332 GAC TGC ATC GCC AAG ATC ATG AAT GGA GAA GCT GAT GCC ATG AGC
1107▶Asp Cys Ile Ala Lys Ile Met Asn Gly Glu Ala Asp Ala Met Ser

3377 TTG GAT GGA GGG TTT GTC TAC ATA GCG GGC AAG TGT GGT CTG GTG
1122▶Leu Asp Gly Gly Phe Val Tyr Ile Ala Gly Lys Cys Gly Leu Val

3422 CCT GTC TTG GCA GAA AAC TAC AAT AAG AGC GAT AAT TGT GAG GAT
1137▶Pro Val Leu Ala Glu Asn Tyr Asn Lys Ser Asp Asn Cys Glu Asp

3467 ACA CCA GAG GCA GGG TAT TTT GCT GTA GCA GTG GTG AAG AAA TCA
1152▶Thr Pro Glu Ala Gly Tyr Phe Ala Val Ala Val Val Lys Lys Ser

3512 GCT TCT GAC CTC ACC TGG GAC AAT CTG AAA GGC AAG AAG TCC TGC
1167▶Ala Ser Asp Leu Thr Trp Asp Asn Leu Lys Gly Lys Lys Ser Cys

3557 CAT ACG GCA GTT GGC AGA ACC GCT GGC TGG AAC ATC CCC ATG GGC
1182▶His Thr Ala Val Gly Arg Thr Ala Gly Trp Asn Ile Pro Met Gly

3602 CTG CTC TAC AAT AAG ATC AAC CAC TGC AGA TTT GAT GAA TTT TTC
1197▶Leu Leu Tyr Asn Lys Ile Asn His Cys Arg Phe Asp Glu Phe Phe

3647 AGT GAA GGT TGT GCC CCT GGG TCT AAG AAA GAC TCC AGT CTC TGT
1212▶Ser Glu Gly Cys Ala Pro Gly Ser Lys Lys Asp Ser Ser Leu Cys

3692 AAG CTG TGT ATG GGC TCA GGC CTA AAC CTG TGT GAA CCC AAC AAC
1227▶Lys Leu Cys Met Gly Ser Gly Leu Asn Leu Cys Glu Pro Asn Asn

3737 AAA GAG GGA TAC TAC GGC TAC ACA CGC GCT TTC AGG TGT CTG GTT
1242▶Lys Glu Gly Tyr Tyr Gly Tyr Thr Gly Ala Phe Arg Cys Leu Val
```

FIG. 5E

```
3782 GAG AAG GGA G   GTG GCC TTT GTG AAA CAC C   ACT GTC CCA CAG
1257 Glu Lys Gly Asp Val Ala Phe Val Lys His Gln Thr Val Pro Gln

3827 AAC ACT GGG GGA AAA AAC CCT GAT CCA TGG GCT AAG AAT CTG AAT
1272 Asn Thr Gly Gly Lys Asn Pro Asp Pro Trp Ala Lys Asn Leu Asn

3872 GAA AAA GAC TAT GAG TTG CTG TGC CTT GAT GGT ACC AGG AAA CCT
1287 Glu Lys Asp Tyr Glu Leu Leu Cys Leu Asp Gly Thr Arg Lys Pro

3917 GTG GAG GAG TAT GCG AAC TGC CAC CTG GCC AGA GCC CCG AAT CAC
1302 Val Glu Glu Tyr Ala Asn Cys His Leu Ala Arg Ala Pro Asn His

3962 GCT GTG GTC ACA CGG AAA GAT AAG GAA GCT TGC GTC CAC AAG ATA
1317 Ala Val Val Thr Arg Lys Asp Lys Glu Ala Cys Val His Lys Ile

4007 TTA CGT CAA CAG CAG CAC CTA TTT GGA AGC AAC GTA ACT GAC TGC
1332 Leu Arg Gln Gln Gln His Leu Phe Gly Ser Asn Val Thr Asp Cys

4052 TCG GGC AAC TTT TGT TTG TTC CGG TCG GAA ACC AAG GAC CTT CTG
1347 Ser Gly Asn Phe Cys Leu Phe Arg Ser Glu Thr Lys Asp Leu Leu

4097 TTC AGA GAT GAC ACA GTA TGT TTG GCC AAA CTT CAT GAC AGA AAC
1362 Phe Arg Asp Asp Thr Val Cys Leu Ala Lys Leu His Asp Arg Asn

4142 ACA TAT GAA AAA TAC TTA GGA GAA GAA TAT GTC AAG GCT GTT GGT
1377 Thr Tyr Glu Lys Tyr Leu Gly Glu Glu Tyr Val Lys Ala Val Gly

4187 AAC CTG AGA AAA TGC TCC ACC TCA TCA CTC CTG GAA GCC TGC ACT
1392 Asn Leu Arg Lys Cys Ser Thr Ser Ser Leu Leu Glu Ala Cys Thr

4232 TTC CGT AGA CCT TAAAATCTCAGAGGTAGGGCTGCCACCAAGGTGAAGATGGGAAC
1407 Phe Arg Arg Pro ···

4288 GCAGATGATCCATGAGTTTGCCCTGGTTTCACTGGCCCAAGTGGTTTGTGCTAACCACGT

4348 CTGTCTTCACAGCTCTGTGTTGCCATGTGTGCTGAACAAAAAATAAAAATTATTATTGAT

4408 TTTATATTTCGGGGGGGGGGCTGCAGCCCCTAGACCTGAGGGTCCCCACCTGGGACCCTT

4468 GAGAGTATCAGGTCTCCCACGTGGGAGACAAGAAATCCCTGTTTAATATTTAAACAGCAG

4528 TGTTCCCCATCTGGGTCCTTGCACCCCTCACTCTGGCCTCAGCCGACTGCACAGCGGCCC

4588 CTGCATCCCCTCTAGA
```

(SEQ ID NO:3)
(SEQ ID NO:4)

FIG. 5F

CHIMERIC PROTEIN BINDING TO LDL IS SENSITIVE TO EDTA AND pH

FIG. 8

CHIMERIC PROTEINS FOR USE IN TRANSPORT OF A SELECTED SUBSTANCE INTO CELLS

DESCRIPTION

Background of the Invention

The transport of molecules across cell membranes is an important component of the physiologic mechanisms that mediate homeostasis at the levels of the cell and the organism as a whole. Molecules that are used directly or indirectly in the assembly of cellular components are transported from the extracellular fluid into the cell, usually by the action of specific cell-surface receptors which bind to the selected substance and mediate its uptake into specific cell types. Many hormones, enzymes, and drugs which influence cellular activity are also transported into cells by specific cell-surface receptors. Furthermore, toxic molecules which are either produced in the body (i.e. through normal or defective metabolic pathways) or introduced by ingestion or exposure can be taken up and sequestered or metabolized by certain cells.

Removal of substances, both endogenously-produced and foreign substances, from extracellular fluids, such as blood or lymph, is often physiologically appropriate. However, in many instances, removal is impaired or occurs to a lesser extent than desirable and disease occurs. An example concerns LDL cholesterol, a naturally-occurring substance which must be removed at a controlled rate if abnormally elevated levels and the accompanying adverse effects are to be avoided. Hypercholesterolemia in humans is a condition characterized by elevated levels of total serum cholesterol. It is usually caused by an excess of low density lipoprotein (LDL) cholesterol or a deficiency of high density lipoprotein (HDL) cholesterol and often leads to atherosclerosis and coronary artery disease. LDL is continually formed in the blood from apolipoproteins produced by the liver. In order to maintain a steady-state level, LDL is removed from the blood at a rate equal to its formation. If LDL removal is impaired, the blood level of LDL increases and atherosclerosis is a greater risk. Atherosclerosis is by far the leading cause of death in the United States, accounting for over one-half of all deaths. (*Harrison's Principles of Internal Medicine*, Ed. J. D. Wilson et al., 12th ed., p. 995, McGraw-Hill, New York, 1991).

LDL particles carry approximately 60–70% of total serum cholesterol. LDL is a large spherical particle with an oily core composed of approximately 1500 cholesterol molecules, each of which is linked to a long-chain fatty acid by an ester linkage. Surrounding the core is a layer of phospholipid and unesterified cholesterol molecules, arranged in such a manner that the hydrophilic heads of the phospholipids are on the outside, and thus making it possible for the LDL to be dissolved in blood or intercellular fluid. Each LDL particle contains one molecule of Apolipoprotein B-100 (ApoB-100), a large protein molecule which is embedded in the hydrophilic coat of LDL. ApoB-100 is recognized and bound by the LDL receptor, which is present on the surfaces of cells. LDL bound to a LDL receptor is carried into the cell, in which the two are separated. The LDL receptor is recycled to the cell surface and the LDL is delivered to a lysosome. In the lysosome, LDL is processed to liberate unesterified cholesterol. The liberated cholesterol is incorporated into newly synthesized cellular membranes in all cells and, in specialized cells, is used for other purposes (e.g., steroid hormone synthesis, bile acid production).

The steady-state level of serum LDL is determined to a large extent by the number of functional hepatic LDL receptors (LDLRs), which play a central role in the removal of circulating LDL. (Brown, M. S. and Goldstein, J. L., *Science*, 232:34–47 (1986)) Individuals with familial hypercholesterolemia (FH) may be either heterozygous or homozygous for mutations leading to defective LDLRs and, as a result, these individuals have excess serum LDL. Other individuals who have elevated serum LDL levels may carry leaky or previously uncharacterized LDLR mutations or might be producing too much LDL due to elevated intake of dietary fat. Both FH and non-FH patients have elevated cardiovascular risk and could benefit from a therapy based on increasing the catabolism of LDL as a result of increased cellular uptake.

Thus, there exists a need to develop methods for increasing the uptake of selected substances into cells. These substances may be destined for catabolism as discussed above, or they may be designed to influence intracellular processes and thus be considered regulatory agents. Thus, cellular activity may be altered by introducing new regulatory agents which can alter specific intracellular processes into recipient cells. For example, cellular patterns of protein phosphorylation, expression of specific cellular genes, and cell growth properties may be altered by introduction of an appropriate regulatory agent into a cell. These regulatory agents may be proteins which have enzymatic activity or they may be proteins that bind specific cellular targets, targets which may be comprised of nucleic acid, protein, carbohydrate, lipid, or glycolipid.

SUMMARY OF THE INVENTION

Cell surface receptors provide a route for introducing selected substances into cells. The natural ligand of the receptor may be a portion of a chimeric protein in which the ligand domain is functionally linked to a protein domain that exerts a desired effect within a cell and is therapeutic in vivo. Alternatively, the protein domain may be bound to a selected substance which is to be removed from extracellular fluids for catabolism or other metabolic processing.

The present invention relates to chimeric proteins useful in transporting a selected substance present in extracellular fluids, such as blood or lymph, into cells; quantitative assays for the selected substance using chimeric proteins; DNA encoding the chimeric proteins; plasmids which contain DNA encoding the chimeric proteins; mammalian cells, modified to contain DNA encoding the chimeric proteins, which express and, optionally, secrete the chimeric proteins; a method of producing the chimeric proteins; a method of isolating the chimeric proteins; a method of using the chimeric proteins to assay the selected substance; and a method of reducing extracellular levels of the selected substance through administration of the chimeric protein, which results in transport of the selected substance into cells. The present invention also relates to a method of gene therapy, in which mammalian cells expressing and secreting the chimeric protein are implanted into an individual, in whom the chimeric protein is expressed and secreted and binds the selected substance. The resulting selected substance-chimeric protein complex is taken up into somatic cells and, as a result, the extracellular levels of the selected substance are reduced.

The selected substance can be a normally-occurring (endogenously produced) constituent of the blood, such as a nutrient, metabolite, naturally-occurring hormone or lipoprotein, or a foreign constituent, such as a pathogen, toxin, environmental contaminant or drug or pharmacologic agent. In either case, the selected substance is removed from the extracellular fluid, such as blood or lymph, by means of a chimeric protein which selectively binds the selected substance and also binds a cell surface receptor present on one or more types of somatic cells, particularly human somatic cells. The resulting chimeric protein-selected substance complex binds to the cell surface receptor and is transported into the cell, where it is sequestered or metabolized, resulting in reduced extracellular levels of the selected substance.

Chimeric proteins of the present invention include at least two components: a functional domain and a carrier domain. The functional domain comprises an amino acid (polypeptide) sequence which binds the selected substance to be transported into cells or contains a sequence which will affect the target cell in a specific way. The carrier domain comprises an amino acid (polypeptide) sequence which binds a cell surface receptor present on one or more types of somatic cells. The amino acid sequence which is the functional domain can be a ligand binding domain of the selected substance; the amino acid sequence which is the carrier domain can bind to a cell-surface receptor and is thus a cell surface receptor ligand. Both the functional and carrier domains may be modified post-translationally, for example, by glycosylation at certain sites. In the case in which the selected substance is a normally-occurring constituent of the blood, lymph, or extracellular fluid, the ligand-binding domain which binds the selected substance is an amino acid sequence which normally binds the selected substance (i.e., binds the selected substance in humans), a modified form of such a sequence with altered binding properties, or an amino acid sequence which is not usually found in humans but has been produced by synthetic or genetic engineering methods and binds the selected substance. For example, the functional and/or carrier domains may be amino acid sequences selected from a combinatorial peptide library or phage display library. The functional and/or carrier domains may also comprise the antigen binding domain of an immunoglobulin or single-chain antibody, wherein the antigen binding domain of the immunoglobulin or single-chain antibody recognizes the desired selected substance or cell surface receptor. In the case in which the selected substance is a foreign constituent, the amino acid sequence which binds the selected substance is one selected from naturally-occurring ligand-binding domains which bind the foreign constituent or an amino acid sequence designed to bind the foreign constituent. The amino acid sequence which binds the cell surface receptor typically binds a cell surface receptor other than the receptor to which the selected substance normally binds. Thus, the method causes a selected substance to enter a cell by a route which is different from that which it normally takes in an organism.

The domains of the chimeric protein can be linked in a variety of configurations, as long as the resulting chimeric protein is able to bind both the selected substance and the cell surface receptor. Typically, the two domains are encoded by a single reading frame in a recombinant DNA molecule, and the two domains are linked by a peptide bond. The two domains may be separated by one or more amino acids also encoded by the open reading frame. Alternatively, the two domains may be expressed from separate DNA molecules and become linked in vitro or in vivo through either non-covalent (e.g., hydrophobic or ionic interaction) or covalent (e.g., disulfide) linkage.

Once the selected substance is bound to the ligand binding domain of the chimeric protein, the resulting complex is referred to as the selected substance-chimeric protein complex. The cell surface receptor ligand present in the selected substance-chimeric protein complex binds to its cell surface receptor and the complex is transported into the cell (e.g., by endocytosis), thus reducing circulating levels of the selected substance.

In one embodiment, the present invention relates to chimeric proteins useful in transporting LDL into cells; pharmaceutical compositions containing chimeric proteins; assays for LDL using the chimeric proteins; DNA encoding the chimeric proteins; plasmids which contain DNA encoding the chimeric proteins; mammalian cells, modified to contain DNA encoding the chimeric proteins, which express and, optionally, secrete the proteins (genetically modified cells); a method of producing the chimeric proteins; a method of isolating the chimeric proteins; a method of using the chimeric proteins to assay LDL and a method of reducing extracellular levels of LDL cholesterol (LDL) by administering a chimeric protein which transports LDL into cells.

In one embodiment of reducing extracellular LDL levels, a chimeric protein which binds LDL and a cell surface receptor other than LDL receptor (LDLR) is administered to a human patient in whom serum cholesterol level is to be reduced. In another embodiment of reducing extracellular LDL levels, cells modified to contain DNA which encodes the chimeric protein, are implanted into an individual. In the individual, the chimeric protein is expressed in and secreted by the genetically modified cells, binds LDL in the blood and forms LDL-chimeric protein complexes, which are transported into non-genetically modified cells, thus reducing serum LDL cholesterol levels.

Chimeric proteins of the present invention useful for LDL transport and for assaying LDL in a sample include at least two components: a functional domain, which comprises the amino acid sequence of the ligand-binding domain of the LDLR and a carrier domain, which comprises an amino acid sequence which binds a cell surface receptor other than the LDLR on one or more types of somatic cells, particularly human somatic cells. In one embodiment of the chimeric protein useful for increasing uptake of LDL into cells, an amino-terminal sequence comprising the ligand binding domain (i.e., the LDL binding domain) of the LDLR is joined to a C-terminal sequence comprising a cell surface receptor ligand. The carboxy-terminus of the LDL binding domain is joined to the amino-terminus of the cell surface receptor ligand domain.

In one embodiment of the chimeric protein, the two components are the ligand-binding domain of the human LDLR and human transferrin; the LDL binding domain of the LDLR is joined to the amino-terminus of the mature human transferrin polypeptide. This chimeric protein can bind both LDL and the transferrin receptor. Once bound to the transferrin receptor on the surface of a cell, such as a liver cell, the chimeric protein and the LDL bound to the chimeric protein LDLR component are endocytosed by transferrin receptor-mediated endocytosis, with the result that LDL enters the cell and the extracellular LDL concentration is reduced. The transferrin receptor is present on a wide variety of mammalian cell types, allowing the chimeric protein to promote LDL uptake in a wide variety of mammalian cells.

In a second embodiment, the chimeric protein comprises a functional domain which is a ligand-binding domain of LDLR, and a carrier domain which is an amino acid sequence which binds a cell surface receptor other than the transferrin receptor, such as the serum albumin receptor, asialoglycoprotein receptor, an adenovirus receptor, a retrovirus receptor, CD4, lipoprotein (a), immunoglobulin Fc receptor, a-fetoprotein receptor, LDLR-like protein (LRP) receptor, acetylated LDL receptor, mannose receptor, or mannose-6-phosphate receptor. In general, an amino acid sequence that binds to any receptor which can bind and internalize bound ligand may be used. These chimeric proteins bind both LDL and a cell surface receptor and can be used to enhance the uptake of LDL into a wide variety of cells. Once bound to the receptor, the chimeric protein-LDL complex is endocytosed with the result that the LDL enters the cell and the extracellular LDL concentration is reduced.

A chimeric protein of the present invention is produced by an appropriate mammalian cell which contains DNA encoding the chimeric protein. Modified mammalian cells of the present invention (i.e., mammalian cells modified to contain nucleic acid encoding a chimeric protein of the present invention) include mammalian cells which are stably or transiently transfected or infected with a plasmid, nucleic acid fragment, or other vector, including a viral vector, comprising DNA or RNA encoding the chimeric protein or which are derived (directly or indirectly) from a progenitor modified mammalian cell which contains DNA or RNA (e.g., plasmid, nucleic acid fragment, or other vector comprising DNA or RNA) encoding the chimeric protein.

In one embodiment of the present method of producing chimeric proteins, the mammalian cell used is a cell line, such as a Chinese hamster ovary (CHO) cell line, which contains and expresses DNA which encodes the chimeric protein. Optionally, the chimeric protein is secreted into the medium in which the transfected CHO cells are cultured. In a second embodiment of the present method of producing chimeric proteins, the modified mammalian host cell is a primary or secondary cell, such as a primary or secondary human fibroblast, transfected or infected with DNA encoding the chimeric protein. The modified cell (e.g., a transfected or infected primary or secondary human fibroblast) expresses the encoded chimeric protein and, optionally, secretes it into the culture medium. Alternatively, the transfected or infected primary or secondary cells may be implanted into an individual, such as a human, in whom the chimeric protein is secreted for therapeutic purposes.

The chimeric protein produced by cultured modified cells may be isolated from cell lysates or the culture medium by any appropriate method. One such method, described herein, is based on affinity chromatography in which the chimeric protein is isolated by first binding to an antibody column prepared using an antibody directed against the cell surface receptor ligand, eluting, and subsequently by binding to a column bearing the selected substance to which the ligand binding domain of the chimeric protein binds. For example, the chimeric protein which binds LDL and the cell surface receptor for transferrin can be isolated by first being separated by binding to an anti-transferrin antibody column, and subsequently by binding to LDL bound to an anti-LDL antibody column. As a result of the isolation method, purified intact chimeric protein is obtained. Alternatively, in the first separation step, the chimeric protein is bound to a column bearing the selected substance to which the ligand binding domain of the chimeric protein binds and in the second separation step, is bound to a column bearing an antibody directed against the cell surface receptor ligand. As described herein, chimeric protein which includes domains from both LDLR and transferrin has been purified.

The chimeric protein of the present invention is useful to transport the selected substance, LDL, into cells, such as liver cells, thus reducing extracellular levels of the LDL. This has clinical or therapeutic applications, such as in controlling or lowering serum LDL levels in humans, such as hypercholesterolemic individuals. In one embodiment of the method of the present invention in which LDL is transported into cells through the use of the chimeric protein, cells expressing the chimeric protein are implanted in an individual in whom serum LDL levels are to be lowered. In the individual, the cells produce the chimeric protein, which enters the interstitial fluid. From the interstitium the chimeric protein can enter the lymphatics and ultimately, the bloodstream, where it binds LDL resulting in formation of a chimeric protein-LDL complex. The complex passes (e.g., via the bloodstream) to a cell which bears a transferrin receptor (e.g., a hepatocyte), and is bound to the cell as a result of the transferrin domain-transferrin receptor interaction. The chimeric protein-LDL complex is taken up by means of the transferrin receptor-mediated endocytosis pathway that normally functions to internalize transferrin. In another embodiment of the method, purified or partially purified chimeric protein is administered to an individual (particularly a human) in whom increased LDL transport into cells is desired.

The chimeric protein has a wide variety of other clinical or therapeutic applications, such as in reducing the circulating levels of normal or abnormal endogenously produced metabolites or nutrients (e.g. acetylated low density lipoprotein, apolipoprotein E4, tumor necrosis factor a, transforming growth factor $\beta$, a cytokine, an immunoglobulin, a hormone, glucose, a bile salt, a glycolipid [such as glucocerebroside which accumulates in patients with Gaucher disease or ceramidetrihexoside which accumulates in patients with Fabry disease], or a glycosaminoglycan [such as those that accumulate in patients with Hunter, Hurler, or Sly syndromes]) or of foreign substances (e.g., pathogens, environmental contaminants, or alcohol).

The chimeric protein of the present invention is also useful to assay, particularly to quantitatively assay, the selected substance to which the ligand binding domain binds. For example, it may be used in an assay to determine levels of LDL, immunoglobulins, growth hormone, and Apolipoprotein E in the blood. For example, the chimeric protein can be used as a component in known methods, such as an enzyme-linked assay, to assay a selected substance.

BRIEF DESCRIPTION OF THE DRAWINGS

FIGS. 3A–3E are the nucleotide sequence (SEQ ID NO: 15 1) and corresponding amino acid sequence (SEQ ID NO: 2) for the chimeric cDNA in pEFBOS/LDLrTF1.S, in which the initiating methionine is indicated as the first amino acid of the fusion protein; . . . indicates the termination (stop) codon; the underlined codons denote the human transferrin portion of the chimeric protein; the codons not underlined denote the LDLR portion of the chimeric protein, nucleotides 1–13: 5' non-coding LDLR sequences; nucleotides 3236–3428:3' non-coding transferrin sequences.

FIGS. 5A–5F are the nucleotide (SEQ ID NO: 3) and corresponding amino acid sequence (SEQ ID NO: 4) for the chimeric cDNA in pEFBOS-LDLR/TF1-710, in which the initiating methionine is indicated as the first amino acid of the fusion protein; . . . indicates the termination (stop) codon; the underlined codons denote the human transferrin portion of the chimeric protein; the codons not underlined denote the LDLR portion of the chimeric protein; nucleotides 1–13: 5' non-coding LDLR sequences and nucleotides 4244–4603: 3' non-coding transferrin sequences are shown.

FIG. 8 is a graphic representation of results of a microplate binding analysis of chimeric protein binding to LDL.

DETAILED DESCRIPTION OF THE INVENTION

Figure 1:
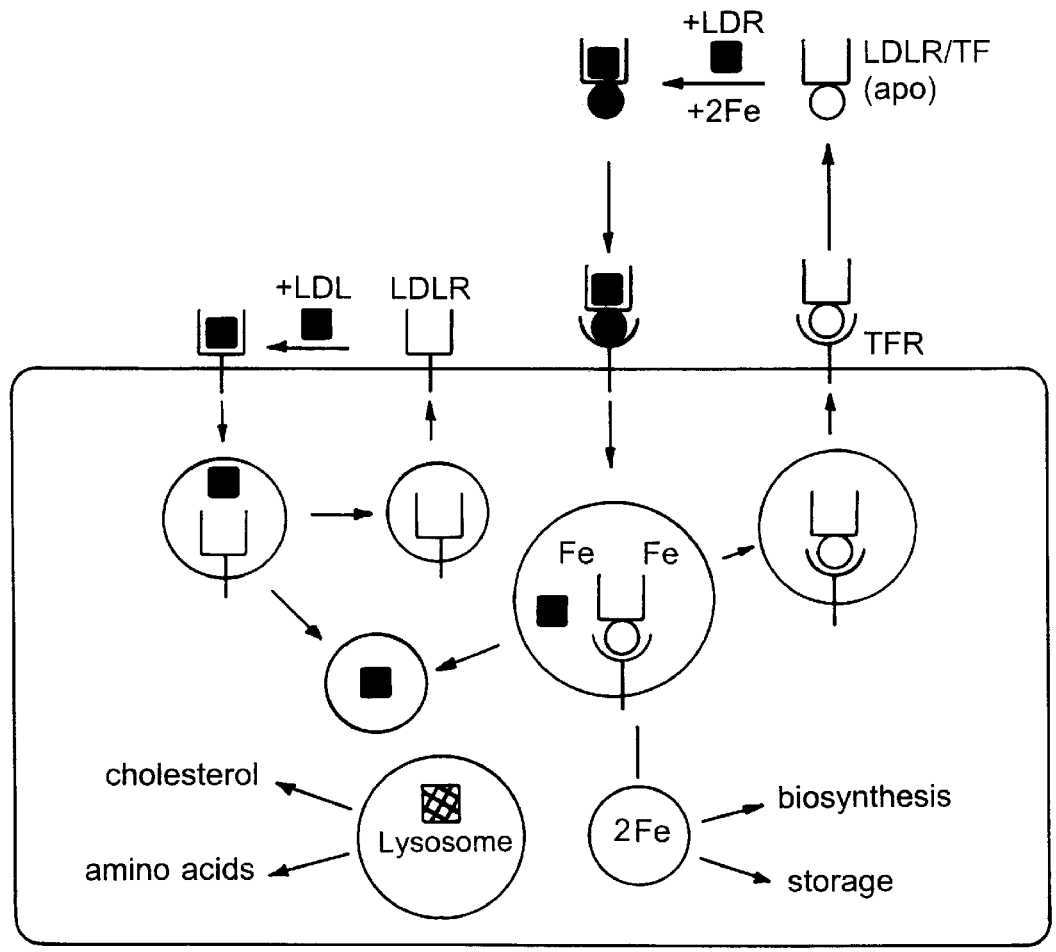
FIG. 1 is a schematic representation of LDL uptake via the normal LDL receptor-mediated pathway (LDLR pathway) and the transferrin receptor-mediated pathway (TFR pathway).

The present invention exemplifies methods for introducing selected substances into cells for in vivo therapy. Further, the invention teaches the use of gene therapy to produce therapeutic proteins designed to transport selected substances into cells.

As described herein, Applicants have developed a new strategy for uptake of a selected substance into cells through the use of a chimeric protein and by means of a mechanism by which the selected substance is not normally taken up in cells. The chimeric protein binds the selected substance and also binds a cell surface receptor present on somatic cells, particularly on human somatic cells. Binding of the chimeric protein and the selected substance results in formation of a chimeric protein-selected substance complex, which is bound by the cell surface receptor and transported into the cell bearing the receptor. The selected substance can be a normally-occurring (endogenously produced) constituent of extracellular fluid, such as blood or lymph, or a foreign constituent such as a drug or a toxin. The chimeric protein of the present invention is itself delivered or administered to an individual or is provided to an individual by a gene therapy method in which cells which express and secrete the chimeric protein are introduced into an individual, in whom the chimeric protein is produced and secreted. The chimeric protein selectively binds the selected substance in the extracellular fluid (e.g., blood, lymph) of the individual, thus producing a selected substance-chimeric protein complex. The ligand-binding domain of the complex is bound by cell surface receptors on somatic cells in the individual. The complex is transported into the cell to which it is bound and the extracellular level of the selected substance is, thus, reduced.

Chimeric Proteins for Reducing Serum LDL Levels

In one embodiment, Applicants have developed a new strategy for uptake of human LDL which does not normally occur in humans, circumvents the defective LDLR or supplements the reduced level of LDLR known to occur in individuals with familial hypercholesterolemia, and augments or increases the ability of cells (those with a normal number of functional LDLRs and those with abnormal numbers of LDLRs) to take up LDL. This new method enhances LDL transport into liver cells, whether they have an abnormal number of functional LDLRs or a normal number of functional LDLRs. Applicants have determined that a receptor which is present on human cell surface membranes can be used as a means by which LDL can be transported into cells, such as liver cells. Cell surface receptors, such as the transferrin receptor, the serum albumin receptor, the asialoglycoprotein receptor, an adenovirus receptor, a retrovirus receptor, CD4, lipoprotein (a) receptor, immunoglobulin Fc receptor, a-fetoprotein receptor, LDLR-like protein (LRP) receptor, acetylated LDL receptor, mannose receptor, or mannose-6-phosphate receptor, can be used as a means by which LDL can be transported into cells. These receptors are present, respectively, on a wide variety of different cell types and allow uptake of LDL into a wide variety of cell types.

Applicants have produced chimeric proteins useful for transport of LDL into cells. These chimeric proteins are the subject of the present invention, as are nucleic acid sequences encoding the chimeric proteins; mammalian host cells containing DNA (or RNA) encoding the chimeric proteins, which is expressed in the cells; a method of producing the chimeric proteins; a method of isolating the chimeric proteins, a method in which the chimeric proteins are used to quantitatively assay for LDL, and a method of reducing extracellular LDL levels, including a therapeutic method of reducing serum LDL levels in an individual. In the therapeutic method, a chimeric protein which binds LDL and a human cell surface receptor other than the human LDLR is provided to an individual, either by administration of the chimeric protein itself or by administration (e.g., implantation) of cells which express and secrete the chimeric protein. In either case, the chimeric protein binds LDL and a human cell surface receptor and the complex is transported into the cell to which it is bound, reducing extracellular levels of LDL.

In one embodiment, the chimeric protein comprises a first domain, which is the ligand-binding domain of the LDLR and a second domain, which is transferrin (TF). The human transferrin receptor has a very high affinity for its ligand; the equilibrium dissociation constant (Kd) is 2–7 nM (Trowbridge, I.S. et al., *Biochem. Pharmacol.*, 33:925–993 (1984)). Transferrin can be bound to its receptor even when the transferrin concentration is very low in comparison with total blood protein concentration. Similarly, the LDL receptor has a high affinity for its ligand (Kd=7.2 nM for liver receptors (Krampler, F. et al., *J. Clin. Invest.*, 80:401–408 (1987) and 2.8 nM for fibroblast receptors (Innerarity, T. L. et al., *Meth. Enzymol.*, 129:542–565 (1986)). Thus, the chimeric protein of this embodiment has a high affinity for the two components (human LDL and the human transferrin receptor) which must be brought together for LDL to be transported into cells by transferrin receptor-mediated endocytosis. A diagram of how an LDLR-transferrin (LDLR/TF) chimeric protein functions to promote LDL uptake via the transferrin receptor is shown in FIG. 1. LDL taken up by either pathway is metabolized to release cholesterol and free amino acids. In the LDLR-pathway, LDLR is recycled to the cell surface after LDL is released. In the TFR pathway, LDL is released and the TFR and LDLR/TF chimeric protein are recycled to the cell surface.

The entire human transferrin protein can be present in the chimeric protein; alternatively, only the portions of human transferrin necessary for binding to iron and the human transferrin receptor present on human cells are included in the chimeric protein. At neutral pH, each TFR binds two diferric (i.e., iron-saturated) TF molecules. The binding site is in the N-terminal domain of each TF. Monoferric TF binds TFR less readily, while apoTF (i.e., TF without bound iron) fails to bind TFR. In contrast, when iron is released in the acidic environment of the lysosome, ApoTF remains bound to TFR in order for recycling of the receptor and apoTF to the cell surface. As used herein, the term "human transferrin" refers to the entire human transferrin molecule or those segments of the protein necessary for binding to iron and to transferrin receptors on human cell surface membranes.

In one embodiment, the ligand-binding domain of the human LDL receptor is joined to human transferrin at the N-terminus of the mature TF molecule. The ligand-binding domain may include other LDL receptor regions which are present in the naturally-occurring receptor protein.

Production of Chimeric Proteins

The chimeric protein of the present invention, such as the chimeric protein for transporting LDL into cells, can be produced using host cells expressing a single nucleic acid encoding the entire chimeric protein or more than one nucleic acid sequence, each encoding a domain of the chimeric protein and, optionally, an amino acid or amino acids which will serve to link the domains. The chimeric proteins can also be produced by chemical synthesis.

A. Host Cells

Host cells used to produce chimeric proteins are bacterial, yeast, insect, non-mammalian vertebrate, or mammalian cells; the mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types.

Cells which contain and express DNA or RNA encoding the chimeric protein are referred to herein as genetically modified cells. Mammalian cells which contain and express DNA or RNA encoding the chimeric protein are referred to as genetically modified mammalian cells. Introduction of the DNA or RNA into cells is by a known transfection method, such as electroporation, microinjection, microprojectile bombardment, calcium phosphate precipitation, modified calcium phosphate precipitation, cationic lipid treatment, photoporation, fusion methodologies, receptor mediated transfer, or polybrene precipitation. Alternatively, the DNA or RNA can be introduced by infection with a viral vector. Methods of producing cells, including mammalian cells, which express DNA or RNA encoding a chimeric protein are described in co-pending patent applications U.S. Ser. No. 08/334,797, entitled "In Vivo Protein Production and Delivery System for Gene Therapy", by Richard F Selden, Douglas A. Treco and Michael W. Heartlein (filed Nov. 4, 1994); U.S. Ser. No. 08/334,455, entitled "In Vivo Production and Delivery of Erythropoietin or Insulinotropin for Gene Therapy", by Richard F Selden, Douglas A. Treco and Michael W. Heartlein (filed Nov. 4, 1994) and U.S. Ser. No. 08/231,439, entitled "Targeted Introduction of DNA Into Primary or Secondary Cells and Their Use for Gene Therapy", by Douglas A. Treco, Michael W. Heartlein and Richard F Selden (filed Apr. 20, 1994). The teachings of each of these applications are expressly incorporated herein by reference.

B. Nucleic Acid Constructs

A nucleic acid construct used to express the chimeric protein can be one which is expressed extrachromosomally (episomally) in the transfected mammalian cell or one which integrates, either randomly or at a pre-selected targeted site through homologous recombination, into the recipient cell's genome. A construct which is expressed extrachromosomally comprises, in addition to chimeric protein-encoding sequences, sequences sufficient for expression of the protein in the cells and, optionally, for replication of the construct. It typically includes a promoter, chimeric protein-encoding DNA and a polyadenylation site. The DNA encoding the chimeric protein is positioned in the construct in such a manner that its expression is under the control of the promoter. Optionally, the construct may contain additional components such as one or more of the following: a splice site, an enhancer sequence, a selectable marker gene under the control of an appropriate promoter, and an amplifiable marker gene under the control of an appropriate promoter.

In those embodiments in which the DNA construct integrates into the cell's genome, it need include only the chimeric protein-encoding nucleic acid sequences. Optionally, it can include a promoter and an enhancer sequence, a polyadenylation site or sites, a splice site or sites, nucleic acid sequences which encode a selectable marker or markers, nucleic acid sequences which encode an amplifiable marker and/or DNA homologous to genomic DNA in the recipient cell to target integration of the DNA to a selected site in the genome (targeting DNA or DNA sequences).

C. Cell Culture Methods

Mammalian cells containing the chimeric protein-encoding DNA or RNA are cultured under conditions appropriate for growth of the cells and expression of the DNA or RNA. Those cells which express the chimeric protein can be identified, using known methods and methods described herein, and the chimeric protein isolated and purified, using known methods and methods also described herein, either with or without amplification of chimeric protein production. Identification can be carried out, for example, through screening genetically modified mammalian cells displaying a phenotype indicative of the presence of DNA or RNA encoding the chimeric protein, such as PCR screening, screening by Southern blot analysis, or screening for the expression of the chimeric protein. Selection of cells having incorporated chimeric protein-encoding DNA may be accomplished by including a selectable marker in the DNA construct and culturing transfected or infected cells containing a selectable marker gene under conditions appropriate for survival of only those cells which express the selectable marker gene. Further amplification of the introduced DNA construct can be effected by culturing genetically modified mammalian cells under conditions appropriate for amplification (e.g., culturing genetically modified mammalian cells containing an amplifiable marker gene in the presence of a concentration of a drug at which only cells containing multiple copies of the amplifiable marker gene can survive).

Genetically modified mammalian cells expressing the chimeric protein can be identified, as described herein, by detection of the expression product. For example, mammalian cells expressing chimeric protein in which the second domain is transferrin can be identified by a sandwich enzyme immunoassay in which the chimeric protein is captured on a microtiter plate by binding to a monoclonal antibody specific for the LDL binding domain, and the bound chimeric protein is detected by binding to an anti-human TF monoclonal antibody specific for the human TF domain. Routine assay for the level of chimeric protein in most genetically modified mammalian cell types that otherwise do not synthesize human TF can be performed by an ELISA which detects human TF (Example 6), as each chimeric protein expressed contains an assayable TF domain. Alternatively, mammalian cells expressing the chimeric protein can be identified by an LDL binding assay (Example 9). Further, they can be identified using other methods known to one of ordinary skill in the art. (Sambrook, J. et al., *Molecular Cloning; a Laboratory Manual*, 2d ed., Cold Spring Harbor Laboratory Press, New York, 1989; Ausubel, F. A. et al., eds., *Current Protocols in Molecular Biology*, Wiley, New York, 1994.

D. Purification of Chimeric Proteins

The chimeric protein produced by genetically modified mammalian cells can be isolated from the cells and purified or partially purified using methods known to those of skill in the art as well as by methods described herein. As described in Example 7, chimeric protein has been obtained, from cells in which it was expressed, through a method based on direct binding to both domains of the chimeric protein. The method includes two steps: one involving immunoaffinity binding to the transferrin epitope involved in transferrin receptor binding and another involving ligand (LDL) affinity binding to the LDLR domain. To purify LDLR ligand-binding domain transferrin chimeric protein, the method was carried out as follows: Medium in which cells expressing the chimeric protein were cultured is separated from the cells and, generally, concentrated by tangential flow ultrafiltration. The resulting culture medium, which is enriched or concentrated for the chimeric protein, is contacted with an anti-human transferrin monoclonal antibody (anti-TF MAb) bound to a column matrix, which results in binding of all proteins in the medium which contain a transferrin epitope. The bound protein is eluted from the immunoaffinity column and the resulting immunoaffinity purified chimeric protein is subsequently subjected to a ligand-affinity purification step, in which it is contacted with LDL indirectly bound to a column matrix through an anti-LDL antibody fixed to the column matrix, under conditions appropriate for LDL-LDLR binding. As a result, chimeric protein containing transferrin and an intact LDLR ligand binding domain is bound to LDL; the chimeric protein is eluted from the column to yield a highly purified preparation of the chimeric protein. As demonstrated in Example 7, this process resulted in separation of intact chimeric protein which contains transferrin and binds LDL. The method can be modified to purify chimeric proteins in which the first domain is a ligand binding domain other than the LDLR ligand binding domain and the second domain is a cell surface receptor ligand other than transferrin.

In one embodiment of the present method of purifying chimeric protein comprising intact LDLR binding domain and transferrin, the purification is carried out as follows: Culture medium from host cells expressing the chimeric protein is separated from the host cells and concentrated by tangential-flow ultrafiltration using a membrane with a molecular weight cut off of 100,000 daltons. In one experiment, the culture medium is concentrated approximately 32-fold.

An anti-TF MAb is (e.g., HTF-14, Biodesign, Kennebunk, ME, isolated from ascites fluid as described in Example 7) bound to a solid support, such as polystyrene beads (e.g., cyanogen-bromide [CNBr]—activated Sepharose 4B), to form an immunoaffinity column. The concentrated culture medium is contacted with the solid-support-bound anti-TF MAb, by loading the medium onto an HTF-14 immunoaffinity column, and maintained in contact with the anti-TF MAb under appropriate conditions and for sufficient time for the transferrin domain in the chimeric protein in the medium to bind to the anti-TF MAb (i.e., for the chimeric protein to bind to MTF-14 through an interaction with the chimeric protein's transferrin domain). As a result, chimeric protein containing transferrin is non-covalently bound to the solid support (e.g., to beads to which HTF-14 is bound). The solid support-bound chimeric protein is subjected to appropriate conditions (e.g., washing with 0.1M glycine, pH 2.3) to elute the chimeric protein, which is collected.

In the embodiment described in Example 7, the HTF-14 immunoaffinity column containing bound chimeric protein was washed with 0.1M Tris-HCl, 0.15M NaCl, pH 7.4 (TBS), and then eluted with 0.1M glycine pH 2.3. Two milliliter fractions were collected into buffer of appropriate pH to neutralize the elution buffer and certain of the fractions were pooled. Analysis showed that this step resulted in an approximately 8,000-fold purification of chimeric protein from the concentrated culture media. The resulting immunoaffinity purified chimeric protein was a mixture which contained, as described in Example 7, chimeric protein which includes transferrin and intact LDLR binding domains and chimeric protein which had been degraded by a serine protease and, thus, did not include intact LDLR binding domain. The second step in the purification process is a ligand-affinity (LDL-affinity) based step which results in separation of chimeric protein which comprises transferrin and intact LDLR binding domain from the chimeric protein which does not include intact LDLR binding domain. In this step, the immunoaffinity purified chimeric protein mixture was loaded onto a ligand affinity column containing CNBr activated Sepharose beads to which human LDL (hLDL) was bound (e.g., by means of polyclonal rabbit anti-human LDL antibody immobilized on the beads). The immunoaffinity purified chimeric protein was loaded onto the anti-LDL (LDL) ligand affinity column for sufficient time and under appropriate conditions for LDL on the beads and LDLR in the chimeric protein to bind, producing chimeric protein non-covalently bound to the column. The column was washed with TBS and eluted with 20 mM EDTA in TBS, pH 7.4. Fractions were collected and assayed, and fractions 2 and 3 were shown to contain the peak concentrations of the protein.

E. In Vitro Characterization of Chimeric Proteins

Analysis of chimeric protein produced as described herein (see Example 10) showed that it binds LDL in a divalent cation-dependent manner, which is a well-established property of the LDL-LDLR binding interaction. Further analysis showed that binding of the chimeric protein to LDL did not occur in acidic buffer conditions and that EDTA and acidic buffer were each effective in dissociating chimeric protein bound to LDL (Example 10). It is also a well-established property of the LDL-LDLR binding interaction that LDL is released from LDLR in vivo in the acidic endosomal compartment. This suggests that the chimeric protein may be able to act in a similar way in cells, which would result in release of the LDL from the chimeric protein in the cell. Taken together, these findings support the function of the chimeric protein with respect to binding to serum LDL and uptake into cells for further metabolism.

Additional analysis (Example 9) demonstrated that half-maximal binding occurs at an LDL concentration of approximately 3 nM, which is comparable to that of purified LDLR in a solid-phase binding assay (Innerarity, T. L. et al., *Meth. Enzymol.*, 129:542–565 (1986)) as well as to the published $K_d$ value for the dissociation of LDL from LDLR in human fibroblast cells. This supports the idea that the chimeric protein has a binding affinity for LDL which is comparable to the binding affinity of full-length, plasma membrane-bound LDLR for LDL.

The functional activity of chimeric protein in which the first domain is the ligand-binding domain of LDLR and the second domain is transferrin is assessed as described in Examples 11, 13 and 14. To determine whether chimeric protein can result in cellular uptake of LDL via the transferrin receptor, a hepatic cell line, such as HepG2, is used. As described in Example 13, hepatic cells and LDL in vitro are exposed to chimeric protein and LDL. To determine whether chimeric protein can bind human LDL in culture medium and mediate uptake into hepatic cells via the transferrin receptor, the ability of unlabeled LDL or unlabeled transferrin to inhibit cellular uptake of labeled LDL (e.g., $^{125}$I-LDL) in the presence of chimeric protein is assessed, as described in Example 13. Whether LDL taken up by the transferrin receptor is metabolized to a cholesterol pool can be assessed as described in Example 13. For example, inhibition of cholesterol biosynthesis as a result of LDL uptake can be assessed by determining production of an enzyme, such as 3-hydroxy-3-methylglutaryl coenzyme A reductase (HMG CoA reductase), which is down-regulated (inhibited) by an oversupply of cholesterol in a cell. Alternatively, determination of levels or activity of an enzyme, such as acyl-coenzyme A cholesterol acyltransferase (ACAT), which increases in response to increased cholesterol in cells, can be used to assess whether LDL is taken up by the transferrin receptor and metabolized to cholesterol. Increased ACAT activity is indicative of increased cholesterol levels in the cell.

F. In Vivo Characterization of Chimeric Proteins

The anti-hypercholesterolemic effect of the chimeric protein can be assessed, as described in Example 14. Briefly, chimeric protein is administered in an animal model system for human familial hypercholesterolemia, such as the LDLR-knockout mouse or the Watanabe rabbit, and its effect on serum cholesterol levels is determined. A decrease in serum cholesterol levels after administration of an appropriate amount of chimeric protein to an LDLR-knockout mouse or a Watanabe rabbit is indicative of the ability of the chimeric protein to transport cholesterol into cells.

G. Therapeutic Use of Chimeric Proteins

Chimeric proteins of the present invention are useful to enhance LDL transport into cells, such as hepatic cells. Chimeric proteins, such as those with the LDLR-ligand-binding domain fused to a transferrin domain, can be administered to an individual in whom LDL metabolism is to be enhanced. Chimeric proteins are administered in an appropriate carrier, which can be physiologic saline or water or mixed with stabilizers or excipients, such as albumin or low molecular weight sugars. They are administered using known techniques and by a variety of routes, such as by intramuscular, intravenous, intraperitoneal injection. Alternatively, genetically modified mammalian cells expressing chimeric protein can be implanted in an individual. Non-immortalized cells (primary or secondary cells) and/or immortalized cells can be transfected. These include, but are not limited to fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types.

Immortalized cells can also be transfected by the present method and used for either protein production or gene therapy. Examples of immortalized human cell lines useful for protein production or gene therapy by the present method include, but are not limited to, HT1080, HeLa, MCF-7 breast cancer cells, K-562 leukemia cells, KB carcinoma cells, 2780AD ovarian carcinoma cells, Raji (ATCC CCL 86) cells, Jurkat (ATCC TIB 152) cells, Namalwa (ATCC CRL 1432) cells, HL-60 (ATCC CCL 240) cells, Daudi (ATCC CCL 213) cells, RPMI 10 8226 (ATCC CCL 155) cells and MOLT-4 (ATCC CRL 1582) cells. In cases where genetically modified immortalized cells are used for gene therapy, the cells may be enclosed within a semi-permeable barrier device which allows for the diffusion of the chimeric protein out of the device.

Preferably, cells (e.g., fibroblasts) to be used in the gene therapy method of the present invention are obtained from the individual to be treated. The cells are modified by introduction of a DNA construct of the present invention, such as a DNA construct encoding a chimeric protein in which domain 1 is the ligand-binding domain of human LDLR and domain 2 is comprised of an amino acid sequence derived from transferrin. The resulting genetically modified cells are expanded in culture and introduced into the individual. Cells expressing a DNA construct encoding such a chimeric protein can be produced as described in co-pending U.S. patent application Ser. No. 07/787,840, entitled "In Vivo Protein Production and Delivery System for Gene Therapy", by Richard F Selden, Douglas A. Treco and Michael W. Heartlein (filed Nov. 5, 1991), the teachings of which are incorporated herein by reference. The cells express and secrete the chimeric protein, which binds LDL and transports it to cells bearing transferrin receptors on their surfaces. Transferrin receptor-mediated endocytosis of the chimeric protein-LDL complex would result in introduction of LDL into cells and lowering of extracellular LDL levels. DNA encoding a chimeric protein in which the second domain is a cell surface receptor ligand other than transferrin, such as those listed above, can be introduced into mammalian cells. Genetically modified mammalian host cells which express and secrete the chimeric protein can be implanted in an individual, in whom the chimeric protein binds LDL. The resulting chimeric protein-LDL complex is bound to cells bearing the receptor for which the amino acid sequence of the second domain is a ligand and, through receptor-mediated endocytosis, enters the cells. Thus, circulating LDL levels would be reduced.

The number of genetically modified mammalian host cells implanted in an individual is determined by the amount of chimeric protein to be delivered and the level of its expression by the cells. The amount needed by an individual will depend on considerations such as age, body size, sex, serum LDL level, and serum half-life of the chimeric protein. The required dose can be determined empirically or calculated based on the pharmacodynamic properties established for the chimeric protein.

Other, related, chimeric proteins can be used to clear oxidized LDL, which represents a clinically significant fraction of the total LDL, from the blood. The early stages of atherosclerotic plaque formation are believed to occur when high levels of circulating LDL interact with endothelial cells in blood vessels, where oxidation of amine groups (e.g. on lysine and arginine residues ) on apoB-100 takes place by free radical attack. Oxidation (including acetylation) of apoB-100 in LDL particles is known to result in loss of affinity for the LDL receptor. Oxidized LDL is not cleared by the liver, but instead accumulates in the circulation until it can interact with the scavenger receptor (AcLDLR; previously known as the Acetyl LDL Receptor), which is predominantly found on macrophages. Macrophages taking up large quantities of oxidized LDL become bloated with lipid vacuoles and are known as "foam cells". Foam cells with cell-surface determinants for adhesion to endothelium are believed to play a role in the early development of atherosclerotic plaques and indeed are found in plaques at various stages.

A chimeric protein containing a scavenger receptor ligand-binding domain fused to human transferrin (AcLDLR/TF) is therapeutically useful by binding to and removing oxidized LDL via transferrin receptors in the liver. In addition, since the chimeric protein can be supplied at high concentration, it can function as a competitor of the macrophage AcLDLR, such that most oxidized LDL will be bound to AcLDLR/TF, rather than bound to AcLDLR on macrophages. In this way, oxidized LDL accumulation in macrophages can be reduced and thus the numbers of foam cells found in cardiovascular endothelium will also be reduced, thereby interfering with early-stage atherosclerotic plaque formation.

More generally, other chimeric proteins are useful therapeutically to reduce levels of other biochemical substances associated with certain disease states. The high-affinity ligand-binding domain of chimeric proteins need not be restricted to those of known receptor molecules (e.g. LDLR or AcLDLR), but may also include other types of proteins with high binding affinity for protein ligands or small molecules. Molecules with the antigen binding properties of antibodies (for example, single chain antibodies) or other proteins having reversible binding activities can be used to construct chimeric protein-encoding sequences with human transferrin or with ligands which bind to other cell receptor ligands.

In one embodiment the chimeric protein has high-affinity binding specificity for apolipoprotein E4 (apoE4), but not to apoE3 or apoE2. Approximately half of all cases of Alzheimer Disease are associated with specific allelic forms of apoE, and the E4 allelic form of apoE is found to accumulate in amyloid fibrils in the brain and is a risk factor for the disease. The apoE2 and apoE3 alleles are not associated with increased risk and might play a role in disease resistance. A chimeric protein able to reduce apoE4 levels may be used therapeutically to slow the development of Alzheimer Disease. By the methods described herein, chimeric proteins containing an apoE4 binding domain could be fused with transferrin to produce a molecule which could remove apoE4 from the circulation and ultimately reverse the accumulation that occurs in peripheral tissues.

Diagnostic Use of Chimeric Proteins

Chimeric proteins are also useful diagnostic reagents in biochemical assays. For example, chimeric proteins can be used to determine the quantity of a selected substance, such as LDL, in a biological sample (e.g., cell lysates, blood, lymph, urine, water or milk). The biological sample to be analyzed is processed, if needed, to render the selected substance available for binding to the first domain of an appropriate chimeric protein (e.g., for LDL, one in which the first domain is the ligand-binding domain of human LDLR) and contacted with the chimeric protein under conditions appropriate for binding of the first domain and the selected substance. The chimeric protein may be generally bound to a solid surface, such as a microtiter plate, polymeric beads or other surface in such a manner that it remains bound to the surface under conditions used for binding of the selected substance to the first domain of the chimeric protein. If the selected substance is present in the biological sample, it is bound to the chimeric protein and the resulting selected substance-chimeric protein complex is detected using known means (e.g., using an antibody which binds the selected substance and is covalently linked (conjugated) to an active enzyme or radioactive nuclide. The activity of the enzyme is monitored, for example, by measuring cleavage of a chromogenic or fluorogenic substance.) Chimeric proteins can detect a substance in a direct assay, with a high degree of specificity in a convenient format, such as in a microtiter plate format. In one example presented herein, LDL is quantified by binding to LDLR/TF chimeric protein bound to a microtiter plate. The resulting bound LDL is detected by reaction with an anti-LDL antibody.

In other embodiments, chimeric proteins can substitute for antibodies in ELISA assays. For example, LDL either directly or indirectly bound to a plate can capture a chimeric protein with an LDLR ligand-binding domain. This captured chimeric protein is then detected by reaction with an HRP-conjugated antibody directed against the second domain of the chimeric protein, for example, an anti-TF antibody can react with the TF domain when an LDLR/TF chimeric protein is used. As another example, chimeric proteins which bind to components of the human immunodeficiency virus (HIV) may be used to detect the presence of the virus in complex biological samples, such as blood or tissue specimens.

The present invention is illustrated by the following examples, which are not intended to be limiting in any way.

EXAMPLE 1

Construction of a Plasmid Encoding an LDLR/TF Chimeric Protein With Amino Acids 1–374 of Human LDLR Fused to Amino Acids 20–698 of Human Transferrin Described in this example is assembly of a gene encoding an LDLR/TF chimeric protein with amino acids 1–374 of mature human LDLR fused to amino acids 20–698 of human transferrin and construction of an LDLR/TF expression plasmid.

Oligonucleotide 1:
5'  GCTGTGGCCA  CCTGTCGCCC  TGAC     (SEQ ID NO: 5)

Oligonucleotide 2:
5'  TGCACACCAT  CTCACAGTTT  TATCAGGGAC  CACAGCCTTG  CAGGCCTTCG
TGTGGGGGTC  (SEQ ID NO: 6)

-continued

Oligonucleotide 3:
5' GCCTCGAAGC TGGTTCATCT G (SEQ ID NO: 7)

Oligonucleotide 4:
5' GACCCCCACA CGAAGGCCTG CAAGGCTGTG GTCCTGATA AAACTGTGAG
ATGGTGTGCA (SEQ ID NO: 8)

Oligonucleotides 1–4 were utilized in polymerase chain reactions to generate a fusion fragment in which a cDNA sequence corresponding to exons 1–8 of the human LDL receptor were fused to a cDNA sequence encoding human transferrin. First, oligonucleotides 1 and 2 were used to amplify the 522 bp portion of the LDL receptor cDNA from pLDLR2 (ATCC #39966). Next, oligonucleotides 3 and 4 were used to amplify the 372 bp fragment comprised of transferrin sequences using plasmid TfR27A (ATCC #53106) as a template. Finally, the two amplified fragments were mixed and further amplified with oligonucleotides 2 and 3 to generate the final 834 bp fusion fragment. The PCR fusion joined LDL receptor sequences at valine 374 (numbered relative to the sequence of the mature LDLR protein) to valine 20 of transferrin sequences. This fusion fragment was digested partially with BamHI and completely with EcoRI. Analysis of the published DNA sequences of the LDLR cDNA (Genbank accession number K02573) and the TF cDNA (Genbank accession number M12530) predicts a 734 bp fragment from such a digestion of the PCR-generated fusion fragment. The 734 bp product was gel purified for cloning.

In order to construct a complete fusion between the first 374 amino acids of the human LDL receptor and DNA sequence encoding amino acids 20 to 698 of human transferrin, two intermediate plasmids were constructed. First, the entire transferrin cDNA was excised from TfR27A by partial digestion with PstI. A 2.3 kb fragment containing the TF cDNA was ligated to PstI digested pBSIISK+ (Stratagene, La Jolla, Calif.). The ligation mixture was transformed into E. coli and a clone containing a single insert of the 2.3 Kb transferrin cDNA was isolated and designated pBSIITF. Next, pBSIITF was digested with EcoRI and SacI to generate a 1.4 kb fragment corresponding to the transferrin cDNA sequence. This fragment was gel purified, and ligated to EcoRI and SacI digested pLDLR2. The ligation mixture was transformed into E. coli and a single clone containing the 1.4 kb transferrin cDNA joined to LDL receptor sequences at the EcoRI site was isolated and designated pLT1.5. A 574 bp fragment of the transferrin CDNA was then gel purified from digestion of TfR27A with EcoRI and BamHI. This fragment and the 734 bp LDL receptor/transferrin fusion fragment (generated by EcoRI and partial BamHI digestion of the PCR product as described above) were ligated to EcoRI digested pLT1.5. The ligation mixture was transformed into E. coli and a single clone was isolated containing sequence encoding the first 395 amino acids of the human LDL receptor (374 amino acids of the mature protein with a 21 amino acid signal peptide) fused to the entire mature transferrin coding sequence (amino acids 20–698). This plasmid was designated pLDLrTF1.

Figure 2:
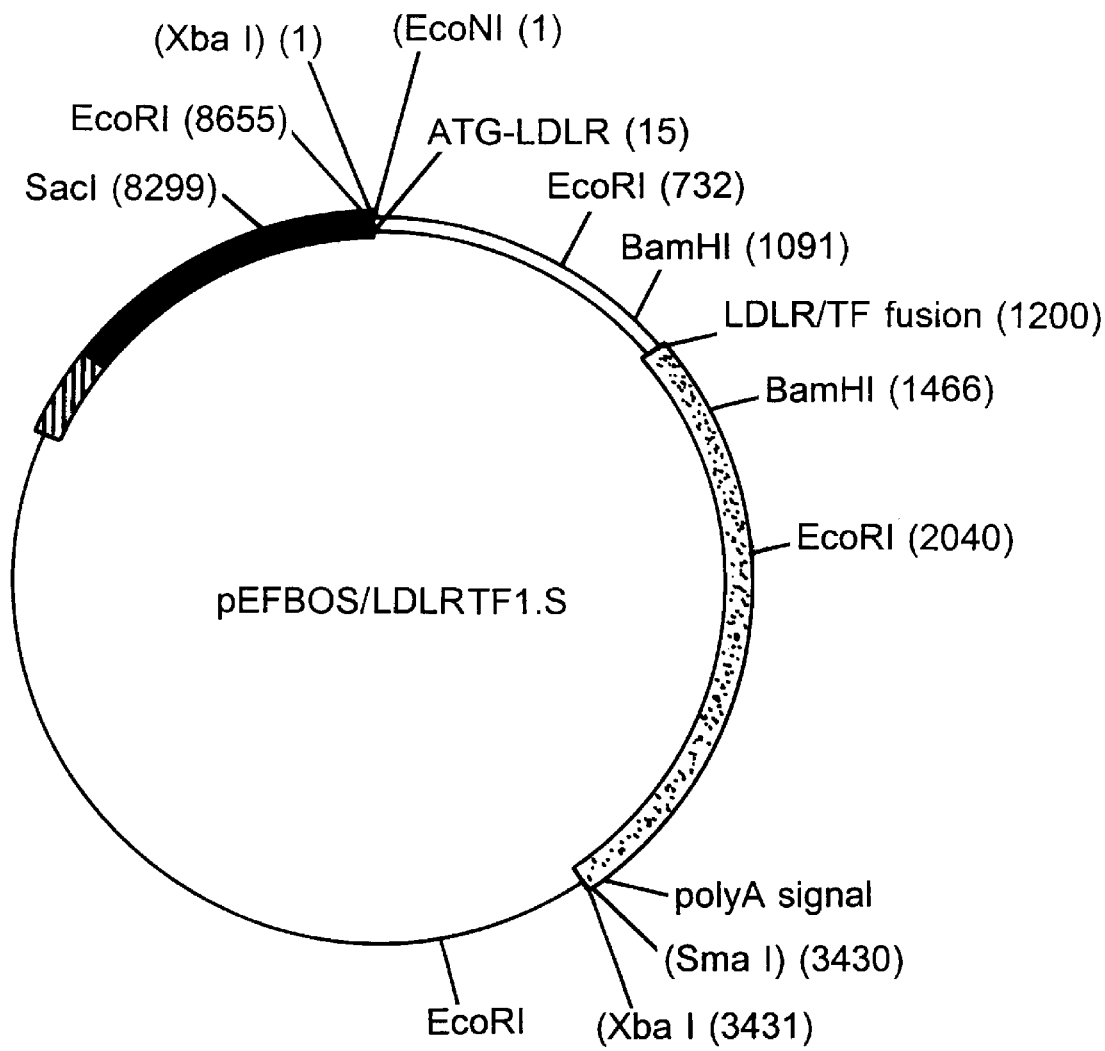
FIG. 2 is a schematic representation of LDLR/TF expression plasmid pEFBOS/LDLrTF1.S. Specific regions of the plasmid are denoted by the shadings or lines indicated. Restriction endonuclease sites eliminated as a result of blunting the termini of XbaI-digested pEF-BOS by treatment with Klenow fragment of E. coli. DNA polymerase and ligation to the EcoNI-SmaI fragment containing the fusion gene in which the EcoNI site was similarly blunt-ended are in parentheses.

To construct a plasmid useful for expression of the chimeric protein in mammalian cells, the chimeric protein coding sequences were isolated from the plasmid pLDLrTF1 following digestion with SmaI and EcoNI. The cohesive end resulting from EcoNI digestion was made blunt using the Klenow fragment of E. coli DNA polymerase. The digested DNA was electrophoresed on a 1% low-melting agarose gel and the 3.4 kb DNA fragment corresponding to the chimeric cDNA was extracted. This fragment was ligated to the plasmid pEF-BOS (Mizushima, S. and Nagata, S., Nucleic Acids Res. 18:5322 (1990)) that had been gel purified following XbaI digestion and Klenow treatment. Plasmid pEF-BOS utilizes the promoter sequences from the elongation factor-1a (EF-1a) gene. Competent E. coli were then transformed with this ligation mixture. Transformants were screened by restriction enzyme analysis, and one clone with the desired orientation of the LDLR/TF fusion gene in plasmid pEF-BOS (the orientation in which the coding sequence extends 3' from the EF-1a promoter) was isolated and designated pEFBOS/LDLrTF1.S (FIG. 2). The complete nucleotide sequence of the LDLR/TF fusion gene in plasmid pEFBOS/LDLrTF1.S is shown in FIG. 3.

EXAMPLE 2

Construction of a Plasmid Encoding an LDLR/TF Chimeric Protein With Amino Acids 1–710 of Human LDLR Fused to Amino Acids 20–698 of Human Transferrin This example describes assembly of a gene encoding an LDLR/TF chimeric protein with amino acids 1–710 of human LDLR fused to amino acids 20–698 of human transferrin and the construction of an LDLR/TF expression plasmid. In this example of an LDL receptor-transferrin (LDLR/TF) chimeric protein, the fusion junction follows the valine codon at position 731 of the mature LDLR polypeptide. The plasmid pLDLR2 obtained from the ATCC (ATCC #39966) contains the cDNA sequences for the human LDL receptor (LDLR). The cDNA sequence was inserted into plasmid pBS (Stratagene, La Jolla, Calif.) by the following steps to facilitate the construction of a chimeric gene. pLDLR2 was digested with EcoNI and the ends were made blunt by treatment with the Klenow fragment of E. coli DNA polymerase. The treated DNA was then digested with BglII. The 1,735 bp EcoNI-BglII fragment containing the 5' 1,721 bp of the LDLR CDNA as well as 5' untranslated flanking sequences was isolated. A 976 bp DNA fragment containing the remaining 925 bp of the cDNA and 3' untranslated flanking sequences was isolated following digestion of pLDLR2 with BglII and NaeI. Plasmid pBS was linearized by digestion with EcoRV and the LDLR CDNA sequences was reassembled by ligation of the isolated 1,735 bp 5' LDLR and 976 bp 3' LDLR fragments to EcoRV digested pBS using T4 DNA Ligase. After transformation of the ligation mixture into competent E. coli cells, individual bacterial clones were analyzed by restriction enzyme analysis. One clone, with the properly assembled LDLR cDNA was designated pBSL-1.

The human transferrin cDNA sequences were obtained from ATCC deposit #53106, clone TfR27A. The 2.3 kb transferrin cDNA sequences were excised from TfR27A by digestion with Pst I and inserted into the Pst I site of cloning plasmid pBSIISK+(Stratagene), resulting in the plasmid pBSIITF.

To prepare a DNA fragment containing the fusion junction between amino acid 731 of LDLR (numbered relative to the amino acid sequence of the mature protein) and amino acid 20 of TF, oligonucleotides LDLRTF710-1, -2, -3, and -4 were used in the polymerase chain reaction.

LDLRTF710-1:
5' TGCACACCAT CTCACAGTTT TATCAGGGAC GACCTTTAGC CTGACGGT
(SEQ ID NO: 9)

LDLRTF710-2:
5' TCAGTGGCCC AATGGCATC
(SEQ ID NO: 10)

LDLRTF710-3:
5' CAGGAGACAT CCACCGTCAG GCTAAAGGTC GTCCCTGATA AAACTGTGAG A
(SEQ ID NO: 11)

LDLRTF710-4:
5' CTTCCCATGA GGAGAGCT
(SEQ ID NO: 12)

The plasmid templates were linearized in preparation for the PCR reactions by digestion of pBSIITF with SalI and PBSL1 with NotI. Creation of the fragment containing the fused coding sequences was performed in two steps. The first step consisted of a reaction mix containing 10 µl of Vent DNA polymerase (New England Biolabs, Beverly, Mass.), 1 ng each of linearized pBSIITF and pBSL1 DNA, 12 µl of 2.5 mM dNTP's, 0.3 µl of oligos LDLRTF710-2 and -4, 1 µl oligos LDLRTF710-1 and -3, and H$_2$O to bring the final volume to 100 µl. The 1.4 kb fusion fragment resulting from this PCR amplification was further amplified with oligonucleotides LDLRTF710-2 and -4. The amplified 1.4 kb fragment was gel purified and digested with EcoNI and EcoRI and ligated to a 2.18 kb SalI-EcoNI fragment containing the LDLR sequences from pBSL1, a 1.55 kb EcoRI-XbaI fragment from pBSIITF (containing TF cDNA sequences) and SalI-XbaI digested pBSIISK (Stratagene, La Jolla, Calif.). The ligation mixture was used to transform competent E. coli cells. One clone with the correctly assembled fragments from the 4-way ligation was designated pLDLRTF-710.

Figure 4:
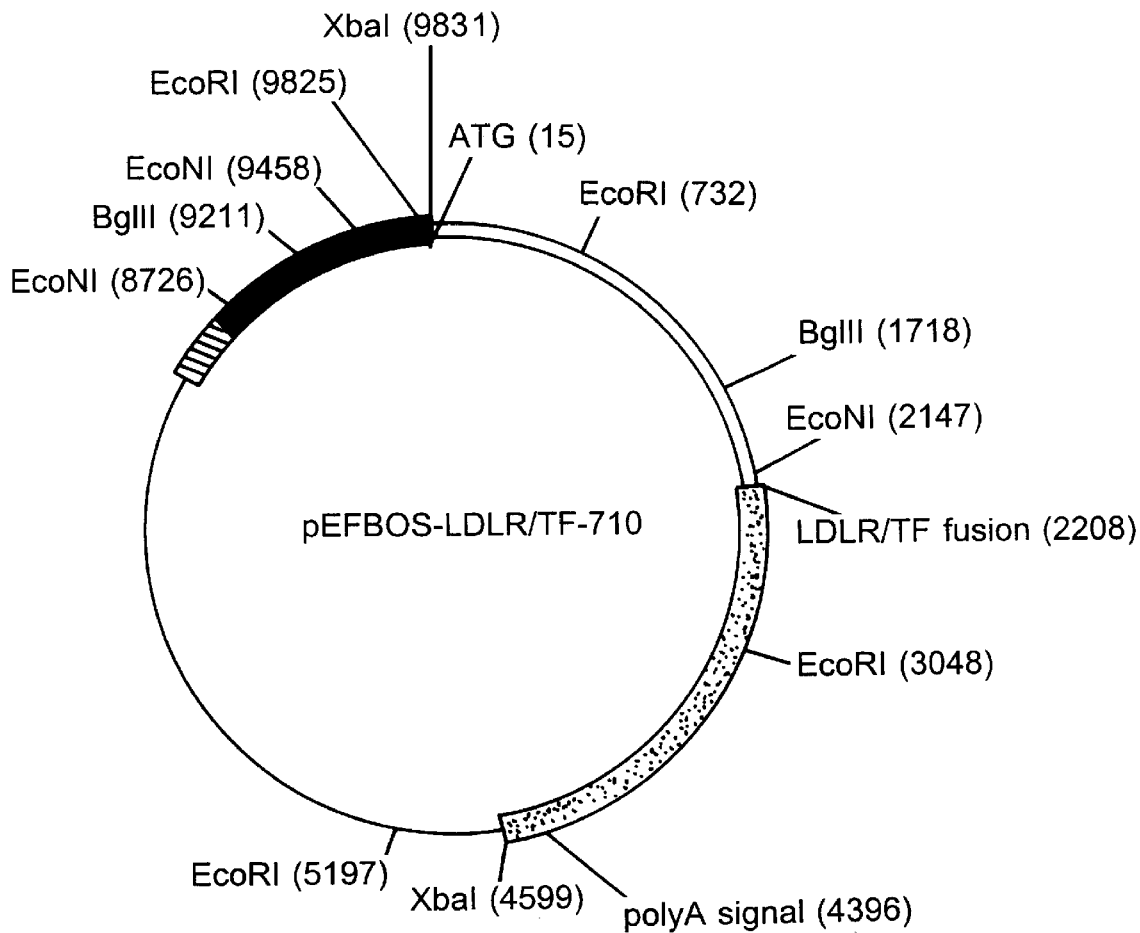
FIG. 4 is a schematic representation LDLR/TF expression plasmid pEFBOS-LDLR/TF-710, in which specific regions of the plasmid are denoted by the shadings or lines indicated.

For expression of the chimeric cDNA in mammalian cells, the chimeric cDNA of pLDLRTF-710 was subcloned into expression plasmid pEF-BOS (Mizushima, S. and Nagata, S., *Nucleic Acids Res.* 18:5322 (1990)) which utilizes the promoter sequences from the elongation factor-1a (EF-1a) gene. pEF-BOS was digested with XbaI to remove the 450 bp stuffer fragment. The SalI site lying at the junction between pBSIISK+and LDLR sequences of pLDLRTF-710 was modified by addition of an XbaI linker. Digestion of this modified fragment with XbaI generates a 4.4 kb XbaI fragment containing the LDLR/TF fusion gene. The 4.4 kb XbaI fragment was purified and ligated to XbaI digested pEF-BOS. The ligation mixture was used to transform competent E. coli cells. One clone with the correct orientation of the LDLR/TF fusion gene XbaI fragment in plasmid pEF-BOS (the orientation in which the coding sequence extends 3' from the EF-1a promoter) was designated pEFBOS-LDLR/TF-710 (FIG. 4). The complete nucleotide sequence of the LDLR/TF fusion gene in plasmid pEFBOS-LDLR/TF-710 is shown in FIG. 5.

EXAMPLE 3

Transfection of Mammalian Cells with Plasmids Encoding LDLR/TF Chimeric Proteins and Identification of Clones Expressing LDLR/TF Chimeric Proteins A. Transfection of Primary Human Skin Fibroblasts In this example, normal skin fibroblasts derived from newborn human foreskins are cultured in a medium consisting of DMEM (Cellgro 50-013), 15% bovine calf serum (Hyclone), units/ml of each of penicillin and streptomycin (Gibco 15070-014), and 2.25% Hepes buffer (Gibco 15630-015). Growing cells are washed in electroporation buffer (137 mM NaCl, 6 mM glucose, 5 mM KCl, 0.7 mM Na$_2$HPO$_4$, 1 mg/ml acetylated BSA[Sigma B-2518], 20 mM Hepes buffer, pH 7.3) and resuspended in electroporation buffer at 6 million cells per ml. Plasmid DNA (100 µg total) is added to an electroporation cuvette (BIO-RAD 165-2085) in a volume less than 50 µl, followed by addition of 0.5 ml of cell suspension (3 million cells total).

Plasmid DNA consists of an equimolar mixture of the plasmid encoding the chimeric protein (in this example 61.2 µg of pEFBOS/LDLrTF1.S (8.66 kb) see Example 1) and the plasmid carrying a dominant-selectable drug-resistance marker, in this example 38.8 µg of plasmid pSV2neo (5.50 kb; ATCC #37149). Plasmid pSV2neo is used to provide a positive selection for stably transfected cells, based upon resistance to the drug G418.

The cuvette is subjected to an electric pulse (250 volts, capacitance setting of 960 µFarad), permitting efficient entry of DNA into cells. Cells are diluted and plated into tissue culture dishes containing the same growth medium having, in addition, 0.4 mg/ml of G418 (GENETICIN®, Gibco 860-1811). Only cells stably transfected with either pSV2neo or both pSV2neo and pEFBOS/LDLrTF1.S are able to form colonies in this medium. Cells that fail to integrate pSV2neo into their genomes are killed by this drug and do not form clones. Other co-transfecting plasmids conferring dominant selectable drug resistance may be used.

After 2–3 weeks of incubation, G418-resistant cell clones are identified visually and transferred to multi-well plates for further growth in the drug-containing medium. Isolated drug-resistant transfectant clones are then screened for co-expression and secretion of the chimeric protein derived from the chimeric protein-encoding plasmid, in this example pEFBOS/LDLrTF1.S.

To identify chimeric protein-expressing clones, conditioned medium from each clone is tested for the presence of the chimeric protein in an assay based on detecting, in this example, the cellular receptor ligand domain, which, in this example, is human transferrin. A sandwich enzyme immunoassay for human transferrin (TF ELISA; see Example 6) is used to detect chimeric protein in the conditioned medium. Clones positive for LDLR/TF expression are cultured separately and analyzed quantitatively for levels of chimeric protein expression.

In one experiment, 206 transfected clones growing in medium containing 0.4 mg/ml G418 were isolated with the aid of cloning rings and transferred to 96-well culture dishes. After a growth period, conditioned media was tested by TF ELISA for the presence of TF antigen and 22 were found to be positive. Negative control cultures (clones of untransfected cells growing in the absence of G418 or G418-resistant clones isolated after transfection with pSV2neo) did not express detectable human TF antigen. 16 of the 22 positive clones were expanded for further analysis. Cultures in T-25 flasks were grown to near-confluence and exposed to fresh culture medium. After 24 hours, the medium was isolated for quantification of chimeric protein levels by TF ELISA. The cells were then trypsinized and cell counts were determined using a Coulter Counter. The total amount of chimeric protein in conditioned media from each flask was calculated (in nanograms (ng) transferrin equivalents [$TF_{eq}$]) and divided by the total number of cells in each flask, resulting in a quantitative measure of expression rate, which can be expressed as ng $TF_{eq}$ per $10^6$ cells per day. Chimeric protein expression levels in 15 of the expressing clones were determined to be: 2, 7, 11, 21, 49, 52, 90, 93, 99, 131, 175, 193, 200, 206, and 231 ng $TF_{eq}$ per $10^6$ cells per day.

B. Transfection of Chinese Hamster Ovary (CHO) Cells

CHO cells are transfected with the chimeric protein expression plasmid, in this example pEFBOS/LDLrTF1.S, by the calcium phosphate precipitation procedure (Graham, F. L., and van der Eb, A. J., Virology, 52:456 (1973); Chu and Sharp, Gene, 13:197 (1981)). A co-transfecting dominant selectable marker plasmid, pSV2dhfr, is also used for clonal selection of stably transfected cells, based on complementation of a nonfunctional dihydrofolate reductase (dhfr) gene in the host CHO cell line, DUKX-B11(in Chasin, L. and Urlaub, G., Proc. Natl. Acad. Sci. USA, 77:4216 (1980)). In the experiments described below, the dhfr gene in plasmid pSV2dhfr was used (S. Subramani et al., Mol. Cell. Biol., 2:854–864 (1981)), in which dhfr is expressed from an SV40 promoter.

Cells from DUKX-B11 are cultured in a complete medium consisting of aMEM (free of ribonucleosides and deoxyribonucleosides, Sigma M-4526), 10% fetal bovine serum (Hyclone A-1111), 4 mM L-glutamine (Gibco 25030-016), 50 units/ml each of penicillin and streptomycin (Gibco 15070-014), 15 µg/ml L-proline (Sigma P-4655), 10 µg/ml adenosine (Sigma A-4036), 10 µg/ml thymidine (Sigma T-1895), and 10 µg/ml deoxyadenosine (Sigma D-8668).

Cells growing in a T75 flask at approximately 60–70% confluence in 20 ml of complete medium, were fed with 10 ml of fresh complete medium and incubated at 37° C. for 4 hours. Thirty minutes prior to the end of the 4-hr period, a suspension of fine precipitates of calcium phosphate and plasmid DNA is prepared as follows:

Plasmid pEFBOS/LDLrTF1.S (50 µg) and pSV2dhfr (1 µg) were combined in a total of 0.5 ml of TE buffer (1 mM Tris-HCl, 0.1 mM EDTA, pH 7.9) containing 0.25M $CaCl_2$. This solution was added dropwise to 0.5 ml of another solution containing 280 mM NaCl, 1.5 mM $Na_2HPO_4$, 50 mM Hepes, pH 7.1. The 1 ml mixture was left undisturbed for 30 min. at room temperature to allow calcium phosphate precipitates to form. The 1 ml of suspension was added to the 10 ml of medium previously bathing the cells for 4 hours. The medium was swirled to disperse the particles and the cells were incubated at 37° C. for an additional 4 hours. The medium was removed by aspiration and the cells were contacted for 1 minute at room temperature with 5 ml of complete medium containing 20% glycerol. The glycerol was subsequently removed by the addition of 15 ml of complete medium, followed by two additional washes of the cells with 20 ml each of complete medium. The cells were then fed with 20 ml of complete medium and incubated at 37° C. for 24 hours, to allow chromosomal integration and expression of the transfecting plasmid DNA. After 24 hours, the cells were trypsinized and divided into 7 cultures (i.e. pools A-G) of equal size in DHFR selection medium.

DHFR selection medium provides a positive selection for only those cells that have taken up and expressed plasmid pSV2dhfr (with or without pEFBOS/LDLrTF1.S). Cells that do not express DHFR do not grow in this selection medium. DHFR selection medium contains aMEM (see above), 10% dialyzed fetal bovine serum, 4 mM L-glutamine, 50 units/ml of each of penicillin and streptomycin and 15 µg/ml L-proline. This medium contains 0.1% glucose and 0.22% sodium bicarbonate.

Pools A-G were grown to near confluence in DHFR selection medium for 17 days, during which time fresh selection medium was replenished every 3 or 4 days. Then, the cells in each pool were fed with 20 ml of fresh selection medium, incubated for 24 hours, and the conditioned media were recovered and tested for the level of chimeric protein by TF ELISA.

Bovine transferrin antigen contained in this selection medium does not cross-react with the antibodies against human transferrin that are used in the TF ELISA. Moreover, the untransfected host CHO cell line, DUKX-B11, does not synthesize a secretable transferrin antigen detectable in the assay. Consequently, detection of any concentration of transferrin antigen in conditioned media from transfected cell populations that is above the background level for the assay (1 ng/ml) constitutes evidence that the transfected population is expressing and secreting a LDLR/TF chimeric protein.

Following the 17-day growth period in DHFR selection medium, media conditioned for 24 hours by cells from pools A through G contained detectable levels of chimeric protein. In this example, pools A through G produced 53, 52, 52, 79, 74, 75, and 33 ng $TF_{eq}$/ml, respectively, at the end of this 1-day conditioning period. Thus, initially all pools produce comparable but nonidentical levels of chimeric protein. Therefore, selection for expression of pSV2dhfr-encoded DHFR enzyme results in co-expression of chimeric protein derived from pEFBOS/LDLrTF1.S, since a significant fraction of the cells integrate both plasmids in an expressible form.

Cell populations A-G were subsequently treated with any one of a number of well-established DHFR gene amplification protocols (Kaufman, R. J. and Sharp, P. A., J. Mol. Biol., 159:601 (1982)), which select for subpopulations expressing higher levels of DHFR enzyme, which, in turn, is correlated with increased resistance to the toxic antifolate drug methotrexate (MTX). In this example, pools were first selected for resistance to 20 nM MTX and then to 50 nM MTX (Sigma M-8407). At each step, the level of co-expression of secreted chimeric protein in each respective subpopulation is monitored by TF ELISA. Subpopulations exhibiting increases in expression of chimeric protein product are likely to contain certain high-expressing cells, which can be isolated from the subpopulation by cell cloning.

In this example, subpopulations of pools E and F exhibited strong increases in chimeric protein expression at 20 nM MTX and at 50 nM MTX as compared to the other pools. Cells from both pools E and F selected at 50 nM MTX were subsequently cloned by limiting dilution methods; 9 cell clones from pool E and 14 from pool F were identified as the best producers from a larger number of clones that had been isolated and tested by TF ELISA for chimeric protein production in multi-well culture plates. These 23 clones, including the 2 highest from pool E (E77 and E117) and the 2 highest from pool F (F3 and F57) were evaluated further, with respect to potential for increased product output after additional rounds of DHFR gene amplification (Example 4).

EXAMPLE 4

Identification of a Producer Cell Line and Assessment of Potential Modifiers of Chimeric Protein Production A. Identification of a producer cell line Methotrexate (MTX)-resistant CHO cell lines derived from the dhfr-deficient CHO line DUKX-B11 were grown in DHFR selection medium (Example 3) with 100 riM MTX (Sigma M-8407). This medium contains 0.1% glucose. Some media also contained 2 mM sodium butyrate (Fluka 19364), or serine protease inhibitor aprotinin (Boehringer Mannheim 981-532) or Pefablock SC (Boehringer Mannheim 1429-876).

From pool E, the two highest expressing clones (E77, which produced approximately 1.5 μg TF$_{eq}$/ml over a 4-day period in 6-well plates and E117 which produced 1.1 μg TF$_{eq}$/ml over 4 days in 6-well plates) were cultured separately and amplified by selecting for resistance to 100 nM MTX, to determine whether production of the chimeric protein would increase. All 9 clones from pool E were also combined into a new pool called pool H, which was subsequently amplified by selecting for resistance to 100 nM MTX. In the same manner, the two highest expressing clones from pool F (F3 and F57) were separately amplified by selecting for resistance to 100 nM MTX, and all 14 clones from F were combined into a new pool called pool J, which was similarly amplified.

The 4 clones (E77, E117, F3, and F57) and pools H and J were evaluated for increased productivity (ng TF$_{eq}$ per $10^6$ cells per day) in T75 culture flasks as a function of increasing DHFR amplification. Production of chimeric protein was assayed by TF ELISA. The stability of such productivity was also monitored by measuring product output during subsequent subculture at the same level of MTX resistance.

Results (see Table 1) show that clone E77 appeared to be the highest stable producer. Subsequent amplification to 200 nM and 500 nM MTX did not result in higher productivity of chimeric protein. Similarly, selection for increased MTX resistance in pools H and J did not result in selection for higher producing sub-populations.

Clone E77 appeared to grow well in 100 nM MTX and was chosen as the producer cell line for roller bottles.

TABLE 1

Chimeric protein productivity (ng TF$_{eq}$/$10^6$ cells/day) in CHO transfectant pools and clones as a function of MTX concentration and subculture round.

| [MTX] (nm) | Sub-culture Round | E77 | E117 | F3 | F57 | Pool H | Pool J |
|---|---|---|---|---|---|---|---|
| 50 | 1 | 1577 | 479 | 616 | 830 | 404 | 328 |
| 50 | 2 | 1167 | ND | 552 | 608 | ND | ND |
| 100 | 1 | 3554 | 800 | 620 | 1031 | 505 | 224 |
| 100 | 2 | 1842 | 1532 | 347 | 604 | 381 | 187 |
| 100 | 3 | 2011 | 729 | 641 | 1135 | 252 | 121 |
| 100 | 4 | 1462 | 593 | ND | ND | ND | ND |
| 200 | 1 | 1791 | 779 | 699 | 1045 | 404 | 90 |
| 200 | 2 | 2000 | 728 | 855 | 948 | 327 | 97 |
| 200 | 3 | 1598 | 928 | 975 | 546 | 510 | 100 |
| 500 | 1 | 1577 | 957 | 855 | ND | 319 | 50 |
| 500 | 2 | ND | 954 | ND | ND | 322 | 52 |

ND: not determined

B. Assessment of potential modifiers of chimeric protein production

The quantity and quality of chimeric protein production by producer cell line E77 was studied in T flasks and in roller bottles.

Previous immunoprecipitation experiments had shown that a small fraction of protein immunoprecipitated from the culture supernatants of human fibroblasts transfected with plasmid pEFBOS/LDLrTF1.S retained the TF domain but lacked an intact LDLR domain. The same was found to be true of the chimeric protein secreted by the CHO cell line E77 (as well as in other clones and pools of CHO transfectants). The hypothesis that this smaller product might result from the action of a specific endopeptidase at a site within the LDLR domain was assessed by determining whether the accumulation of this species could be inhibited by specific protease inhibitors or by using serum that had been heat inactivated. The serine protease inhibitor aprotinin at 0.002% had a small effect in reducing the relative abundance of this smaller species. Subsequently, a higher aprotinin concentration (0.5%) was tested.

Cells were grown to confluence in T75 flasks in 3 different media, all of which contained DMEM and 100 nM MTX. Medium A contained 10% dialyzed FBS (fetal bovine serum) and no additions, medium B contained 10% heat inactivated dialyzed FBS, while medium C was the same as medium A except for the addition of 0.5% aprotinin. Cultures were fed with media A, B or C, respectively, and incubated. Small samples of conditioned media were removed at one and two days after feeding and incubated for 7 days at 37° C. After incubation, each sample was electrophoresed on a non-reducing SDS/polyacrylamide gel, transferred to nitrocellulose, and detected by binding to horse radish peroxidase (HRP) conjugated sheep anti-human TF.

The results showed that the smaller species accumulated after 2 days in medium A, and was present at low abundance at all three conditions after one day. Feeding with medium B (heat-inactivated serum) did not prevent this in vitro proteolysis, consistent with the view that the proteolytic agent was not a heat-inactivatable component of the serum. The addition of 0.5% aprotinin (medium C), however, significantly reduced the extent of proteolysis. This supports the idea that degradation of the full-length chimeric protein, observed during the conditioning of media by confluent cultures, is caused by a secreted serine protease with specific endopeptidase activity.

Inhibition of serine protease activity was also achieved using another inhibitor (Pefablock SC; PB). Increasing concentrations of PB in culture medium results in decreasing relative abundance of the 100 kd degradation product, when 3-day conditioned media were analyzed by western blotting. Use of 0.6 mM PB appears to have a very strong suppressive effect, although 0.3 to 0.5 mM PB also significantly reduces degradation.

EXAMPLE 5

Roller Bottle Production of LDLR/TF Chimeric Protein

Initial attempts at scaling up chimeric protein production involved using 20 expanded surface (1450 cm$^2$) roller bottles (Falcon 3069) with 250 ml of medium per bottle, each rotating at 0.3 revolutions per minute. E77 cells were grown to confluence and fed and harvested weekly (Example 4). The 20 bottles were divided among 3 treatment groups. Roller bottles RB8 through RB12 were fed with 100 nM MTX medium. RB3-RB7 were fed with medium lacking MTX. RB13-RB22 were fed with 100 nM MTX medium, but had been seeded with a subclone of E77 called SC7.

Overall, 48.5 liters were produced which contained 96 mg TF$_{eq}$ or 149 mg of chimeric protein with an average yield of 3.1 mg of chimeric protein per liter. RB13-RB22 had the lowest average chimeric protein concentration of 2.2 mg/liter, while the groups RB3-RB7 and RB8-12 produced an average of 3.3 mg/liter and 3.8 mg/liter, respectively. From these results it would appear that removal of the MTX selective agent did not increase yield. All 48.5 liters of conditioned media saved from RB3-RB22 were pooled and concentrated for subsequent purification.

EXAMPLE 6

TF ELISA

In the sandwich enzyme immunoassay for detecting the human TF antigen contained within the chimeric protein (TF ELISA), MAb HTF-14 (Biodesign H61016M) was used to coat plates at 1:1000 in 1X PBS (Gibco 310-4200AJ). Human apo-TF (SIgma T-1147) in ELISA blocking buffer (PBS, 2% BSA, 0.05% Tween-20) was used as a standard. Human holo-TF (iron saturated) exhibited the same standard curve as apo-TF (iron-free). The enzyme conjugate for detection was horseradish peroxidase (HRP)-sheep anti-human TF (Biodesign K90070P) used at 1:5000 in ELISA blocking buffer. The HRP substrate was OPD (Dako S-2000), prepared by dissolving 8 mg OPD in 12 ml of 0.1M citric acid-phosphate buffer, pH 5.0, with 0.0125% $H_2O_2$.

The TF ELISA effectively detects the molar concentration of chimeric protein, based on comparison with the human apo-TF standard. The molecular weight of the protein component of the chimeric protein (116.3 kilodaltons) is 55% larger than the that of human TF (75.1 kd). Assuming that the chimeric protein has the same affinity for MAb HTF-14 and for HRP-sheep anti-human TF as does the human TF standard, then the concentration of chimeric protein can be expressed as a value equivalent to nanograms of TF equivalents per ml (i.e., ng $TF_{eq}$/ml). Thus, in this case the actual concentration of chimeric protein on a ng/ml basis is approximately 55% higher.

EXAMPLE 7

Purification of LDLR/TF Chimeric Protein

The following materials and methods were used in this example. For purification of IgG from MAb HTF-14 ascites fluid, Goat anti-mouse IgG agarose beads (Hyclone EK-4081) were used. Mouse IgG was detected with HRP-conjugated Sheep anti-mouse IgG (Cappel 55565). HTF-14 IgG was reacted with cyanogen bromide-activated sepharose to covalently bind the antibody to the sepharose beads for immunoaffinity (IA) purification of TF epitope-containing chimeric protein species. For IA chromatography based on LDL binding, affinity-purified rabbit anti-human LDL (Biomedical Technologies BT-905) was first reacted covalently with cyanogen bromide-activated sepharose, and then, in turn, was used to noncovalently immobilize purified human LDL (Biomedical Technologies TB-903). Rabbit IgG was detected with HRP-conjugated goat anti-rabbit IgG (Cappel 55689).

A. Purification by Anti-TF immunoaffinity chromatography

1. Isolation of IgG from MAb HTF-14 ascites fluid

The anti-transferrin monoclonal antibody HTF-14 was isolated from ascites fluid (Biodesign, H61016M, subclass IgGI) using a Monoclonal Antibody Affinity Isolation System (Hyclone, EK-4081). This system employs as antibody anti-mouse IgG-coated agarose beads to bind and separate the monoclonal from the ascites fluid. The antibody was eluted in a single step with 50 ml of 30 mM acetic acid containing 85% NaCl and dripped into solid sodium borate for a final concentration 0.1M sodium borate, 30 mM acetic acid, 85% NaCl. The pools were immediately placed into 12–14 kd cut-off dialysis tubing and dialyzed overnight at 4° was then frozen at −20° C. The pools were thawed, combined and concentrated with Amicon Centriprep 50 to 12.5 ml at 4.36 mg protein/ml. Fifty-four milligrams of anti-transferrin monoclonal antibody was purified from 112 ml of ascites fluid. The yield on this step of the purification was 99% of the available antibody.

2. Immobilization of HTF-14 to cyanogen bromodeactivated sepharose

The purified monoclonal anti-human transferrin antibody (HTF-14) was covalently bound to Cyanogen-Bromide activated Sepharose 4B (CN-Br 4B) (Pharmacia). Twelve grams of support was swelled to 37 ml in 0.01N HCl. The beads were the washed with 10 volumes of 0.1M $NaHCO_3$ pH 8.3 containing 0.5M NaCl. The antibody solution, HTF-14 at 4.36 mg/ml in 0.1M $NaHCO_3$ pH 8.3 containing 0.5M NaCl, was added and allowed to react while shaking gently on a motorized rotating platform for 20 hours at 4° C. Free amine groups were blocked via the addition of 30 ml of 1M ethanolamine pH 8.5 for 3 hours with rotation.

3. Binding and elution of chimeric protein from concentrated conditioned media pool The support was degassed and poured into a 50 ml Pharmacia Econo-column. It was equilibrated in TBS pH 7.4. The culture supernatant had previously been concentrated 32-fold (48.5 liters to 1.5 liters). It was re-assayed and shown to contain 62.3 mg of transferrin equivalents and 1,044 grams of total protein. This culture supernatant was spun at 10,000 rpm and filtered through a 0.22 $\mu$M filter. It was then loaded directly onto the HTF-14 immunoaffinity column at 100 mls/hour with cycling for 40 hours. The column was washed with 10 column volumes of TBS pH 7.4. The column was then eluted with 0.1M glycine pH 2.3. Two ml fractions were collected into tubes containing 1 ml of 2M Tris-HCl pH 8.5, to neutralize the elution buffer. Fractions 7–30 were pooled. It was determined that the pool contained 26.4 mg of chimeric protein (both undegraded and protease degraded fractions) in 54 mg of total protein, corresponding to a purity level of 49% and a 8,193-fold purification in one-step from culture media.

B. LDL ligand-affinity chromatography

1. Immobilization of rabbit anti-human LDL to cyanogen bromide-activated sepharose Five milligrams of polyclonal rabbit anti-human LDL antibody (Biomedical Technologies, BT-905) was bound to Cyanogen-activated Sepharose 4B (CN-Br 4B) (Pharmacia). The rabbit anti-hLDL was dialyzed into 0.1M $NaHCO_3$ pH 8.3 containing 0.5M NaCl. 350 $\mu$g of support was swelled in 0.01N HCl. The support was then washed with 10 volumes of 0.1M $NaHCO_3$ pH 8.3 containing 0.5M NaCl. The antibody solution was added and reacted by gentle mixing for 24 hours at 4° C. Free amine groups were then blocked by the addition of 2 ml of 1M ethanolamine pH 8.5 for 1 hour with gentle mixing. 99% of the available antibody bound to the column, producing a 1 ml anti-hLDL column with 5 mg of anti-hLDL covalently bound.

2. Binding of LDL

Ten milligrams of LDL (Biomedical Technologies, BT-903) at 5 mg/ml in 50 mM Tris, 0.15M NaCl and 0.3 mM EDTA was obtained. It was dialyzed into TBS containing 2 mM $CaCl_2$. The 10 mg of LDL was cycled 10 times over the anti-hLDL column at a concentration of 2 mg/ml. It was determined that 3.2 mg of LDL remained in the flow-through, indicating that approximately 6.8 mg of hLDL was bound to the column.

3. Binding and elution of chimeric protein from IA pool

A 1 ml pool of concentrated immunoaffinity purified chimeric protein (purified on the anti-TF IA column) containing 138 $\mu$g chimeric protein was cycled 10 times over the 1 ml anti-hLDL/LDL ligand affinity column. Assuming a 1:1 ratio of undegraded protein to proteolytically cleaved protein, this translates to approximately 67 $\mu$g of intact protein. The flow-through contained 29 $\mu$g or 21% of the chimeric protein. The column was washed with 20 volumes of TBS pH 7.4, and then eluted with 20 mM EDTA in TBS pH 7.4. One ml fractions were collected. It was determined by absorbance at 280 nm that fractions 2 and 3 contained the peak of protein. These fractions were concentrated in an Amicon Centriprep 100 filtration unit by centrifugation for 30 min at 1000 rpm. It was determined that 10.2 μg of the loaded intact chimeric protein was eluted in the peak fractions.

EXAMPLE 8

Purification of LDLR/TF Chimeric Protein Utilizing Protease Inhibition and Dissociation of Bound Bovine LDL The previous example describes a purification protocol that isolates undegraded LDLR/TF chimeric protein from roller bottle cultures of CHO producer cell line E77, employing the following steps: 1) accumulation and concentration of conditioned media, 2) immunoaffinity chromatography (specific binding of the human transferrin domain of the chimeric protein to immobilized HTF-14 monoclonal antibody), and 3) ligand-affinity chromatography (specific binding of the human LDLR domain of the chimeric protein to immobilized human LDL). While the previous example describes a two step procedure for isolating LDLR/TF chimeric protein, the LDL ligand-affinity chromatography step is relatively inefficient (i.e. only a fraction of the load protein is recovered). This is probably due to the fact that immunoaffinity-purified chimeric protein contains bound cholesterol, likely in the form of bovine LDL particles derived from the dialyzed fetal bovine serum used during cell culture. Thus, human LDL binding may be inhibited in a fraction of chimeric protein molecules due to bound serum-derived bovine LDL-cholesterol. The protocol presented in this example involves dissociation of bovine LDL from the chimeric protein prior to binding to immobilized human LDL.

Chimeric protein is accumulated in culture medium containing the serine protease inhibitor Pefablock® SC (added to fresh culture medium at a concentration of 0.2 mM). This inhibitor has no significant effect on the level of total chimeric protein produced, but it does increase the relative yield of intact LDLR/TF. Conditioned medium is concentrated and loaded onto an HTF-14 immunoaffinity column. Since LDL binding to the chimeric protein's LDLR domain is divalent cation-dependent, while the binding of MAb HTF-14 to the chimeric protein's transferrin domains is divalent cation-independent, the column containing bound chimeric protein is washed with EDTA to specifically elute bovine LDL bound to chimeric protein. Following the EDTA wash, chimeric protein is eluted with 0.1M glycine (pH 2.3) as described in Example 7, with the result being that the LDLR/TF product contains much less associated cholesterol. This material is useful for in vitro and in vivo experiments or for therapeutic use. Optionally, it may also be purified further by human LDL ligand-affinity chromatography to remove degraded product which has lost the LDLR binding domain.

In order to illustrate the difference between immunoaffinity-purified chimeric protein with bound bovine LDL (Example 7) and immunoaffinity-purified chimeric protein depleted of bovine LDL (this Example), chimeric protein produced with protease inhibitor is first bound to the HTF-14 immunoaffinity column, eluted, and reapplied to the HTF-14 column. A total of 43.51 liters of conditioned medium produced in the presence of 0.2 mM Pefablock® SC and containing 56.1 mg of chimeric protein is concentrated to a volume of 1.17 liters containing 50.8 mg of chimeric protein (91% recovery), using a Pellicon Tangential-Flow Filter System fitted with a 100,000 dalton molecular weight cutoff filter cassette (Millipore). The concentrate (50.8 mg of chimeric protein, 90.7 g of total protein) is applied to the HTF-14 column (87% binding) and eluted with 0.1M glycine (pH 2.3) as described in the previous example. Nearly all of the eluted chimeric protein is released in the first 24 fractions. These fractions were pooled and contain 35.9 mg of chimeric protein and 82.6 mg of total protein, corresponding to a 776-fold purification with 71% recovery. This eluted pool of chimeric protein (called IA1) was found to contain 2.9 mg of total cholesterol per mg of chimeric protein.

24.4 mg of chimeric protein from pool IA1 was reapplied to the HTF-14 column (99.9% binding). Elution with 20 mM EDTA did not release significant amounts of chimeric protein (0.005% of total bound chimeric protein was released). Subsequent elution of chimeric protein with 0.1M glycine (pH 2.3), pooling of fractions in the major elution peak, and dialysis of the pool against PBS yielded a pool containing a total of 19.13 mg of chimeric protein (78% recovery). This eluted pool of chimeric protein (called IA2) was found to contain only 0.13 mg of total cholesterol per mg of chimeric protein. Thus, greater than 95% of cholesterol bound to the chimeric protein was removed by washing the column with 20 mM EDTA prior to glycine elution.

For further purification, the IA2 preparation of chimeric protein was applied to the human LDL ligand-affinity column in the presence of divalent cation, followed by elution with a molar excess of EDTA as in Example 7. The loaded material, depleted of bovine LDL, binds and elutes with greater overall recovery as compared to the material described in Example 7, in which column binding and recovery was inhibited due to bovine LDL bound to the chimeric protein.

Figure 6:
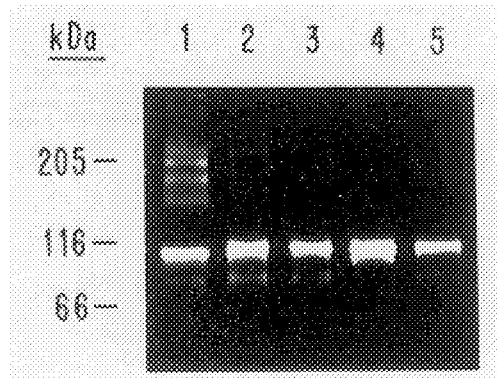
FIG. 6 shows the results of analysis by non-reducing SDS-PAGE and Western blot analysis of LDLR/TF chimeric protein forms, produced in Chinese hamster ovary (CHO) cells, at various stages of immunoaffinity (IA) purification.

FIG. 6 shows LDLR/TF chimeric protein forms, produced in CHO cells, at various stages of immunoaffinity (IA) purification and analyzed by non-reducing SDS/PAGE and Western blot analysis. Protein electroblotted to nitrocellulose is bound to peroxidase-conjugated anti-human transferrin antibody, followed by chemiluminescent detection of peroxidase. The major band is the LDLR/TF chimeric protein, while the smaller, minor band represents a product that has lost the LDLR binding domain.

Lane 1 shows concentrated conditioned medium from CHO cells expressing LDLR/TF chimeric protein. Lane 2 shows LDLR/TF chimeric protein purified from CHO cell supernatants by the method of Example 7. The material loaded is an aliquot of a pool of protein fractions eluted from the IA (MAb HTF-14) column. Lane 3 shows LDLR/TF chimeric protein pool of lane 2 after dialysis against TBS. Lane 4 shows LDLR/TF chimeric protein purified from CHO cell supernatants by the method described in Example 7. Concentrated conditioned medium was bound to and eluted from the anti-human transferrin immunoaffinity column, followed by binding to and elution from the human LDL ligand-affinity column. Note the depletion in the lower band of immunoreactive material. Lane 5 shows LDLR/TF chimeric protein purified from CHO cell supernatants by the method described in Example 8, in which the step for dissociating bound bovine LDL was included. Chimeric protein (IA1) from the pool shown in lane 3 was bound again to the IA column and then depleted of bound bovine LDL by washing the column in TBS containing 20 mM EDTA. Chimeric protein shown here (called IA2) represents a pool of protein fractions eluted from the IA column after the EDTA washing step. The material in lanes 1, 2, 3, and 5 was isolated from CHO cells grown in the presence of the serine protease inhibitor Pefablock SC.

EXAMPLE 9

Measurement of LDL Binding to LDLR/TF by an In Vitro Binding Assay

A microplate binding assay was developed in order to study the binding affinity of LDL for LDLR/TF. In this assay, human LDL is captured on the plate by chimeric protein bound to the plate via an anti-TF monoclonal antibody used to coat the wells. Human LDL is then detected by reaction with an anti-LDL antibody. This assay is dependent on the chimeric protein containing both the TF and LDLR domains.

Figure 7:
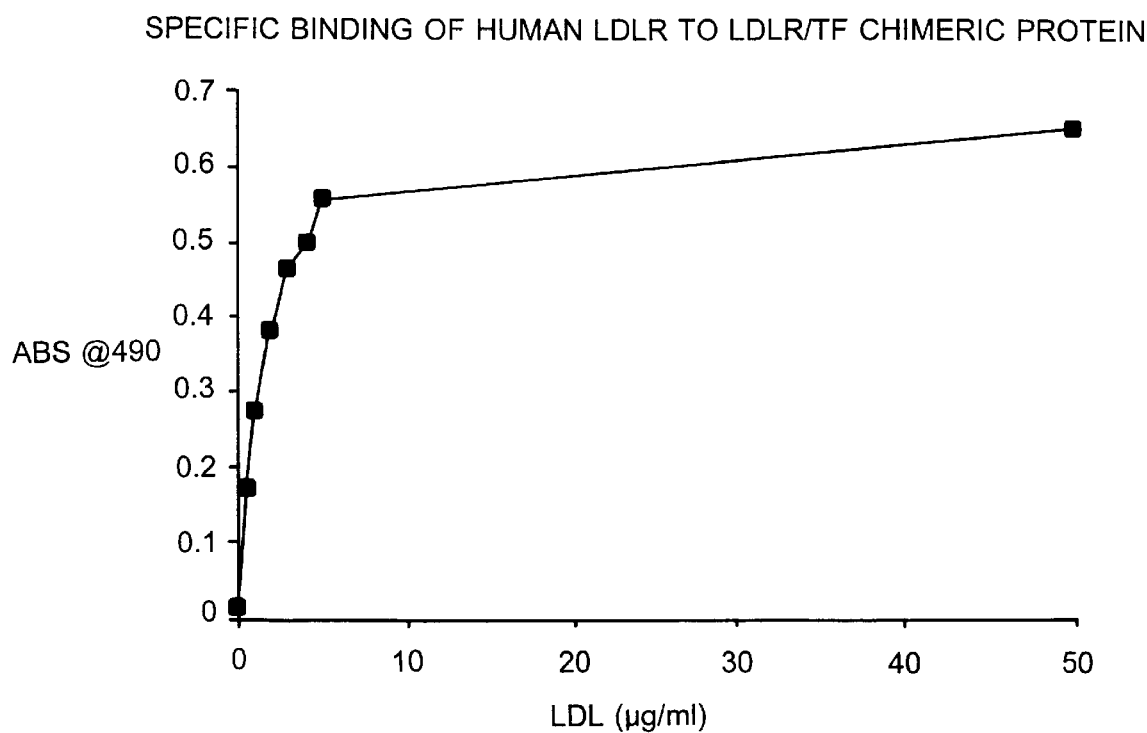
FIG. 7 is a graphic representation of specific binding of human LDL to LDLR/TF chimeric protein at the concentrations of LDL indicated.

A 96-well ELISA microplate was coated with MAb HTF-14 (1:500 in 50 mM Tris-HCl, 2 mM $CaCl_2$, pH 8.0) for 45 minutes at 37° C., after which the plate is washed 3 times in solution B (50 mM Tris-HCl, 2 mM $CaCl_2$, pH 8.0, 0.5% BSA, 0.05% Tween-20). Wells were incubated for 45 minutes at 37° C. in blocking solution (50 mM Tris-HCl, 2 mM $CaCl_{21}$ pH 8.0, 1% BSA, 0.05% Tween-20). Blocking solution was removed and replaced with various binding media and incubated for 30 minutes at 37° C. Binding media contained human LDL in solution B at concentrations between 0.5 µg/ml (0.97 nM apoB-100) and 50 µg/ml (97 nM apoB-100), and, in addition, either chimeric protein at 1.55 µg/ml (13.3 nM), human transferrin at 1 µg/ml (13.3 nM), or nothing added. The plate was washed 3 times with solution B and then incubated for 30 minutes at 37° C. with a sheep polyclonal Ab (IgG) specific for human LDL (1:1000 in solution B; Biomedical Technologies, Inc., BT-999). The plate was washed 3 times with solution B and then incubated for 20 minutes at 37° C. with a peroxidase-conjugated rabbit polyclonal Ab specific for sheep IgG (1:5000 in solution B; Cappel, 55814). The plate was washed 3 times with solution B and then incubated for 5 minutes at 37° C. with the peroxidase substrate 1,2-phenylenediamine (0.67 mg/ml in 0.1M citric acid-phosphate, pH 5.0). The reactions were stopped by the addition of $H_2SO_4$ to a final concentration of 0.8N, after which the absorbances at 490 nm were determined using a microplate reader. At each concentration of LDL, the signal obtained in binding media containing human transferrin was comparable to that obtained in the absence of transferrin or chimeric protein, and this is considered to constitute a background level of nonspecific binding. The mean absorbance due to nonspecific binding at each LDL concentration was subtracted from the signal obtained in the presence of chimeric protein to yield an absorbance value representing specific binding of LDL to chimeric protein. This absorbance value was plotted versus LDL concentration, as shown in the FIG. 7. Assuming that the signal at 50 µg/ml represents maximum binding, half-maximal binding was observed at approximately 1.6 µg/ml (3.1 nM) of LDL.

EXAMPLE 10

Binding and Dissociation Properties of LDLR/TF Chimeric Proteins

The LDL:LDLR interaction has been characterized in great detail, and shown to require $Ca^{++}$ or other divalent cations. Additionally, binding of the LDL ligand to the LDLR is dependent on pH, such that dissociation occurs at low pH (J. L. Goldstein and M. S. Brown, Ann. Rev. Biochem., 46:897 (1977)). This latter characteristic is important physiologically, allowing release of LDL by the LDLR into the acidic, endosomal compartment, and recycling of the receptor. Therefore, an in vitro assay, designed specifically to study the LDL:LDLR interaction, was used to study the pH and cation independence of LDL binding to and dissociation from the LDLR/TF chimeric protein.

LDLR/TF chimeric protein produced and purified as described in Example 8 was examined for its LDL binding properties. Specifically, the cation dependence of LDL binding to the LDLR domain of the chimeric protein was studied by examining binding in the presence and absence of EDTA. The cation dependence of LDL binding to the LDLR domain of the chimeric protein was studied by examining the effects of post-binding washing steps, performed in the presence and absence of EDTA. Similarly, the pH dependence of LDL binding to the chimeric protein was studied by examining the effects of pH 8.0 versus pH 5.2 conditions during the binding and post-binding wash steps, respectively. Decreased binding at low pH would indicate that LDL may be released from the LDLR/TF:TFR complex in the acidic environment of the endosome, permitting the recycling of the complex. A microplate binding assay was developed to examine these effects and the results are shown in FIG. 8.

The microplate binding assay detects the amount of chimeric protein bound to LDL immobilized on an ELISA plate coated with an anti-LDL antibody. A 96-well microtiter plate was coated with 5 µg/ml sheep anti-human LDL antibody (Biomedical Technologies, Inc., BT-999) in 50 mM Tris-HCl, pH 8.0, 2 mM $CaCl_2$ (solution A). After washing with solution A plus 0.5% BSA and blocking with solution A plus 1% BSA at 37° C. for 30 minutes. Sample wells that served as negative controls were not coated with the anti-human LDL antibody (no Ab). Unbound LDL was removed by washing with solution A plus 0.5% BSA. Since LDL:anti-LDL binding is expected to be insensitive to divalent cation concentration, certain control wells were washed instead with solution A plus 0.5% BSA and 20 mM EDTA (pre-wash in EDTA). Next, chimeric protein was added to all wells at a concentration of 1 µg/ml in solution A plus 0.5% BSA (untreated), and incubated at 37° C. for 30 minutes. Some wells were treated with chimeric protein in solution A plus 0.5% BSA and 20 mM EDTA (binding in EDTA), while others were treated with chimeric protein in a pH 5.2 buffer containing 25 mM sodium acetate, 150 mM NaCl, and 2 mM $CaCl_2$ (binding in pH 5.2). Sample wells were then washed with one of three solutions: 1) solution A plus 0.5% BSA (untreated), 2) solution A, plus 0.5% BSA and 20 mM EDTA (wash in EDTA), or 3) 25 mM sodium acetate (pH 5.2), 150 mM NaCl, 2 mM $CaCl_2$ (wash in pH 5.2). Wells were then incubated with an HRP-conjugated sheep anti-human transferrin antibody (Biodesign K90070P, 1:5000 dilution in solution A plus 0.5% BSA), incubated for 30 minutes at 37° C., followed by thorough washing with solution A, plus 0.5% BSA untreated). Some wells were washed with solution A, plus 0.5% BSA and 20 mM EDTA (post-HRP wash in EDTA), while others were washed in 25 mM sodium acetate (pH 30 5.2), 150 mM NaCl, 2 mM $CaCl_2$ (post-HRP wash in pH 5.2). The final wash step was followed by development with the substrate ortho-phenylenediamine for 5 minutes at 37° C. After addition of 2N $H_2SO_4$ to stop the reaction, the plate was analyzed for absorbance at 490 nm.

As seen in FIG. 8, the binding of chimeric protein to the plate (untreated) is entirely dependent on the presence of plate-bound LDL, since lack of coating antibody (anti-LDL) resulted in only a background level of chimeric protein binding (no Ab). Moreover, EDTA did not significantly dissociate LDL bound to the coating antibody, as demonstrated by the small effect on the final chimeric protein binding signal (pre-wash in EDTA).

Chimeric protein binding to plate-immobilized LDL was dramatically reduced to background or near-background levels if this binding step was carried out in the presence of a 10-fold molar excess of EDTA over $Ca^{++}$ (binding in EDTA) or under acidic conditions (binding in EDTA) or under acidic conditions (binding in pH 5.2). This shows that the chimeric protein:LDL binding interaction is dependent on the presence of unchelated divalent cations and is pH-sensitive, similar to the LDL:LDLR binding interaction observed in vitro and in vivo.

Following chimeric protein binding under permissive conditions, subsequent wash steps performed in either EDTA (wash in EDTA) or under acidic conditions (wash in pH 5.2) were effective in dissociating chimeric protein from LDL to background or near-background levels. These results suggest that the chimeric protein can release its bound LDL under acidic conditions, as observed for LDLR in vitro and in vivo.

Following chimeric protein binding, washing, and binding to the HRP-conjugated anti-human transferrin antibody, subsequent wash steps performed in either EDTA (post-HRP wash in EDTA) or under acidic conditions (post-HRP wash in pH 5.2) were only partially effective in dissociating chimeric protein from LDL. Thus, these results demonstrate that the effects of pH and EDTA are due to dissociation of LDL:chimeric protein complexes, and not to inhibition of binding of HRP-conjugated anti-human transferrin antibody to the TF domain in pre-formed LDL:chimeric protein complexes. Furthermore, these results suggest that binding of the antibody to the TF domain of the chimeric protein has an allosteric effect on the LDLR domain (causing increased LDL affinity), or perhaps causes a steric hindrance towards dissociation reagents (causing increased stabilization of the LDL:chimeric protein complex under dissociation conditions).

EXAMPLE 11

LDLR/TF Chimeric Proteins Expressed in Mammalian Cells Contain Intact LDLR and TF Structural Domains This example describes work demonstrating that a single LDLR/TF chimeric protein contains both LDLR and TF structural domains which, based on the known specificities of the MAbs used, indicates that these structural regions retain functional binding activity for LDL and TFR, respectively.

LDLR/TF chimeric proteins are expressed in transfected mammalian cells from a fusion gene consisting of a 5' human LDLR cDNA sequence (374 amino acid ligand-binding domain) fused in frame at its 3' end with the entire cDNA sequence encoding mature human transferrin. To demonstrate that the chimeric protein retains the structural features found in the natural LDLR and TF proteins, we show here that the LDLR/TF chimeric protein species can be immunoprecipitated by two different MAbs: HTF-14 (anti-human TF, Biodesign H61061M) and C7 (anti-human LDLR, Amersham RPN 537).

MAb HTF-14 is known to react specifically with a conformational (and non-reduced) epitope on human TF that maps at or near the TFR binding site. Binding of HTF-14 to TF inhibits TFR binding. The binding of MAb HTF-14 to LDLR/TF chimeric protein constitutes evidence that the TF domain of the chimeric protein is largely intact and suggests that this conformation in LDLR/TF will also have TFR binding activity. Example 12 presents data demonstrating that the LDLR/TF chimeric protein does in fact bind to human TFRS.

MAb C7 is known to react specifically with the ligand-binding domain of human LDLR at or near the LDL (ligand)-binding site. The binding of C7 to LDLR inhibits LDL binding and, conversely, the binding of LDL to LDLR inhibits C7 binding. The binding of MAb C7 to LDLR/TF chimeric protein constitutes evidence that the LDLR domain of the chimeric protein is largely intact and suggests that this site in LDLR/TF will also have LDL-binding activity. Other experiments (Example 9) have shown that the LDLR/TF chimeric protein does in fact bind to human LDL.

Figure 9:
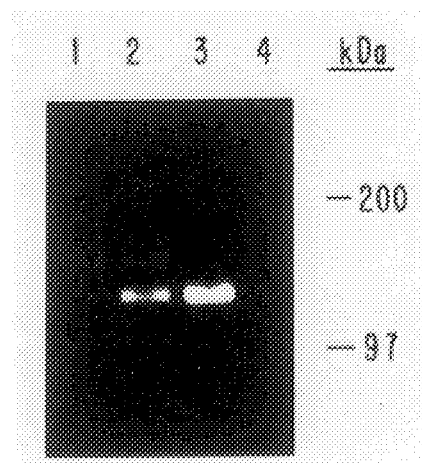
FIG. 9 shows the results of Western blot analysis of LDLR/TF chimeric proteins.

One ml of conditioned media from normal human fibroblast clones transfected with either pSV2neo (negative control) or co-transfected with pEFBPS/LDLrTF1.S and pSV2neo was first pre-cleared with goat anti-mouse IgG agarose beads (Hyclone EGK-1060) in TBS containing 1% NP-40, followed by the addition of either MAb HTF-14, MAb C7, or an unrelated MAb (anti-human factor IX, Hematologic Technologies, Inc. AHIX-5041). After antibody binding, antigen-antibody complexes were precipitated by addition of goat anti-mouse IgG agarose beads. The beads were washed to remove unbound material and proteins were eluted from the beads by boiling with SDS/PAGE sample buffer containing SDS. Eluates were run on SDS/PAGE (8% gel), electroblotted to a supported nitrocellulose membrane filter (Schleicher and Schuell BA-S-85), and the filter was blocked for several hours in TBS containing 0.05% Tween-20 and 5% (w/v) nonfat dry milk. The blocked filter was treated with HRP-conjugated sheep anti-human TF (Biodesign K90070P), which detects protein species carrying a variety of human TF epitopes, including that recognized by HTF-14. Antibody binding is performed here in TBS containing 0.05% Tween-20. After the binding step, the filter was washed several times in TBS with 0.05% Tween-20 followed by two washes with TBS. Following detection of the HRP conjugate with chemiluminescence reagents (Amersham RPN 2106), the film was exposed, processed, and scanned (FIG. 9). Lane 1 contains 1 ml of conditioned medium from the negative control human fibroblast clone (SV2neo-transfected) immunoprecipitated with MAb HTF-14. There are no chimeric protein species present. The material observed in lane 1 is not seen when 2% nonfat dry milk is used in the binding medium, and is thus not likely to be related to the chimeric protein. Lane 2 contains 1 ml of conditioned medium from a human fibroblast clone co-transfected with pEFBOS/LDLRrTF1.S and pSV2neo and immunoprecipitated with MAb HTF-14. A major protein species (approximately 116 kd) and one minor species (approximately 100 kd) is evident. The minor species is derived from the major species by a specific serine protease cleavage event in the LDLR domain. Lane 3 contains 1 ml of conditioned medium from the same human fibroblast clone used in lane 2, but immunoprecipitated with MAb C7. A major protein species (approximately 116 kd) is evident which has the same molecular size as the major product immunoprecipitated by MAb HTF-14. This indicates that a single LDLR/TF chimeric protein contains both an LDLR domain (immunoprecipitable with C7) and a TF domain (Detectable with HTF-14 in the Western blot analysis). MAb C7 does not immunoprecipitate the minor product seen in lane 3, which retains an intact TF domain but lacks an intact LDLR domain. Lane 4 contains 1 ml of conditioned medium from the same human fibroblast clone shown in lanes 2 and 3, but immunoprecipitated with a MAb specific for human factor IX, which is not known to bind to either LDLR or TF. As expected, the LDLR/TF chimeric protein is not immunoprecipitated by this antibody.

EXAMPLE 12

Binding of LDLR/TF Chimeric Protein to Transferrin Receptors on Human Hepatic Cells In Vitro The LDLR/TF chimeric protein purified as described in Example 8 has been tested for functionality by its ability to bind to the transferrin receptor (TFR) present on the surface of human hepatic cells. As described in this example, the LDLR/TF chimeric protein blocks TF binding to cells, indicating that it binds the transferrin receptor on human hepatic cells. Hep G2 cells are useful for in vitro studies of hepatocytes since they synthesize most of the proteins normally made by hepatocytes in normal human liver, including the TFR.

Hep G2 cells (ATCC number HB 8065) were grown in medium consisting of (DMEM, Cellgro 50-013), 10% fetal bovine serum (Hyclone A-1111), and 50 units/ml each of penicillin and streptomycin (GibcoBRL 15070-014). Radiolabeled transferrin ligand was obtained from Amersham (IM 194) as (3-[$^{125}$I]iodotyrosyl)-transferrin (human), at a specific activity of 700–800 Ci/mmol. This $^{125}$I-TF is iron-saturated (i.e. holo TF) and was dissolved in a binding medium containing 80% DMEM (Cellgro 50-013), 0.5% protease-free bovine albumin (Sigma A-3059), and 20% phosphate-buffered saline (PBS; GibcoBRL 14200–026). Inhibitors of radiolabeled TF binding were diluted in PBS and added to binding medium by substituting for the PBS component. In this example, chimeric protein and unlabeled holo TF were tested for inhibitory activity.

Hep G2 cells were plated into wells of 6-well tissue culture plates (35 mm diameter) at 2×10$^5$ cells per well and grown for 3 days. Cells were then washed one to two times with DMEM and subsequently incubated at 37° C. with 5 ml of DMEM for 30 minutes. This washing and incubation step helps remove serum components introduced with the fetal bovine serum, including transferrin, that might otherwise be bound to TFR and interfere with the binding assay. After the 30 minute incubation, the plates were placed on ice and the medium removed by aspiration. Each well received one ml of ice-cold binding medium and the plates were agitated slowly by shaking or rocking at 4° C. for 2 hours at (the binding period).

After the 2 hr. binding period, the plates were placed on ice and kept on ice during subsequent washing steps. To remove unbound label from the cells, each well was washed 3 times with PBS containing 0.5% BSA, followed by an additional 3 washes in PBS. The cells in each well were then lysed with 1 ml of 1N NaOH and the lysates transferred to 12×75 mm polystyrene tubes (Falcon 2052). The wells were washed with an additional 1 ml of 1N NaOH, which was added to the tube containing the appropriate lysate. The amount of radioactive TF present in the lysates was determined by quantification of gamma emission in a gamma counter (Beckman). Since placing the cells on ice at the conclusion of the binding period blocks uptake of labeled TF into the cells, the gamma emissions counted reflect the amounts of labeled TF on the surface of the cells at the end of the binding period. Lysates were also neutralized and assayed for total protein content using the BCA Protein Assay (Pierce 23225G), with bovine albumin used as a standard. The ratio of total radioactivity (expressed as counts per minute; cpm) to total protein content (in milligrams) gives a good estimate of ligand binding capacity.

The equilibrium dissociation constant ($K_d$) for TF binding to TFR in Hep G2 cells is 7 nM (Trowbridge, I. S. et al., *Biochem. Pharmacol.*, 33:925–993 (1984)). If unlabeled TF is present at 7 nM as a competitive inhibitor of $^{125}$I-TF binding to TFR, ligand binding (in cpm/mg) will be inhibited approximately 50%. Furthermore, if any unlabeled ligand (present at a concentration of approximately 7 nM) can bind to TFR with an affinity comparable to that of TF (e.g. LDLR/TF), 50% inhibition of binding will be observed. At high concentrations of unlabeled ligand (e.g. 50- or 100-fold higher than the $K_d$), nearly all receptor binding sites will be occupied and the only ligand bound to the cells should be that bound to nonspecific sites (i.e. sites other than the TFR). If an unlabeled ligand does not bind to TFR, no binding inhibition will be observed. Thus, human LDL, which does not interact directly with the TFR, does not display inhibition of TFR binding to $^{125}$I-TF.

This ligand-binding assay has been used to show that LDLR/TF chimeric proteins exhibit competitive inhibition of TFR binding to $^{125}$I-TF in Hep G2 cells and therefore can bind specifically to the human TFR.

In one experiment, Hep G2 cells were incubated with either no inhibitor or holo TF or purified LDLR/TF chimeric protein [purified from CHO cells expressing the LDLR/TF chimeric protein with amino acids 1–395 of human LDLR fused to amino acids 20–698 of human transferrin (see Example 3)] to assess the inhibitory effect these proteins. Holo TF and chimeric protein were tested at concentrations of 5 nM, 50 nM, or 500 nM with 10 $\mu$M FeCl$_3$ in an attempt to further saturate the iron-binding sites of TF or LDLR/TF chimeric protein. The results are shown in Table 2 (below):

TABLE 2

| | Binding (cpm bound per mg total protein in lysate) of $^{125}$I-holo TF$^a$ to Hep G2 cells$^b$ | | | |
|---|---|---|---|---|
| INHIBITOR | 0 nM | 5 nM | 500 nM | 500 nM/10 $\mu$M FeCl$_3$ |
| None | 62,856 | — | — | — |
| holo TF | — | 33,602 (53%) | 1,026 (2%) | 1,160 (2%) |
| LDLR/TF chimeric protein | — | 73,982 (117%) | 3,363 (5%) | 2,724 (4%) |

The numbers in parentheses denote percentage of counts bound relative to binding in the absence of inhibitor (set at 100%).
$^a$0.32 nM labeled TF
$^b$35 mm wells seeded at 2 × 10$^5$ cells These results show that both holo TF and LDLR/TF chimeric proteins were potent inhibitors of labeled TF binding. This ligand-binding assay thus demonstrates that LDLR/TF chimeric proteins exhibit competitive inhibition of TFR binding to $^{125}$I-TF in Hep G2 cells and therefore can bind specifically to the human TFR.

A similar assay can be used to show that chimeric proteins can also bind to TFR present on the surface of human fibroblasts and other cell types.

EXAMPLE 13

Uptake of LDL into Human Hepatic Cells In Vitro

The LDLR/TF chimeric protein purified as in the previous examples can be tested for the ability to bind both to human LDL and to human TFR in such a way as to enhance cellular uptake of LDL via a TFR-mediated pathway. Moreover, the additional LDL uptake afforded by the chimeric protein can be inhibited by competition with TF.

To quantify LDL uptake in the Hep G2 cell line, cells are exposed to binding medium, washed, lysed, and assayed for radioactivity and total protein content in much the same way as described for TFR binding in Example 12. In this assay, however, radioactively-labeled LDL is used and its uptake into cells after binding is studied by incubation at 37° C. During the incubation period, labeled LDL binds to LDLR and enters the cell via the normal LDLR pathway. In addition, labeled LDL can also bind to chimeric protein, and the LDLR/TF-LDL complex enters the cell after binding to the TFR and uptake via the TFR pathway. Thus, unlabeled LDL inhibits binding of labeled LDL to both LDLR and chimeric protein, while human holo TF only inhibits binding of LDLR/TF-LDL complex to the TFR.

Radiolabeled ($^{125}$I) human LDL (Biomedical Technologies, Inc.; BT-913R) at a specific activity of greater than 200 cpm per ng of LDL protein is diluted in medium containing 80% DMEM, 0.5% protease-free bovine albumin, and 20% PBS. Inhibitors of radiolabeled LDL binding and uptake are diluted in PBS and added to this medium by substituting for the PBS component. In this example, uptake of $^{125}$I-LDL is measured in the presence or absence of chimeric protein and in the presence or absence of unlabeled inhibitors holo human TF (Sigma T-3400) or LDL (Biomedical Technologies, Inc. BT-903).

Hep G2 cells are plated into wells of 6-well tissue culture plates (35 mm diameter) at $2 \times 10^5$ cells per well and grown for 3 days in medium consisting of DMEM (Cellgro 50-013), 10% fetal bovine serum (Hyclone A-1111), and 50 units/ml each of penicillin and streptomycin (GibcoBRL 15070-014). Cells are then washed one to two times with DMEM and incubated at 37° C. with 5 ml of DMEM for 30 minutes. This washing and incubation step helps remove serum components introduced with the fetal bovine serum, including transferrin, that might otherwise be bound to TFR and interfere with the binding assay. After the 30 min. incubation, the medium in each well is removed by aspiration and replaced with one ml of uptake medium. The plates are placed at 37° C. in a standard tissue-culture incubator to allow uptake and accumulation of the labeled LDL.

After the uptake period, the plates are placed on ice and kept on ice during subsequent washing steps. To remove unbound label from the cells, each well is washed 3 times with PBS containing 0.5% BSA, followed by an additional 3 washes in PBS. The cells in each well are then lysed with 1 ml of 1N NaOH and the lysates transferred to 12×75 mm polystyrene tubes (Falcon 2052). The wells are washed with an additional 1 ml of 1N NaOH which is added to the tube containing the appropriate lysate. The amount of radiolabeled LDL present in the lysates is determined by quantification of gamma emission in a gamma counter (Beckman). Because the cells internalize labeled LDL, the emissions counted reflect the amounts of labeled LDL or its metabolites inside the cells, as well as the amounts of intact labeled LDL on the surface of the cells at the end of the uptake period. Lysates are also neutralized and assayed for total protein content by BCA Protein Assay (Pierce 23225G). The ratio of total radioactivity (cpm) to total protein content (mg) gives a good estimate of LDL uptake. This assay can be used to show that the LDLR/TF chimeric protein promotes enhanced uptake of radiolabeled LDL into Hep G2 cells and that unlabeled TF or LDL acts as a competitive inhibitor of this enhanced uptake.

The uptake of LDL into cells can also be monitored by measuring the effects of internalized LDL on intracellular processes and gene expression, using established protocols (Goldstein, J. L. et al., *Meth. Enzymol.*, 98:241–260 (1983)). Release of free cholesterol from LDL directly or by hydrolysis of cholesteryl esters results in a regulatory pool of cholesterol that not only suppresses the expression the gene encoding 3-hydroxy-3-methylglutaryl-CoA reductase (HMG-CoA reductase), but also activates expression of the gene encoding acyl-CoA:cholesterol O-acyltransferase (ACAT). Since HMG-CoA reductase catalyzes the rate-limiting step in cholesterol biosynthesis, down regulation of the gene encoding this enzyme reduces the de novo biosynthesis of cholesterol as the levels of intracellular cholesterol increase due to uptake stimulated by LDLR/TF. In addition, increased expression of ACAT, an enzyme that esterifies excess free cholesterol to allow storage in the cytoplasm as cholesteryl ester droplets (principally cholesteryl oleate), results in an increased capacity for storage of cholesterol by cells. Finally, synthesis of LDLRs is down regulated by an increase in the regulatory pool of free cholesterol. Thus, these three secondary effects of increasing intracellular pools of cholesterol on cholesterol metabolism constitute a mechanism of cholesterol homeostasis which protects the organism against overproduction of cholesterol.

When LDL-uptake occurs as a result of the chimeric protein functioning in the TFR-mediated endocytosis pathway, the free cholesterol released does not down-regulate the synthesis of TFRs as it does the synthesis of LDLRs. The effect of this down-regulation would lead ultimately to decreased intracellular cholesterol (because of decreased uptake due to lower numbers of LDLRs) which subsequently leads to increased cholesterol biosynthesis due increased activity of HMG-CoA reductase and decreased ability to store cholesterol due to decreased ACAT activity. Continual uptake of LDL can occur in the presence of chimeric protein via the TFR-mediated endocytosis pathway, resulting in continuous suppression of HMG-CoA reductase and continuous activation of ACAT. Thus, in bypassing the normal LDL uptake pathway, the decrease and increase in biosynthesis and storage, respectively, of intracellular cholesterol can be maintained over long periods leading to sustained reduced total serum cholesterol levels.

EXAMPLE 14

Effect of LDLR/TF Chimeric Protein on In Vivo Mouse Cholesterol Levels

To determine whether the LDLR/TF chimeric protein has an anti-hypercholesterolemic effect in an in vivo model system, an intravenous injection of purified chimeric protein is performed and cholesterol levels are measured at one or more time intervals post-injection. Because an exogenously administered protein such as LDLR/TF will have a finite circulating lifetime in an animal, a bolus injection should have only a transient effect in reducing levels of LDL cholesterol, with levels returning to baseline once the injected protein is removed from the circulation. However, continuous delivery of chimeric protein by means of a slow-release device or by gene therapy (implantation of cells genetically engineered to secrete chimeric protein) can have a long-term or permanent effect on LDL cholesterol.

Ishibashi et al. (*J. Clin. Invest.* 92:883–893 (1993)) describe an LDLR-knockout mouse that has increased levels of both total cholesterol and LDL cholesterol as compared to most strains of experimental mice. This mouse strain, which contains a homozygous deletion of the LDLR gene, is used for in vivo studies of the biological effects of LDLR/TF in a mammalian species.

In normal mice, most circulating cholesterol is carried by HDL, while in humans most of the cholesterol is carried by LDL. Unlike humans, however, 70% of the LDL fraction in mice is associated with apoB-48, a truncated variant of apolipoprotein B lacking binding sites for LDLR, while 30% is associated with apoB-100, which contains the LDLR binding region. By contrast, 98% of human LDL contains apoB-100. In terms of weight percentages, mouse LDL contains 9.5% unesterified cholesterol, 23.5% cholesteryl esters, and 20.5% protein; human LDL contains 9.2% unesterified cholesterol, 37% cholesteryl esters, and 22% protein (Chapman, M., *J. Meth. Enzymol.* 128:70–143 (1986)).

The effect of a homozygous deletion of the LDLR gene is to abolish the clearance of LDL (apoB-100), resulting in a higher steady-state level of LDL. Homozygous female LDLR-knockout mice have total cholesterol levels that are 139 mg/dl higher than in the normal homozygous wild-type controls (Ishibashi et al. (*J. Clin. Invest.* 92:883–893 (1993)). Since functional LDLR interacts with the apoB-100 LDL fraction but not the apoB-48 LDL fraction, and assuming that the excess 139 mg/dl of total cholesterol is contained exclusively in the ApoB-100 LDL fraction, the approximately 1 ml of serum in each mouse contains at least 1.39 mg of total cholesterol in the apoB-100 LDL fraction, the target molecule for LDLR/TF binding. Assuming that cholesterol comprises 33% of LDL by weight, that this fraction is 20.5% protein, and that the apoB-100 molecule has a molecular weight of 514 kd, then 1.39 mg of total cholesterol corresponds to approximately 1.68 nmol of apoB-100 per mouse (one apoB-100 molecule per LDL particle). For unimolecular binding to LDLR/TF (which has a molecular weight of 116.3 kd excluding carbohydrate), 1.68 nmol of LDLR/TF corresponds to 195 µg of LDLR/TF per mouse. To deliver LDLR/TF in an amount equal to, for example, 10% of the number of LDL (apoB-100) particles circulating in the LDLR-knockout mouse (0.168 nmol) requires injection of 19.5 µg of LDLR/TF fusion protein per mouse.

To establish baseline levels of total cholesterol, HDL cholesterol, and LDL cholesterol, retro-orbital bleeds are performed on anesthetized animals at certain times prior to injection with chimeric protein or negative controls. In each animal, serum is isolated from clotted blood and tested for levels of total cholesterol and HDL cholesterol, using a coupled enzymatic assay with colorimetric endpoint (Sigma Chemical Co., St. Louis, Mo.). Total cholesterol concentration in mg/dl is quantified by adapting the manual procedure to a 96-well microtiter plate format. Sera and cholesterol standards are diluted in normal saline solution and 10 µl of each are loaded into duplicate or triplicate wells of a 96-well microtiter plate. 200 µl of Cholesterol Reagent (Sigma 352-20) are added to each well and the plate is incubated at 37° C. for 10 minutes, after which the absorbance at 490 nm is read on a microplate reader. In this assay, absorbance is linear between 0 and 200 mg/dl (standard curve generated with cholesterol standards; Sigma C-0534) and samples may be diluted to fall within this range.

HDL cholesterol concentration in mg/dl is quantified as total cholesterol (performed as above) following precipitation of LDL and VLDL cholesterol fractions with HDL Cholesterol Reagent (Sigma 352-3). Serum is mixed with one-tenth volume of HDL Cholesterol Reagent and allowed to stand at room temperature for approximately 5 minutes. Following centrifugation in a microcentrifuge for 2 minutes at high speed, a portion of the supernatant is removed, diluted in normal saline, and assayed for total cholesterol by the above method. To obtain the HDL cholesterol concentration in the original serum, the total cholesterol concentration in the assayed supernatant is multiplied by 1.1 to account for the 10% increase in volume due to addition of HDL Cholesterol Reagent. LDL cholesterol is calculated by subtracting the value obtained for HDL cholesterol from the total cholesterol value obtained prior to treatment of serum with the HDL Cholesterol Reagent and removal of the LDL and VLDL fractions.

After pre-injection baseline levels of serum cholesterol have been determined, 50 µl each of an appropriate amount of LDLR/TF chimeric protein (in phosphate-buffered saline; PBS) is injected into the tail veins of anesthetized LDLR-knockout mice. To assess the effects of anesthesia and injection, 50 µl of PBS is injected into different LDLR-knockout animals as negative controls. To determine if interaction of the TF receptor with administered TF domains affects lipoprotein metabolism, 50 µl of a PBS solution containing human holotransferrin (holo TF) at the same molar concentration as LDLR/TF is injected into LDLR-knockout animals as additional negative controls. Human holo TF contains the same TF domain as contained in the LDLR/TF chimeric protein, but lacks the LDLR domain and cannot bind LDL. This type of negative control permits evaluation of any effects that may result from injection of an equivalent amount of a human protein or human TF antigen.

Following injections of chimeric protein or negative-control substances, retro-orbital bleeds are performed again at time intervals appropriate for the given volume and frequency of sampling. Sera from post-injection bleeds are assayed for the concentrations of total cholesterol and HDL cholesterol. Levels of LDL (i.e. LDL plus VLDL) cholesterol are calculated as the arithmetic difference between total cholesterol and HDL cholesterol concentrations. In this manner, the effect that LDLR/TF has on decreasing specific serum cholesterol fractions may be quantified.

Sera from post-injection bleeds can also be assayed for the concentration of LDLR/TF chimeric protein remaining in the circulation. The human TF ELISA (Example 6) can be used, since the antibodies employed in the assay do not cross-react with mouse transferrin. Measurement of the rate of disappearance of chimeric protein in mouse sera allows an estimation of the circulating half-life of chimeric protein.

The effects of specific chimeric proteins on lipoprotein clearance rates can also be studied. Ishibashi et al. (*J. Clin. Invest.* 92:883–893 (1993) have shown that loss of the LDLR in mice reduces significantly the rate of clearance of injected radiolabeled LDL or VLDL, but does not alter the clearance rate of injected radiolabeled HDL. Clearance rates following chimeric protein delivery (bolus or continuous infusion) can be studied in this way in order to quantify the increase in lipoprotein clearance rate resulting from administration of the chimeric protein.

In addition to the LDLR knockout mouse, the Watanabe rabbit, which has defective LDL receptors and hypercholesterolemia due to defective LDL metabolism, may be used to assess the in vivo effects of the LDLR/TF chimeric protein on cholesterol levels.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric protein comprising a functional domain and a carrier domain, wherein the functional domain comprises an amino acid sequence of a ligand-binding domain of a human low density lipoprotein receptor which binds low density lipoprotein cholesterol and the carrier domain comprises an amino acid sequence of human transferrin which binds a human transferrin receptor.

2. DNA encoding a chimeric protein comprising a functional domain and a carrier domain, wherein the functional domain comprises an amino acid sequence of a ligand-binding domain of a human low density lipoprotein receptor which binds low density lipoprotein cholesterol and the carrier domain comprises an amino acid sequence of human transferrin which binds a human transferrin receptor.

3. An expression plasmid comprising:

a) a promoter;

b) DNA encoding a chimeric protein comprising a functional domain and a carrier domain, wherein the functional domain comprises an amino acid sequence of a ligand-binding domain of a human low density lipoprotein receptor which binds low density lipoprotein cholesterol and the carrier domain comprises an amino acid sequence of human transferrin which binds a human transferrin receptor, wherein expression of the DNA encoding the chimeric protein is under the control of the promoter.

4. A genetically modified mammalian cell which expresses DNA encoding a chimeric protein, wherein the chimeric protein comprises a functional domain and a carrier domain, wherein the functional domain comprises an amino acid sequence of a ligand-binding domain of a human low density lipoprotein receptor which binds low density lipoprotein and the carrier domain comprises an amino acid sequence of human transferrin which binds a human transferrin receptor.

5. The genetically modified mammalian cell of claim 4, wherein the mammalian cell is selected from the group consisting of: human cells, porcine cells, hamster cells, bovine cells, canine cells, mouse cells, rat cells, monkey cells, feline cells, rabbit cells, sheep cells and chimpanzee cells.

6. The genetically modified human cell of claim 5, wherein the human cell is selected from the group consisting of: human fibroblasts, human keratinocytes, human epithelial cells, human ovary cells, human endothelial cells, human glial cells, human neural cells, formed elements of the blood, human muscle cells, human hepatocytes and precursors of these human cell types.

7. The genetically modified mammalian cell of claim 5, wherein the mammalian cells are Chinese hamster ovary cells.

8. The genetically modified mammalian cell of claim 5, wherein the cell is an immortalized cell.

9. The genetically modified human cell of claim 6, wherein the cell is a primary cell or a secondary cell.

10. A pharmaceutical composition comprising the chimeric protein of claim 1.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 3427 base pairs
        ( B ) TYPE: nucleic acid
        ( C ) STRANDEDNESS: both
        ( D ) TOPOLOGY: both ( i i ) MOLECULE TYPE: cDNA to mRNA ( x i ) SEQUENCE DESCRIPTION: SEQ ID NO:1:

| | | | | | | |
|---|---|---|---|---|---|---|
| AGAGGCTGCG | AGCATGGGGC | CCTGGGGCTG | GAAATTGCGC | TGGACCGTCG | CCTTGCTCCT | 60 |
| CGCCGCGGCG | GGGACTGCAG | TGGGCGACAG | ATGTGAAAGA | AACGAGTTCC | AGTGCCAAGA | 120 |
| CGGGAAATGC | ATCTCCTACA | AGTGGGTCTG | CGATGGCAGC | GCTGAGTGCC | AGGATGGCTC | 180 |
| TGATGAGTCC | CAGGAGACGT | GCTTGTCTGT | CACCTGCAAA | TCCGGGGACT | TCAGCTGTGG | 240 |
| GGGCCGTGTC | AACCGCTGCA | TTCCTCAGTT | CTGGAGGTGC | GATGGCCAAG | TGGACTGCGA | 300 |
| CAACGGCTCA | GACGAGCAAG | GCTGTCCCCC | AAGACGTGC | TCCCAGGACG | AGTTTCGCTG | 360 |
| CCACGATGGG | AAGTGCATCT | CTCGGCAGTT | CGTCTGTGAC | TCAGACCGGG | ACTGCTTGGA | 420 |
| CGGCTCAGAC | GAGGCCTCCT | GCCCGGTGCT | CACCTGTGGT | CCCGCCAGCT | TCCAGTGCAA | 480 |
| CAGCTCCACC | TGCATCCCCC | AGCTGTGGGC | CTGCGACAAC | GACCCCGACT | GCGAAGATGG | 540 |
| CTCGGATGAG | TGGCCGCAGC | GCTGTAGGGG | TCTTTACGTG | TTCCAAGGGG | ACAGTAGCCC | 600 |
| CTGCTCGGCC | TTCGAGTTCC | ACTGCCTAAG | TGGCGAGTGC | ATCCACTCCA | GCTGGCGCTG | 660 |
| TGATGGTGGC | CCCGACTGCA | AGGACAAATC | TGACGAGGAA | AACTGCGCTG | TGGCCACCTG | 720 |
| TCGCCCTGAC | GAATTCCAGT | GCTCTGATGG | AAACTGCATC | CATGGCAGCC | GGCAGTGTGA | 780 |
| CCGGGAATAT | GACTGCAAGG | ACATGAGCGA | TGAAGTTGGC | TGCGTTAATG | TGACACTCTG | 840 |
| CGAGGGACCC | AACAAGTTCA | AGTGTCACAG | CGGCGAATGC | ATCACCCTGG | ACAAAGTCTG | 900 |
| CAACATGGCT | AGAGACTGCC | GGGACTGGTC | AGATGAACCC | ATCAAAGAGT | GCGGGACCAA | 960 |
| CGAATGCTTG | GACAACAACG | GCGGCTGTTC | CCACGTCTGC | AATGACCTTA | AGATCGGCTA | 1020 |
| CGAGTGCCTG | TGCCCCGACG | GCTTCCAGCT | GGTGGCCCAG | CGAAGATGCG | AAGATATCGA | 1080 |
| TGAGTGTCAG | GATCCCGACA | CCTGCAGCCA | GCTCTGCGTG | AACCTGGAGG | GTGGCTACAA | 1140 |
| GTGCCAGTGT | GAGGAAGGCT | TCCAGCTGGA | CCCCCACACG | AAGGCCTGCA | AGGCTGTGGT | 1200 |
| CCCTGATAAA | ACTGTGAGAT | GGTGTGCAGT | GTCGGAGCAT | GAGGCCACTA | AGTGCCAGAG | 1260 |
| TTTCCGCGAC | CATATGAAAA | GCGTCATTCC | ATCCGATGGT | CCCAGTGTTG | CTTGTGTGAA | 1320 |
| GAAAGCCTCC | TACCTTGATT | GCATCAGGGC | CATTGCGGCA | AACGAAGCGG | ATGCTGTGAC | 1380 |
| ACTGGATGCA | GGTTTGGTGT | ATGATGCTTA | CTTGGCTCCC | AATAACCTGA | AGCCTGTGGT | 1440 |
| GGCAGAGTTC | TATGGGTCAA | AAGAGGATCC | ACAGACTTTC | TATTATGCTG | TTGCTGTGGT | 1500 |
| GAAGAAGGAT | AGTGGCTTCC | AGATGAACCA | GCTTCGAGGC | AAGAAGTCCT | GCCACACGGG | 1560 |
| TCTAGGCAGG | TCCGCTGGGT | GGAACATCCC | CATAGGCTTA | CTTTACTGTG | ACTTACCTGA | 1620 |
| GCCACGTAAA | CCTCTTGAGA | AAGCAGTGGC | CAATTTCTTC | TCGGGCAGCT | GTGCCCCTTG | 1680 |
| TGCGGATGGG | ACGGACTTCC | CCCAGCTGTG | TCAACTGTGT | CCAGGGTGTG | GCTGCTCCAC | 1740 |
| CCTTAACCAA | TACTTCGGCT | ACTCGGGAGC | CTTCAAGTGT | CTGAAGGATG | GTGCTGGGGA | 1800 |
| TGTGGCCTTT | GTCAAGCACT | CGACTATATT | TGAGAACTTG | GCAAACAAGG | CTGACAGGGA | 1860 |
| CCAGTATGAG | CTGCTTTGCC | TAGACAACAC | CCGGAAGCCG | GTAGATGAAT | ACAAGGACTG | 1920 |
| CCACTTGGCC | CAGGTCCCTT | CTCATACCGT | CGTGGCCCGA | AGTATGGGCG | GCAAGGAGGA | 1980 |
| CTTGATCTGG | GAGCTTCTCA | ACCAGGCCCA | GGAACATTTT | GGCAAAGACA | AATCAAAAGA | 2040 |

-continued

```
ATTCCAACTA TTCAGCTCTC CCATGGGAAG GACCTGCTGT TTAAGGACTC TGCCCACGGG    2100
TTTTTAAAAG TCCCCCCAAG GATGGATGCC AAGATGTACC TGGGCTATGA GTATGTCACT    2160
GCCATCCGGA ATCTACGGGA AGGCACATGC CCAGAAGCCC CAACAGATGA ATGCAAGCCT    2220
GTGAAGTGGT GTGCGCTGAG CCACCACGAG AGGCTCAAGT GTGATGAGTG GAGTGTTAAC    2280
AGTGTAGGGA AAATAGAGTG TGTATCAGCA GAGACCACCG AAGACTGCAT CGCCAAGATC    2340
ATGAATGGAG AAGCTGATGC CATGAGCTTG GATGGAGGGT TTGTCTACAT AGCGGGCAAG    2400
TGTGGTCTGG TGCCTGTCTT GGCAGAAAAC TACAATAAGA GCGATAATTG TGAGGATACA    2460
CCAGAGGCAG GGTATTTTGC TGTAGCAGTG GTGAAGAAAT CAGCTTCTGA CCTCACCTGG    2520
GACAATCTGA AAGGCAAGAA GTCCTGCCAT ACGGCAGTTG GCAGAACCGC TGGCTGGAAC    2580
ATCCCCATGG GCCTGCTCTA CAATAAGATC AACCACTGCA GATTTGATGA ATTTTTCAGT    2640
GAAGGTTGTG CCCCTGGGTC TAAGAAAGAC TCCAGTCTCT GTAAGCTGTG TATGGGCTCA    2700
GGCCTAAACC TGTGTGAACC CAACAACAAA GAGGGATACT ACGGCTACAC AGGCGCTTTC    2760
AGGTGTCTGG TTGAGAAGGG AGATGTGGCC TTTGTGAAAC ACCAGACTGT CCCACAGAAC    2820
ACTGGGGGAA AAAACCCTGA TCCATGGGCT AAGAATCTGA ATGAAAAGA CTATGAGTTG    2880
CTGTGCCTTG ATGGTACCAG GAAACCTGTG GAGGAGTATG CGAACTGCCA CCTGGCCAGA    2940
GCCCCGAATC ACGCTGTGGT CACACGGAAA GATAAGGAAG CTTGCGTCCA CAAGATATTA    3000
CGTCAACAGC AGCACCTATT TGGAAGCAAC GTAACTGACT GCTCGGGCAA CTTTTGTTTG    3060
TTCCGGTCGG AAACCAAGGA CCTTCTGTTC AGAGATGACA CAGTATGTTT GGCCAAACTT    3120
CATGACAGAA ACACATATGA AAAATACTTA GGAGAAGAAT ATGTCAAGGC TGTTGGTAAC    3180
CTGAGAAAAT GCTCCACCTC ATCACTCCTG GAAGCCTGCA CTTTCCGTAG ACCTTAAAAT    3240
CTCAGAGGTA GGGCTGCCAC CAAGGTGAAG ATGGGAACGC AGATGATCCA TGAGTTTGCC    3300
CTGGTTTCAC TGGCCCAAGT GGTTTGTGCT AACCACGTCT GTCTTCACAG CTCTGTGTTG    3360
CCATGTGTGC TGAACAAAAA ATAAAAATTA TTATTGATTT TATATTTCGG GGGGGGGCT    3420
GCAGCCC                                                              3427
```

( 2 ) INFORMATION FOR SEQ ID NO:2:

( i ) SEQUENCE CHARACTERISTICS:
        ( A ) LENGTH: 1074 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:2:

```
Met Gly Pro Trp Gly Trp Lys Leu Arg Trp Thr Val Ala Leu Leu Leu
 1               5                  10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
```

|     |     |     |     |     | 100 |     |     |     |     | 105 |     |     |     |     | 110 |
| --- | --- | --- | --- | --- | --- | --- | --- | --- | --- | --- | --- | --- | --- | --- | --- |
| Glu | Phe | Arg | Cys | His | Asp | Gly | Lys | Cys | Ile | Ser | Arg | Gln | Phe | Val | Cys |
|     |     |     | 115 |     |     |     | 120 |     |     |     |     | 125 |     |     |     |
| Asp | Ser | Asp | Arg | Asp | Cys | Leu | Asp | Gly | Ser | Asp | Glu | Ala | Ser | Cys | Pro |
|     |     | 130 |     |     |     | 135 |     |     |     | 140 |     |     |     |     |     |
| Val | Leu | Thr | Cys | Gly | Pro | Ala | Ser | Phe | Gln | Cys | Asn | Ser | Ser | Thr | Cys |
| 145 |     |     |     |     | 150 |     |     |     |     | 155 |     |     |     |     | 160 |
| Ile | Pro | Gln | Leu | Trp | Ala | Cys | Asp | Asn | Asp | Pro | Asp | Cys | Glu | Asp | Gly |
|     |     |     |     | 165 |     |     |     |     | 170 |     |     |     |     |     | 175 |
| Ser | Asp | Glu | Trp | Pro | Gln | Arg | Cys | Arg | Gly | Leu | Tyr | Val | Phe | Gln | Gly |
|     |     |     | 180 |     |     |     |     | 185 |     |     |     |     | 190 |     |     |
| Asp | Ser | Ser | Pro | Cys | Ser | Ala | Phe | Glu | Phe | His | Cys | Leu | Ser | Gly | Glu |
|     |     | 195 |     |     |     |     | 200 |     |     |     |     | 205 |     |     |     |
| Cys | Ile | His | Ser | Ser | Trp | Arg | Cys | Asp | Gly | Gly | Pro | Asp | Cys | Lys | Asp |
|     | 210 |     |     |     |     | 215 |     |     |     |     | 220 |     |     |     |     |
| Lys | Ser | Asp | Glu | Glu | Asn | Cys | Ala | Val | Ala | Thr | Cys | Arg | Pro | Asp | Glu |
| 225 |     |     |     |     | 230 |     |     |     |     | 235 |     |     |     |     | 240 |
| Phe | Gln | Cys | Ser | Asp | Gly | Asn | Cys | Ile | His | Gly | Ser | Arg | Gln | Cys | Asp |
|     |     |     |     | 245 |     |     |     |     | 250 |     |     |     |     | 255 |     |
| Arg | Glu | Tyr | Asp | Cys | Lys | Asp | Met | Ser | Asp | Glu | Val | Gly | Cys | Val | Asn |
|     |     |     | 260 |     |     |     |     | 265 |     |     |     |     | 270 |     |     |
| Val | Thr | Leu | Cys | Glu | Gly | Pro | Asn | Lys | Phe | Lys | Cys | His | Ser | Gly | Glu |
|     |     | 275 |     |     |     |     | 280 |     |     |     |     | 285 |     |     |     |
| Cys | Ile | Thr | Leu | Asp | Lys | Val | Cys | Asn | Met | Ala | Arg | Asp | Cys | Arg | Asp |
|     | 290 |     |     |     |     | 295 |     |     |     |     | 300 |     |     |     |     |
| Trp | Ser | Asp | Glu | Pro | Ile | Lys | Glu | Cys | Gly | Thr | Asn | Glu | Cys | Leu | Asp |
| 305 |     |     |     |     | 310 |     |     |     |     | 315 |     |     |     |     | 320 |
| Asn | Asn | Gly | Gly | Cys | Ser | His | Val | Cys | Asn | Asp | Leu | Lys | Ile | Gly | Tyr |
|     |     |     |     | 325 |     |     |     |     | 330 |     |     |     |     | 335 |     |
| Glu | Cys | Leu | Cys | Pro | Asp | Gly | Phe | Gln | Leu | Val | Ala | Gln | Arg | Arg | Cys |
|     |     |     | 340 |     |     |     |     | 345 |     |     |     |     | 350 |     |     |
| Glu | Asp | Ile | Asp | Glu | Cys | Gln | Asp | Pro | Asp | Thr | Cys | Ser | Gln | Leu | Cys |
|     |     | 355 |     |     |     |     | 360 |     |     |     |     | 365 |     |     |     |
| Val | Asn | Leu | Glu | Gly | Gly | Tyr | Lys | Cys | Gln | Cys | Glu | Glu | Gly | Phe | Gln |
|     | 370 |     |     |     |     | 375 |     |     |     |     | 380 |     |     |     |     |
| Leu | Asp | Pro | His | Thr | Lys | Ala | Cys | Lys | Ala | Val | Val | Pro | Asp | Lys | Thr |
| 385 |     |     |     |     | 390 |     |     |     |     | 395 |     |     |     |     | 400 |
| Val | Arg | Trp | Cys | Ala | Val | Ser | Glu | His | Glu | Ala | Thr | Lys | Cys | Gln | Ser |
|     |     |     |     | 405 |     |     |     |     | 410 |     |     |     |     | 415 |     |
| Phe | Arg | Asp | His | Met | Lys | Ser | Val | Ile | Pro | Ser | Asp | Gly | Pro | Ser | Val |
|     |     |     | 420 |     |     |     |     | 425 |     |     |     |     | 430 |     |     |
| Ala | Cys | Val | Lys | Lys | Ala | Ser | Tyr | Leu | Asp | Cys | Ile | Arg | Ala | Ile | Ala |
|     |     | 435 |     |     |     |     | 440 |     |     |     |     | 445 |     |     |     |
| Ala | Asn | Glu | Ala | Asp | Ala | Val | Thr | Leu | Asp | Ala | Gly | Leu | Val | Tyr | Asp |
|     | 450 |     |     |     |     | 455 |     |     |     |     | 460 |     |     |     |     |
| Ala | Tyr | Leu | Ala | Pro | Asn | Asn | Leu | Lys | Pro | Val | Val | Ala | Glu | Phe | Tyr |
| 465 |     |     |     |     | 470 |     |     |     |     | 475 |     |     |     |     | 480 |
| Gly | Ser | Lys | Glu | Asp | Pro | Gln | Thr | Phe | Tyr | Tyr | Ala | Val | Ala | Val | Val |
|     |     |     |     | 485 |     |     |     |     | 490 |     |     |     |     | 495 |     |
| Lys | Lys | Asp | Ser | Gly | Phe | Gln | Met | Asn | Gln | Leu | Arg | Gly | Lys | Lys | Ser |
|     |     |     | 500 |     |     |     |     | 505 |     |     |     |     | 510 |     |     |
| Cys | His | Thr | Gly | Leu | Gly | Arg | Ser | Ala | Gly | Trp | Asn | Ile | Pro | Ile | Gly |
|     |     | 515 |     |     |     |     | 520 |     |     |     |     | 525 |     |     |     |

```
Leu  Leu  Tyr  Cys  Asp  Leu  Pro  Glu  Pro  Arg  Lys  Pro  Leu  Glu  Lys  Ala
     530                 535                      540

Val  Ala  Asn  Phe  Phe  Ser  Gly  Ser  Cys  Ala  Pro  Cys  Ala  Asp  Gly  Thr
545                      550                 555                           560

Asp  Phe  Pro  Gln  Leu  Cys  Gln  Leu  Cys  Pro  Gly  Cys  Gly  Cys  Ser  Thr
                    565                 570                           575

Leu  Asn  Gln  Tyr  Phe  Gly  Tyr  Ser  Gly  Ala  Phe  Lys  Cys  Leu  Lys  Asp
                580                      585                      590

Gly  Ala  Gly  Asp  Val  Ala  Phe  Val  Lys  His  Ser  Thr  Ile  Phe  Glu  Asn
               595                 600                      605

Leu  Ala  Asn  Lys  Ala  Asp  Arg  Asp  Gln  Tyr  Glu  Leu  Leu  Cys  Leu  Asp
     610                      615                      620

Asn  Thr  Arg  Lys  Pro  Val  Asp  Glu  Tyr  Lys  Asp  Cys  His  Leu  Ala  Gln
625                      630                      635                          640

Val  Pro  Ser  His  Thr  Val  Val  Ala  Arg  Ser  Met  Gly  Gly  Lys  Glu  Asp
                    645                      650                      655

Leu  Ile  Trp  Glu  Leu  Leu  Asn  Gln  Ala  Gln  Glu  His  Phe  Gly  Lys  Asp
               660                      665                      670

Lys  Ser  Lys  Glu  Phe  Gln  Leu  Phe  Ser  Ser  Pro  His  Gly  Lys  Asp  Leu
          675                      680                      685

Leu  Phe  Lys  Asp  Ser  Ala  His  Gly  Phe  Leu  Lys  Val  Pro  Pro  Arg  Met
     690                      695                      700

Asp  Ala  Lys  Met  Tyr  Leu  Gly  Tyr  Glu  Tyr  Val  Thr  Ala  Ile  Arg  Asn
705                      710                      715                          720

Leu  Arg  Glu  Gly  Thr  Cys  Pro  Glu  Ala  Pro  Thr  Asp  Glu  Cys  Lys  Pro
                    725                      730                      735

Val  Lys  Trp  Cys  Ala  Leu  Ser  His  His  Glu  Arg  Leu  Lys  Cys  Asp  Glu
               740                      745                      750

Trp  Ser  Val  Asn  Ser  Val  Gly  Lys  Ile  Glu  Cys  Val  Ser  Ala  Glu  Thr
          755                      760                      765

Thr  Glu  Asp  Cys  Ile  Ala  Lys  Ile  Met  Asn  Gly  Glu  Ala  Asp  Ala  Met
     770                      775                      780

Ser  Leu  Asp  Gly  Gly  Phe  Val  Tyr  Ile  Ala  Gly  Lys  Cys  Gly  Leu  Val
785                      790                      795                          800

Pro  Val  Leu  Ala  Glu  Asn  Tyr  Asn  Lys  Ser  Asp  Asn  Cys  Glu  Asp  Thr
                    805                      810                      815

Pro  Glu  Ala  Gly  Tyr  Phe  Ala  Val  Ala  Val  Val  Lys  Lys  Ser  Ala  Ser
               820                      825                      830

Asp  Leu  Thr  Trp  Asp  Asn  Leu  Lys  Gly  Lys  Lys  Ser  Cys  His  Thr  Ala
          835                      840                      845

Val  Gly  Arg  Thr  Ala  Gly  Trp  Asn  Ile  Pro  Met  Gly  Leu  Leu  Tyr  Asn
     850                      855                      860

Lys  Ile  Asn  His  Cys  Arg  Phe  Asp  Glu  Phe  Phe  Ser  Glu  Gly  Cys  Ala
865                      870                      875                          880

Pro  Gly  Ser  Lys  Lys  Asp  Ser  Ser  Leu  Cys  Lys  Leu  Cys  Met  Gly  Ser
                    885                      890                      895

Gly  Leu  Asn  Leu  Cys  Glu  Pro  Asn  Asn  Lys  Glu  Gly  Tyr  Tyr  Gly  Tyr
               900                      905                      910

Thr  Gly  Ala  Phe  Arg  Cys  Leu  Val  Glu  Lys  Gly  Asp  Val  Ala  Phe  Val
          915                      920                      925

Lys  His  Gln  Thr  Val  Pro  Gln  Asn  Thr  Gly  Gly  Lys  Asn  Pro  Asp  Pro
     930                      935                      940

Trp  Ala  Lys  Asn  Leu  Asn  Glu  Lys  Asp  Tyr  Glu  Leu  Leu  Cys  Leu  Asp
945                      950                      955                          960
```

|   |   |   |   |   |   |   |   |   |   |   |   |   |   |
|---|---|---|---|---|---|---|---|---|---|---|---|---|---|
| Gly | Thr | Arg | Lys | Pro<br>965 | Val | Glu | Glu | Tyr<br>970 | Ala | Asn | Cys | His | Leu<br>975 | Ala | Arg |

| Ala | Pro | Asn | His<br>980 | Ala | Val | Val | Thr | Arg<br>985 | Lys | Asp | Lys | Glu | Ala<br>990 | Cys | Val |

| His | Lys | Ile | Leu<br>995 | Arg | Gln | Gln | Gln | His<br>1000 | Leu | Phe | Gly | Ser | Asn<br>1005 | Val | Thr |

| Asp | Cys | Ser<br>1010 | Gly | Asn | Phe | Cys<br>1015 | Leu | Phe | Arg | Ser | Glu<br>1020 | Thr | Lys | Asp | Leu |

| Leu | Phe | Arg | Asp | Asp | Thr<br>1030 | Val | Cys | Leu | Ala | Lys<br>1035 | Leu | His | Asp | Arg | Asn<br>1040 |
| 1025 |

| Thr | Tyr | Glu | Lys | Tyr<br>1045 | Leu | Gly | Glu | Glu | Tyr<br>1050 | Val | Lys | Ala | Val | Gly<br>1055 | Asn |

| Leu | Arg | Lys | Cys<br>1060 | Ser | Thr | Ser | Ser | Leu<br>1065 | Leu | Glu | Ala | Cys | Thr<br>1070 | Phe | Arg |

Arg Pro (2) INFORMATION FOR SEQ ID NO:3:

(i) SEQUENCE CHARACTERISTICS:
(A) LENGTH: 4601 base pairs
(B) TYPE: nucleic acid
(C) STRANDEDNESS: both
(D) TOPOLOGY: both (ii) MOLECULE TYPE: cDNA to mRNA (xi) SEQUENCE DESCRIPTION: SEQ ID NO:3:

```
AGAGGCTGCG AGCATGGGGC CCTGGGGCTG GAAATTGCGC TGGACCGTCG CCTTGCTCCT      60
CGCCGCGGCG GGGACTGCAG TGGGCGACAG ATGTGAAAGA AACGAGTTCC AGTGCCAAGA     120
CGGGAAATGC ATCTCCTACA AGTGGGTCTG CGATGGCAGC GCTGAGTGCC AGGATGGCTC     180
TGATGAGTCC CAGGAGACGT GCTTGTCTGT CACCTGCAAA TCCGGGGACT TCAGCTGTGG     240
GGGCCGTGTC AACCGCTGCA TTCCTCAGTT CTGGAGGTGC GATGGCCAAG TGGACTGCGA     300
CAACGGCTCA GACGAGCAAG GCTGTCCCCC AAGACGTGC TCCCAGGACG AGTTTCGCTG      360
CCACGATGGG AAGTGCATCT CTCGGCAGTT CGTCTGTGAC TCAGACCGGG ACTGCTTGGA     420
CGGCTCAGAC GAGGCCTCCT GCCCGGTGCT CACCTGTGGT CCCGCCAGCT TCCAGTGCAA     480
CAGCTCCACC TGCATCCCCC AGCTGTGGGC CTGCGACAAC GACCCCGACT GCGAAGATGG     540
CTCGGATGAG TGGCCGCAGC GCTGTAGGGG TCTTTACGTG TTCCAAGGGG ACAGTAGCCC     600
CTGCTCGGCC TTCGAGTTCC ACTGCCTAAG TGGCGAGTGC ATCCACTCCA GCTGGCGCTG     660
TGATGGTGGC CCCGACTGCA AGGACAAATC TGACGAGGAA AACTGCGCTG TGGCCACCTG     720
TCGCCCTGAC GAATTCCAGT GCTCTGATGG AAACTGCATC CATGGCAGCC GGCAGTGTGA     780
CCGGGAATAT GACTGCAAGG ACATGAGCGA TGAAGTTGGC TGCGTTAATG TGACACTCTG     840
CGAGGGACCC AACAAGTTCA AGTGTCACAG CGGCGAATGC ATCACCCTGG ACAAAGTCTG     900
CAACATGGCT AGAGACTGCC GGGACTGGTC AGATGAACCC ATCAAAGAGT GCGGGACCAA     960
CGAATGCTTG GACAACAACG GCGGCTGTTC CCACGTCTGC AATGACCTTA AGATCGGCTA    1020
CGAGTGCCTG TGCCCCGACG GCTTCCAGCT GGTGGCCCAG CGAAGATGCG AAGATATCGA    1080
TGAGTGTCAG GATCCCGACA CCTGCAGCCA GCTCTGCGTG AACCTGGAGG TGGCTACAA     1140
GTGCCAGTGT GAGGAAGGCT TCCAGCTGGA CCCCCACACG AAGGCCTGCA AGGCTGTGGG    1200
CTCCATCGCC TACCTCTTCT TCACCAACCG GCACGAGGTC AGGAAGATGA CGCTGGACCG    1260
GAGCGAGTAC ACCAGCCTCA TCCCCAACCT GAGGAACGTG GTCGCTCTGG ACACGGAGGT    1320
```

```
GGCCAGCAAT  AGAATCTACT  GGTCTGACCT  GTCCCAGAGA  ATGATCTGCA  GCACCCAGCT  1380
TGACAGAGCC  CACGGCGTCT  CTTCCTATGA  CACCGTCATC  AGCAGGGACA  TCCAGGCCCC  1440
CGACGGGCTG  GCTGTGGACT  GGATCCACAG  CAACATCTAC  TGGACCGACT  CTGTCCTGGG  1500
CACTGTCTCT  GTTGCGGATA  CCAAGGGCGT  GAAGAGGAAA  ACGTTATTCA  GGGAGAACGG  1560
CTCCAAGCCA  AGGGCCATCG  TGGTGGATCC  TGTTCATGGC  TTCATGTACT  GGACTGACTG  1620
GGGAACTCCC  GCCAAGATCA  AGAAAGGGGG  CCTGAATGGT  GTGGACATCT  ACTCGCTGGT  1680
GACTGAAAAC  ATTCAGTGGC  CCAATGGCAT  CACCCTAGAT  CTCCTCAGTG  GCCGCCTCTA  1740
CTGGGTTGAC  TCCAAACTTC  ACTCCATCTC  AAGCATCGAT  GTCAATGGGG  GCAACCGGAA  1800
GACCATCTTG  GAGGATGAAA  AGAGGCTGGC  CCACCCCTTC  TCCTTGGCCG  TCTTTGAGGA  1860
CAAAGTATTT  TGGACAGATA  TCATCAACGA  AGCCATTTTC  AGTGCCAACC  GCCTCACAGG  1920
TTCCGATGTC  AACTTGTTGG  CTGAAAACCT  ACTGTCCCCA  GAGGATATGG  TCCTCTTCCA  1980
CAACCTCACC  CAGCCAAGAG  GAGTGAACTG  GTGTGAGAGG  ACCACCCTGA  GCAATGGCGG  2040
CTGCCAGTAT  CTGTGCCTCC  CGCCCCGCAG  ATCAACCCCC  ACTCGCCCAA  GTTTACCTGC  2100
GCCTGCCCGG  ACGGCATGCT  GCTGGCCAGG  GACATGAGGA  GCTGCCTCAC  AGAGGCTGAG  2160
GCTGCAGTGG  CCACCCAGGA  GACATCCACC  GTCAGGCTAA  AGGTCGTCCC  TGATAAAACT  2220
GTGAGATGGT  GTGCAGTGTC  GGAGCATGAG  GCCACTAAGT  GCCAGAGTTT  CCGCGACCAT  2280
ATGAAAAGCG  TCATTCCATC  CGATGGTCCC  AGTGTTGCTT  GTGTGAAGAA  AGCCTCCTAC  2340
CTTGATTGCA  TCAGGGCCAT  TGCGGCAAAC  GAAGCGGATG  CTGTGACACT  GGATGCAGGT  2400
TTGGTGTATG  ATGCTTACTT  GGCTCCCAAT  AACCTGAAGC  CTGTGGTGGC  AGAGTTCTAT  2460
GGGTCAAAAG  AGGATCCACA  GACTTTCTAT  TATGCTGTTG  CTGTGGTGAA  GAAGGATAGT  2520
GGCTTCCAGA  TGAACCAGCT  TCGAGGCAAG  AAGTCCTGCC  ACACGGGTCT  AGGCAGGTCC  2580
GCTGGGTGGA  ACATCCCCAT  AGGCTTACTT  TACTGTGACT  TACCTGAGCC  ACGTAAACCT  2640
CTTGAGAAAG  CAGTGGCCAA  TTTCTTCTCG  GGCAGCTGTG  CCCCTTGTGC  GGATGGGACG  2700
GACTTCCCCC  AGCTGTGTCA  ACTGTGTCCA  GGGTGTGGCT  GCTCCACCCT  TAACCAATAC  2760
TTCGGCTACT  CGGGAGCCTT  CAAGTGTCTG  AAGGATGGTG  CTGGGGATGT  GGCCTTTGTC  2820
AAGCACTCGA  CTATATTTGA  GAACTTGGCA  ACAAGGCTG   ACAGGGACCA  GTATGAGCTG  2880
CTTTGCCTAG  ACAACACCCG  GAAGCCGGTA  GATGAATACA  AGGACTGCCA  CTTGGCCCAG  2940
GTCCCTTCTC  ATACCGTCGT  GGCCCGAAGT  ATGGGCGGCA  AGGAGGACTT  GATCTGGGAG  3000
CTTCTCAACC  AGGCCCAGGA  ACATTTTGGC  AAAGACAAAT  CAAAAGAATT  CCAACTATTC  3060
AGCTCTCCTC  ATGGGAAGGA  CCTGCTGTTT  AAGGACTCTG  CCCACGGGTT  TTTAAAAGTC  3120
CCCCCAAGGA  TGGATGCCAA  GATGTACCTG  GGCTATGAGT  ATGTCACTGC  CATCCGGAAT  3180
CTACGGGAAG  GCACATGCCC  AGAAGCCCCA  ACAGATGAAT  GCAAGCCTGT  GAAGTGGTGT  3240
GCGCTGAGCC  ACCACGAGAG  GCTCAAGTGT  GATGAGTGGA  GTGTTAACAG  TGTAGGGAAA  3300
ATAGAGTGTG  TATCAGCAGA  GACCACCGAA  GACTGCATCG  CCAAGATCAT  GAATGGAGAA  3360
GCTGATGCCA  TGAGCTTGGA  TGGAGGGTTT  GTCTACATAG  CGGGCAAGTG  TGGTCTGGTG  3420
CCTGTCTTGG  CAGAAAACTA  CAATAAGAGC  GATAATTGTG  AGGATACACC  AGAGGCAGGG  3480
TATTTTGCTG  TAGCAGTGGT  GAAGAAATCA  GCTTCTGACC  TCACCTGGGA  CAATCTGAAA  3540
GGCAAGAAGT  CCTGCCATAC  GGCAGTTGGC  AGAACGCTG   GCTGGAACAT  CCCCATGGGC  3600
CTGCTCTACA  ATAAGATCAA  CCACTGCAGA  TTTGATGAAT  TTTTCAGTGA  AGGTTGTGCC  3660
CCTGGGTCTA  AGAAAGACTC  CAGTCTCTGT  AAGCTGTGTA  TGGGCTCAGG  CCTAAACCTG  3720
```

-continued

```
TGTGAACCCA ACAACAAAGA GGGATACTAC GGCTACACAG GCGCTTTCAG GTGTCTGGTT      3780

GAGAAGGGAG ATGTGGCCTT TGTGAAACAC CAGACTGTCC CACAGAACAC TGGGGGAAAA      3840

AACCCTGATC CATGGGCTAA GAATCTGAAT GAAAAAGACT ATGAGTTGCT GTGCCTTGAT      3900

GGTACCAGGA AACCTGTGGA GGAGTATGCG AACTGCCACC TGGCCAGAGC CCCGAATCAC      3960

GCTGTGGTCA CACGGAAAGA TAAGGAAGCT TGCGTCCACA AGATATTACG TCAACAGCAG      4020

CACCTATTTG GAAGCAACGT AACTGACTGC TCGGGCAACT TTTGTTTGTT CCGGTCGGAA      4080

ACCAAGGACC TTCTGTTCAG AGATGACACG TATGTTTGGC CAAACTTCAT GACAGAAACA      4140

CATATGAAAA ATACTTAGGA GAAGAATATG TCAAGGCTGT TGGTAACCTG AGAAAATGCT      4200

CCACCTCATC ACTCCTGGAA GCCTGCACTT TCCGTAGACC TTAAAATCTC AGAGGTAGGG      4260

CTGCCACCAA GGTGAAGATG GGAACGCAGA TGATCCATGA GTTTGCCCTG GTTTCACTGG      4320

CCCAAGTGGT TTGTGCTAAC CACGTCTGTC TTCACAGCTC TGTGTTGCCA TGTGTGCTGA      4380

ACAAAAAATA AAAATTATTA TTGATTTTAT ATTTCGGGGG GGGGGCTGCA GCCCCTAGAC      4440

CTGAGGGTCC CCACCTGGGA CCCTTGAGAG TATCAGGTCT CCCACGTGGG AGACAAGAAA      4500

TCCCTGTTTA ATATTTAAAC AGCAGTGTTC CCCATCTGGG TCCTTGCACC CCTCACTCTG      4560

GCCTCAGCCG ACTGCACAGC GGCCCCTGCA TCCCCTCTAG A                         4601
```

( 2 ) INFORMATION FOR SEQ ID NO:4:

( i ) SEQUENCE CHARACTERISTICS:
        ( A ) LENGTH: 1410 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:4:

```
Met  Gly  Pro  Trp  Gly  Trp  Lys  Leu  Arg  Trp  Thr  Val  Ala  Leu  Leu  Leu
 1              5                        10                       15

Ala  Ala  Ala  Gly  Thr  Ala  Val  Gly  Asp  Arg  Cys  Glu  Arg  Asn  Glu  Phe
                20                       25                       30

Gln  Cys  Gln  Asp  Gly  Lys  Cys  Ile  Ser  Tyr  Lys  Trp  Val  Cys  Asp  Gly
            35                       40                       45

Ser  Ala  Glu  Cys  Gln  Asp  Gly  Ser  Asp  Glu  Ser  Gln  Glu  Thr  Cys  Leu
        50                       55                       60

Ser  Val  Thr  Cys  Lys  Ser  Gly  Asp  Phe  Ser  Cys  Gly  Gly  Arg  Val  Asn
 65                      70                       75                       80

Arg  Cys  Ile  Pro  Gln  Phe  Trp  Arg  Cys  Asp  Gly  Gln  Val  Asp  Cys  Asp
                85                       90                       95

Asn  Gly  Ser  Asp  Glu  Gln  Gly  Cys  Pro  Pro  Lys  Thr  Cys  Ser  Gln  Asp
            100                      105                      110

Glu  Phe  Arg  Cys  His  Asp  Gly  Lys  Cys  Ile  Ser  Arg  Gln  Phe  Val  Cys
            115                      120                      125

Asp  Ser  Asp  Arg  Asp  Cys  Leu  Asp  Gly  Ser  Asp  Glu  Ala  Ser  Cys  Pro
        130                      135                      140

Val  Leu  Thr  Cys  Gly  Pro  Ala  Ser  Phe  Gln  Cys  Asn  Ser  Ser  Thr  Cys
145                      150                      155                      160

Ile  Pro  Gln  Leu  Trp  Ala  Cys  Asp  Asn  Asp  Pro  Asp  Cys  Glu  Asp  Gly
                165                      170                      175

Ser  Asp  Glu  Trp  Pro  Gln  Arg  Cys  Arg  Gly  Leu  Tyr  Val  Phe  Gln  Gly
            180                      185                      190
```

```
Asp  Ser  Ser  Pro  Cys  Ser  Ala  Phe  Glu  Phe  His  Cys  Leu  Ser  Gly  Glu
          195            200                      205

Cys  Ile  His  Ser  Ser  Trp  Arg  Cys  Asp  Gly  Gly  Pro  Asp  Cys  Lys  Asp
     210                 215                      220

Lys  Ser  Asp  Glu  Glu  Asn  Cys  Ala  Val  Ala  Thr  Cys  Arg  Pro  Asp  Glu
225                      230                 235                           240

Phe  Gln  Cys  Ser  Asp  Gly  Asn  Cys  Ile  His  Gly  Ser  Arg  Gln  Cys  Asp
               245                      250                      255

Arg  Glu  Tyr  Asp  Cys  Lys  Asp  Met  Ser  Asp  Glu  Val  Gly  Cys  Val  Asn
               260            265                           270

Val  Thr  Leu  Cys  Glu  Gly  Pro  Asn  Lys  Phe  Lys  Cys  His  Ser  Gly  Glu
               275                 280                      285

Cys  Ile  Thr  Leu  Asp  Lys  Val  Cys  Asn  Met  Ala  Arg  Asp  Cys  Arg  Asp
     290                 295                      300

Trp  Ser  Asp  Glu  Pro  Ile  Lys  Glu  Cys  Gly  Thr  Asn  Glu  Cys  Leu  Asp
305                      310                 315                           320

Asn  Asn  Gly  Gly  Cys  Ser  His  Val  Cys  Asn  Asp  Leu  Lys  Ile  Gly  Tyr
               325                 330                           335

Glu  Cys  Leu  Cys  Pro  Asp  Gly  Phe  Gln  Leu  Val  Ala  Gln  Arg  Arg  Cys
               340                 345                      350

Glu  Asp  Ile  Asp  Glu  Cys  Gln  Asp  Pro  Asp  Thr  Cys  Ser  Gln  Leu  Cys
               355                 360                      365

Val  Asn  Leu  Glu  Gly  Gly  Tyr  Lys  Cys  Gln  Cys  Glu  Glu  Gly  Phe  Gln
370                                375                      380

Leu  Asp  Pro  His  Thr  Lys  Ala  Cys  Lys  Ala  Val  Gly  Ser  Ile  Ala  Tyr
385                      390                 395                           400

Leu  Phe  Phe  Thr  Asn  Arg  His  Glu  Val  Arg  Lys  Met  Thr  Leu  Asp  Arg
                    405                 410                      415

Ser  Glu  Tyr  Thr  Ser  Leu  Ile  Pro  Asn  Leu  Arg  Asn  Val  Val  Ala  Leu
                    420                 425                 430

Asp  Thr  Glu  Val  Ala  Ser  Asn  Arg  Ile  Tyr  Trp  Ser  Asp  Leu  Ser  Gln
          435                      440                      445

Arg  Met  Ile  Cys  Ser  Thr  Gln  Leu  Asp  Arg  Ala  His  Gly  Val  Ser  Ser
     450                 455                      460

Tyr  Asp  Thr  Val  Ile  Ser  Arg  Asp  Ile  Gln  Ala  Pro  Asp  Gly  Leu  Ala
465                      470                      475                      480

Val  Asp  Trp  Ile  His  Ser  Asn  Ile  Tyr  Trp  Thr  Asp  Ser  Val  Leu  Gly
                    485                      490                      495

Thr  Val  Ser  Val  Ala  Asp  Thr  Lys  Gly  Val  Lys  Arg  Lys  Thr  Leu  Phe
               500                 505                      510

Arg  Glu  Asn  Gly  Ser  Lys  Pro  Arg  Ala  Ile  Val  Val  Asp  Pro  Val  His
          515                      520                      525

Gly  Phe  Met  Tyr  Trp  Thr  Asp  Trp  Gly  Thr  Pro  Ala  Lys  Ile  Lys  Lys
530                      535                      540

Gly  Gly  Leu  Asn  Gly  Val  Asp  Ile  Tyr  Ser  Leu  Val  Thr  Glu  Asn  Ile
545                      550                      555                      560

Gln  Trp  Pro  Asn  Gly  Ile  Thr  Leu  Asp  Leu  Leu  Ser  Gly  Arg  Leu  Tyr
                    565                 570                      575

Trp  Val  Asp  Ser  Lys  Leu  His  Ser  Ile  Ser  Ser  Ile  Asp  Val  Asn  Gly
               580                 585                      590

Gly  Asn  Arg  Lys  Thr  Ile  Leu  Glu  Asp  Glu  Lys  Arg  Leu  Ala  His  Pro
          595                      600                      605

Phe  Ser  Leu  Ala  Val  Phe  Glu  Asp  Lys  Val  Phe  Trp  Thr  Asp  Ile  Ile
610                      615                      620
```

-continued

```
Asn   Glu   Ala   Ile   Phe   Ser   Ala   Asn   Arg   Leu   Thr   Gly   Ser   Asp   Val   Asn
625                     630                     635                                     640

Leu   Leu   Ala   Glu   Asn   Leu   Leu   Ser   Pro   Glu   Asp   Met   Val   Leu   Phe   His
                  645                     650                                     655

Asn   Leu   Thr   Gln   Pro   Arg   Gly   Val   Asn   Trp   Cys   Glu   Arg   Thr   Thr   Leu
                  660                     665                     670

Ser   Asn   Gly   Gly   Cys   Gln   Tyr   Leu   Cys   Leu   Pro   Ala   Pro   Gln   Ile   Asn
            675                     680                     685

Pro   His   Ser   Pro   Lys   Phe   Thr   Cys   Ala   Cys   Pro   Asp   Gly   Met   Leu   Leu
      690                     695                     700

Ala   Arg   Asp   Met   Arg   Ser   Cys   Leu   Thr   Glu   Ala   Glu   Ala   Val   Ala
705                     710                     715                                     720

Thr   Gln   Glu   Thr   Ser   Thr   Val   Arg   Leu   Lys   Val   Val   Pro   Asp   Lys   Thr
                        725                     730                                     735

Val   Arg   Trp   Cys   Ala   Val   Ser   Glu   His   Glu   Ala   Thr   Lys   Cys   Gln   Ser
                  740                     745                               750

Phe   Arg   Asp   His   Met   Lys   Ser   Val   Ile   Pro   Ser   Asp   Gly   Pro   Ser   Val
            755                     760                     765

Ala   Cys   Val   Lys   Lys   Ala   Ser   Tyr   Leu   Asp   Cys   Ile   Arg   Ala   Ile   Ala
      770                     775                     780

Ala   Asn   Glu   Ala   Asp   Ala   Val   Thr   Leu   Asp   Ala   Gly   Leu   Val   Tyr   Asp
785                     790                     795                                     800

Ala   Tyr   Leu   Ala   Pro   Asn   Asn   Leu   Lys   Pro   Val   Val   Ala   Glu   Phe   Tyr
                  805                     810                               815

Gly   Ser   Lys   Glu   Asp   Pro   Gln   Thr   Phe   Tyr   Tyr   Ala   Val   Ala   Val   Val
            820                     825                           830

Lys   Lys   Asp   Ser   Gly   Phe   Gln   Met   Asn   Gln   Leu   Arg   Gly   Lys   Lys   Ser
            835                     840                     845

Cys   His   Thr   Gly   Leu   Gly   Arg   Ser   Ala   Gly   Trp   Asn   Ile   Pro   Ile   Gly
      850                     855                     860

Leu   Leu   Tyr   Cys   Asp   Leu   Pro   Glu   Pro   Arg   Lys   Pro   Leu   Glu   Lys   Ala
865                     870                     875                                     880

Val   Ala   Asn   Phe   Phe   Ser   Gly   Ser   Cys   Ala   Pro   Cys   Ala   Asp   Gly   Thr
                  885                     890                           895

Asp   Phe   Pro   Gln   Leu   Cys   Gln   Leu   Cys   Pro   Gly   Cys   Gly   Cys   Ser   Thr
            900                     905                           910

Leu   Asn   Gln   Tyr   Phe   Gly   Tyr   Ser   Gly   Ala   Phe   Lys   Cys   Leu   Lys   Asp
            915                     920                     925

Gly   Ala   Gly   Asp   Val   Ala   Phe   Val   Lys   His   Ser   Thr   Ile   Phe   Glu   Asn
930                     935                           940

Leu   Ala   Asn   Lys   Ala   Asp   Arg   Asp   Gln   Tyr   Glu   Leu   Leu   Cys   Leu   Asp
945                     950                     955                                     960

Asn   Thr   Arg   Lys   Pro   Val   Asp   Glu   Tyr   Lys   Asp   Cys   His   Leu   Ala   Gln
                  965                     970                           975

Val   Pro   Ser   His   Thr   Val   Val   Ala   Arg   Ser   Met   Gly   Gly   Lys   Glu   Asp
            980                     985                     990

Leu   Ile   Trp   Glu   Leu   Leu   Asn   Gln   Ala   Gln   Glu   His   Phe   Gly   Lys   Asp
            995                     1000                    1005

Lys   Ser   Lys   Glu   Phe   Gln   Leu   Phe   Ser   Ser   Pro   His   Gly   Lys   Asp   Leu
            1010                    1015                    1020

Leu   Phe   Lys   Asp   Ser   Ala   His   Gly   Phe   Leu   Lys   Val   Pro   Pro   Arg   Met
1025                    1030                    1035                                    1040

Asp   Ala   Lys   Met   Tyr   Leu   Gly   Tyr   Glu   Tyr   Val   Thr   Ala   Ile   Arg   Asn
```

-continued

|  | 1045 | 1050 | 1055 |
|---|---|---|---|

Leu Arg Glu Gly Thr Cys Pro Glu Ala Pro Thr Asp Glu Cys Lys Pro
                1060              1065              1070

Val Lys Trp Cys Ala Leu Ser His His Glu Arg Leu Lys Cys Asp Glu
        1075              1080              1085

Trp Ser Val Asn Ser Val Gly Lys Ile Glu Cys Val Ser Ala Glu Thr
        1090              1095              1100

Thr Glu Asp Cys Ile Ala Lys Ile Met Asn Gly Glu Ala Asp Ala Met
1105              1110              1115              1120

Ser Leu Asp Gly Gly Phe Val Tyr Ile Ala Gly Lys Cys Gly Leu Val
                1125              1130              1135

Pro Val Leu Ala Glu Asn Tyr Asn Lys Ser Asp Asn Cys Glu Asp Thr
                1140              1145              1150

Pro Glu Ala Gly Tyr Phe Ala Val Ala Val Val Lys Lys Ser Ala Ser
                1155              1160              1165

Asp Leu Thr Trp Asp Asn Leu Lys Gly Lys Lys Ser Cys His Thr Ala
        1170              1175              1180

Val Gly Arg Thr Ala Gly Trp Asn Ile Pro Met Gly Leu Leu Tyr Asn
1185              1190              1195              1200

Lys Ile Asn His Cys Arg Phe Asp Glu Phe Phe Ser Glu Gly Cys Ala
                1205              1210              1215

Pro Gly Ser Lys Lys Asp Ser Ser Leu Cys Lys Leu Cys Met Gly Ser
                1220              1225              1230

Gly Leu Asn Leu Cys Glu Pro Asn Asn Lys Glu Gly Tyr Tyr Gly Tyr
                1235              1240              1245

Thr Gly Ala Phe Arg Cys Leu Val Glu Lys Gly Asp Val Ala Phe Val
        1250              1255              1260

Lys His Gln Thr Val Pro Gln Asn Thr Gly Gly Lys Asn Pro Asp Pro
1265              1270              1275              1280

Trp Ala Lys Asn Leu Asn Glu Lys Asp Tyr Glu Leu Leu Cys Leu Asp
                1285              1290              1295

Gly Thr Arg Lys Pro Val Glu Glu Tyr Ala Asn Cys His Leu Ala Arg
        1300              1305              1310

Ala Pro Asn His Ala Val Val Thr Arg Lys Asp Lys Glu Ala Cys Val
        1315              1320              1325

His Lys Ile Leu Arg Gln Gln Gln His Leu Phe Gly Ser Asn Val Thr
        1330              1335              1340

Asp Cys Ser Gly Asn Phe Cys Leu Phe Arg Ser Glu Thr Lys Asp Leu
1345              1350              1355              1360

Leu Phe Arg Asp Asp Thr Val Cys Leu Ala Lys Leu His Asp Arg Asn
                1365              1370              1375

Thr Tyr Glu Lys Tyr Leu Gly Glu Glu Tyr Val Lys Ala Val Gly Asn
                1380              1385              1390

Leu Arg Lys Cys Ser Thr Ser Ser Leu Leu Glu Ala Cys Thr Phe Arg
                1395              1400              1405

Arg Pro
1410

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GCTGTGGCCA CCTGTCGCCC TGAC 24

( 2 ) INFORMATION FOR SEQ ID NO:6:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TGCACACCAT CTCACAGTTT TATCAGGGAC CACAGCCTTG CAGGCCTTCG TGTGGGGTC 60

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GCCTCGAAGC TGGTTCATCT G 21

( 2 ) INFORMATION FOR SEQ ID NO:8:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GACCCCCACA CGAAGGCCTG CAAGGCTGTG GTCCTGATAA AACTGTGAGA TGGTGTGCA 59

( 2 ) INFORMATION FOR SEQ ID NO:9:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TGCACACCAT CTCACAGTTT TATCAGGGAC GACCTTTAGC CTGACGGT 48

( 2 ) INFORMATION FOR SEQ ID NO:10:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TCAGTGGCCC AATGGCATC 19

( 2 ) INFORMATION FOR SEQ ID NO:11:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
CAGGAGACAT  CCACCGTCAG  GCTAAAGGTC  GTCCCTGATA  AAACTGTGAG  A                    51
```

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
CTTCCCATGA  GGAGAGCT                                                             18
```